US007713705B2

(12) United States Patent
Buechler et al.

(10) Patent No.: US 7,713,705 B2
(45) Date of Patent: *May 11, 2010

(54) MARKERS FOR DIFFERENTIAL DIAGNOSIS AND METHODS OF USE THEREOF

(75) Inventors: Kenneth F. Buechler, Rancho Santa Fe, CA (US); Alan Maisel, Del Mar, CA (US)

(73) Assignee: Biosite, Inc., Waltham, MA (US)

( * ) Notice: Subject to any disclaimer, the term of this patent is extended or adjusted under 35 U.S.C. 154(b) by 1157 days.

This patent is subject to a terminal disclaimer.

(21) Appl. No.: 10/330,696

(22) Filed: Dec. 27, 2002

(65) Prior Publication Data

US 2004/0121343 A1 Jun. 24, 2004

Related U.S. Application Data

(60) Provisional application No. 60/436,301, filed on Dec. 24, 2002.

(51) Int. Cl.
G01N 33/50 (2006.01)
G01N 33/532 (2006.01)
G01N 33/533 (2006.01)
G01N 33/534 (2006.01)
G01N 33/535 (2006.01)
G01N 33/542 (2006.01)
G01N 21/00 (2006.01)
G01N 21/63 (2006.01)
G01N 21/64 (2006.01)

(52) U.S. Cl. .............................. 435/7.1; 435/4; 435/7.9; 435/7.91; 435/7.92; 435/7.93; 435/7.94; 435/7.95; 436/524; 436/525; 436/526; 436/527; 436/164; 436/172; 436/804; 422/68.1; 422/82.05; 422/82.06; 422/82.07; 422/82.08

(58) Field of Classification Search ................. 435/7.1, 435/7.72, 7.92, 7.94; 436/524–527
See application file for complete search history.

(56) References Cited

U.S. PATENT DOCUMENTS

| 4,900,662 | A |   | 2/1990  | Shah et al. |
|-----------|---|---|---------|-------------|
| 5,202,234 | A |   | 4/1993  | Shah et al. |
| 5,290,678 | A |   | 3/1994  | Jackowski |
| 5,382,515 | A |   | 1/1995  | Shah et al. |
| 5,382,522 | A |   | 1/1995  | Shah et al. |
| 5,453,359 | A |   | 9/1995  | Gargan |
| 5,480,792 | A |   | 1/1996  | Buechler et al. |
| 5,482,935 | A |   | 1/1996  | Adelman et al. |
| 5,525,524 | A |   | 6/1996  | Buechler et al. |
| 5,580,722 | A |   | 12/1996 | Foulkes et al. |
| 5,599,668 | A |   | 2/1997  | Stimpson et al. |
| 5,604,105 | A |   | 2/1997  | Jackowski |
| 5,624,850 | A | * | 4/1997  | Kumar et al. ............... 436/527 |
| 5,631,171 | A |   | 5/1997  | Sandstrom et al. |
| 5,679,526 | A |   | 10/1997 | Buechler et al. |
| 5,683,885 | A |   | 11/1997 | Kieback |
| 5,690,103 | A |   | 11/1997 | Groth et al. |
| 5,710,008 | A | * | 1/1998  | Jackowski .................. 435/7.4 |
| 5,747,274 | A |   | 5/1998  | Jackowski |
| 5,786,163 | A |   | 7/1998  | Hall |
| 5,795,725 | A |   | 8/1998  | Buechler et al. |
| 5,814,462 | A | * | 9/1998  | Weinberger ................. 435/7.1 |
| 5,824,799 | A |   | 10/1998 | Buechler et al. |
| 5,843,690 | A |   | 12/1998 | Gargan |
| 5,851,776 | A |   | 12/1998 | Valkirs |
| 5,885,527 | A |   | 3/1999  | Buechler |
| 5,922,615 | A |   | 7/1999  | Nowakowski et al. |
| 5,939,272 | A |   | 8/1999  | Buechler et al. |
| 5,947,124 | A |   | 9/1999  | Buechler et al. |
| 5,955,377 | A |   | 9/1999  | Maul et al. |
| 5,985,579 | A |   | 11/1999 | Buechler et al. |
| 6,019,944 | A |   | 2/2000  | Buechler |
| 6,040,147 | A |   | 3/2000  | Ridker |
| 6,099,469 | A |   | 8/2000  | Armstrong et al. |
| 6,113,855 | A |   | 9/2000  | Buechler |
| 6,143,576 | A |   | 11/2000 | Buechler |
| 6,147,688 | A |   | 11/2000 | Clair |
| 6,156,521 | A |   | 12/2000 | Buechler et al. |

(Continued)

FOREIGN PATENT DOCUMENTS

CA          2323685 A1      4/2001

(Continued)

OTHER PUBLICATIONS

Mitas et al. "Quantitative Real-time RT-PCR Detection of Breast Cancer Micrometastasis Using a Multigene Marker Panel", 2001, International Journal of Cancer, vol. 93, pp. 162-171.*
Baker, "In biomakers we trust?", Nature Biotechnology, 2005, vol. 23, pp. 297-304.*
Bast, Jr. et al., "Translational crossroads for biomarkers", Clin. Cancer Res., 2005, vol. 11, pp. 6103-6108.*
Kline et al., "New diagnostic tests for pulmonary embolism", Annals of Emergnecy Medicine, 2000, vol. 35, pp. 168-180.*
Labaer, "So, you want to look for biomarkers", J Proteome Res., 2005, vol. 4, pp. 1053-1059.*
Lindon, "Biomarkers: Present concepts and future promise," Preclinica, 2003, vol. 1 p. 221.*

(Continued)

Primary Examiner—Unsu Jung
(74) Attorney, Agent, or Firm—Wilson Sonsini Goodrich & Rosati

(57) ABSTRACT

The present invention provides methods for the identification and use of diagnostic markers for differential diagnosis of diseases. In a various aspects, the invention relates to methods and compositions able to determine the presence or absence of one, and preferably a plurality, of diseases that exhibit one or more similar or identical symptoms. Such methods and compositions can be used to provide assays and assay devices for use in determining the disease underlying one or more non-specific symptoms exhibited in a clinical setting.

13 Claims, No Drawings

U.S. PATENT DOCUMENTS

| | | | |
|---|---|---|---|
| 6,174,686 B1 | 1/2001 | Buechler et al. | |
| 6,180,418 B1 * | 1/2001 | Lee | 436/526 |
| 6,214,560 B1 | 4/2001 | Yguerabide et al. | |
| 6,251,691 B1 * | 6/2001 | Seul | 436/534 |
| 6,297,062 B1 * | 10/2001 | Gombinski | 436/526 |
| 6,300,141 B1 * | 10/2001 | Segal et al. | 435/287.1 |
| 6,309,888 B1 | 10/2001 | Holvoet et al. | |
| 6,443,889 B1 | 9/2002 | Groth et al. | |
| 6,461,828 B1 * | 10/2002 | Stanton et al. | 435/7.92 |
| 6,485,983 B1 | 11/2002 | Lu et al. | |
| 6,579,687 B1 | 6/2003 | Buechler et al. | |
| 6,627,404 B1 | 9/2003 | Buechler et al. | |
| 6,939,678 B1 | 9/2005 | Buechler et al. | |
| 6,991,907 B1 | 1/2006 | Buechler et al. | |
| 7,341,838 B2 | 3/2008 | Buechler et al. | |
| 7,358,055 B2 | 4/2008 | Valkirs et al. | |
| 7,361,473 B2 | 4/2008 | Valkirs et al. | |
| 2001/0023419 A1 | 9/2001 | Lapointe et al. | |
| 2002/0052000 A1 | 5/2002 | Parthasarathy et al. | |
| 2002/0055186 A1 | 5/2002 | Barry et al. | |
| 2002/0077470 A1 * | 6/2002 | Walker et al. | 536/24.3 |
| 2002/0081714 A1 * | 6/2002 | Jain et al. | 435/287.2 |
| 2002/0095260 A1 | 7/2002 | Huyn | |
| 2002/0106708 A1 | 8/2002 | Thomas et al. | |
| 2002/0127623 A1 * | 9/2002 | Minshull et al. | 435/7.92 |
| 2003/0022235 A1 | 1/2003 | Dahlen et al. | |
| 2003/0109420 A1 | 6/2003 | Valkirs et al. | |
| 2003/0119064 A1 | 6/2003 | Valkirs et al. | |
| 2003/0153014 A1 | 8/2003 | Shen et al. | |
| 2003/0199000 A1 | 10/2003 | Valkirs et al. | |
| 2003/0211544 A1 | 11/2003 | Buechler et al. | |
| 2003/0219734 A1 | 11/2003 | Buechler | |
| 2003/0233197 A1 | 12/2003 | Padilla et al. | |
| 2004/0121350 A1 | 6/2004 | Anderberg et al. | |
| 2004/0126767 A1 | 7/2004 | Anderberg et al. | |
| 2004/0171064 A1 | 9/2004 | Dahlen et al. | |
| 2004/0176914 A1 | 9/2004 | Buechler et al. | |
| 2004/0203083 A1 | 10/2004 | Buechler et al. | |
| 2004/0209307 A1 | 10/2004 | Valkirs et al. | |
| 2004/0219509 A1 | 11/2004 | Valkirs et al. | |
| 2004/0253637 A1 | 12/2004 | Buechler et al. | |
| 2005/0148024 A1 | 7/2005 | Buechler | |
| 2005/0164317 A1 | 7/2005 | Buechler et al. | |
| 2005/0181386 A1 | 8/2005 | Diamond et al. | |
| 2005/0244902 A1 | 11/2005 | Goetze et al. | |
| 2005/0255484 A1 | 11/2005 | Valkirs et al. | |
| 2006/0051825 A1 | 3/2006 | Buechler et al. | |
| 2006/0105419 A1 | 5/2006 | Blankenberg et al. | |
| 2007/0196880 A1 | 8/2007 | Buechler et al. | |
| 2007/0218498 A1 | 9/2007 | Buechler et al. | |
| 2007/0224643 A1 | 9/2007 | McPherson et al. | |
| 2007/0269836 A1 | 11/2007 | McPherson | |
| 2008/0045444 A1 | 2/2008 | Whittaker | |
| 2008/0118924 A1 | 5/2008 | Buechler | |
| 2008/0293920 A1 | 11/2008 | Buechler | |
| 2009/0061467 A1 | 3/2009 | Buechler et al. | |

FOREIGN PATENT DOCUMENTS

| | | |
|---|---|---|
| EP | 999447 A1 | 5/2000 |
| EP | 1666881 A2 | 6/2006 |
| GB | 2248688 A | 4/1992 |
| JP | 04-258765 | 9/1992 |
| WO | WO 93/24531 A1 | 12/1993 |
| WO | WO 96/32648 | 10/1996 |
| WO | WO 99/18442 A1 | 4/1999 |
| WO | WO 0035951 A1 * | 6/2000 |
| WO | WO 00/52476 | 9/2000 |
| WO | WO 01/16599 A1 | 3/2001 |
| WO | WO 01/42793 A2 | 6/2001 |
| WO | WO 01/42793 A3 | 6/2001 |
| WO | WO 01/88086 | 11/2001 |
| WO | WO 02/23191 | 3/2002 |
| WO | WO 02/23191 A1 | 3/2002 |
| WO | WO 02/059822 | 8/2002 |
| WO | WO 02/083913 | 10/2002 |
| WO | WO 02/089657 | 11/2002 |
| WO | WO 03/016910 | 2/2003 |
| WO | WO 2004/058055 A2 | 7/2004 |
| WO | WO 2004/059293 A2 | 7/2004 |
| WO | WO 2004/094460 A2 | 11/2004 |
| WO | WO 2005/029088 A2 | 3/2005 |
| WO | WO 2005/029088 A3 | 3/2005 |

OTHER PUBLICATIONS

Takahashi et al., "Serum levels of surfactant proteins A and D are useful biomarkers for interstitial lung disease in patients with progresive systemic sclerosis," Am. J. Respir. Crit. Care Med., 2000, vol. 162, pp. 258-263.*

Tulevski et al., "Utility of a BNP as a marker for RV dysfunction in acute pulmonary embolism," J. Am. College of Cardiol., 2002, vol. 39, pp. 2080-2081.*

Aggarwal et al., "Evaluation of serum lipid profile and cardiac enzyme changes in cerebrovascular accidents," *JIMA*, 93:331-332 (1995).

Akiyama et al., "Changes in serum concentrations of matrix metalloproteins, tissue inhibitors of metallo proteinases and Type IV collagen in patients with various types of glomerulonephritis," *Res. Commun. In Mol. Path. and Pharm.*, 95(2): 115-128 (1997).

Albrechtsen, M. and Bock, E. J., Quantification of Glial Fibrillary Acidic Protein (GFAP) in Human Body Fluids by means of ELISAEmploying a Monoclonal Antibody, *Neuroimmunol.* 8:301-309 (1985).

Amaro, A. et al., "Plasma leukocyte elastase concentration in angiographically diagnosed coronary artery disease," *Eur. Heart J.* 16:615-622 (1995).

Ardissino, D. et al., "Tissue-factor antigen and activity inhuman coronary atherosclerotic plaques," *Lancet* 349:769-771 (1997).

Asano, Y. et al., "Clinical Significance of surfactant protein D as a serum marker of evaluating pulmonary fibrosis in patients with systemic sclerosis," *Arthritis Rheum* 44(6):1363-9 (Jun. 2001).

Austgulen et al., "Increased maternal plasma levels of soluble adhesion molecules (ICAM-1, VCAM-1, E-selectin) in preeclampsia," *Eur. J. Obstet. Gynecol. Reprod. Biol.*, 71:53-58 (1997).

Badr-elDin et al., "Eosinophil cationic protein as a serological marker of disease activity in childhood bronchial asthma," *East Mediterr. Health J.* 5:664-75 (1999).

Baker, T. et al., "Serum metalloproteinases and their inhibitors: markers for malignat potential," *Br. J. Cancer* 70:506-512 (1994).

Balagopalakrishna, C. et al., Modification of low density lipoproteins by erythrocytes and hemoglobin under hypoxic conditions, *Adv. Exp. Med. Biol.* 411:337-345 (1997).

Bandoh et al., "Sequential changes of KL-6 in sera of patients with interstitial pneumonia associated with polymyositis/dermatomyositis," *Ann. Rheum. Dis.* 59:257-62 (2000).

Banks et al., "Circulating intercellular adhesion molecule-1 (ICAM-1), E-selectin and vascular cell adhesion molecule-1 (VCAM-1) in human malignancies," *Br. J. Cancer* 68:122-124 (1993).

Bates et al., "Neurotrophin-3 promotes cell death induced in cerebral ischemia, oxygen-glucose deprivation, and oxidative stress: possible involvement of oxygen free radicals," *Neurobiology of Disease* 9: 24-37 (2002).

Bayes-Genis, A. et al., "Elevated levels of plasmin-α2 antiplasmin complexes in unstable angina," *Thromb. Haemost.* 81:865-68 (1999).

Bazzan, M. et al., "No evidence of platelet activation during atrial pacing in subjects with stable angina," *Cardiologia* 34:217-220 (1989).

Benamer et al., "Comparison of the prognostic value of C-reactive protein and troponin I in patients with unstable angina pectoris," *Am. J. Cardiol.*, 82:845-850 (1998).

Bertinchant, J.P. et al., "Release kinetics of serum cardiac troponin I in ischemic myocardial injury," *Clin. Biochem.* 29:587-594 (1996).

Bialik et al., "Myocyte apoptosis during acute myocardinal infarction in the mouse localizes to hypoxic regions but occurs independently of p53," *J. Clin. Invest.* 100(6): 1363-1372 (1997).

Biasucci et al., "Episodic activation of the coagulation system in unstable angina does not elicit an acute phase reaction," *Am. J. of Cardiol.* 77:85-87 (1996).

Biasucci, L.M. et al., "Temporal relation between ischemic episodes and activation of the coagulation system in unstable angina," *Circulation* 93:2121-2127 (1996).

Biasucci et al., "Elevated levels of interleukin-6 in unstable angina," *Circulation* 94:874-877 (1996).

Biasucci et al., "Increasing levels of interleukin (IL)-1Ra and IL-6 during the first 2 days of hospitalization in unstable angina are associated with increased risk of in-hospital coronary events," *Circulation* 99:2079-2084 (1999).

Bitsch et al., "A longitudinal prospective study of soluble adhesion molecules in acute stroke," *Stroke*, 29:2129-2135 (1998).

Blankaert et al., "Constitutive release of metalloproteinase-9 (92-kd Type IV collagenase) by Kaposi's sarcoma cells," *J. Acquir. Immune Defic. Syndr. Hum. Retrovirol.* 18:203-209 (1998).

Blann et al., "Soluble intercellular adhesion molecule-1, E-selectin, vascular cell adhesion molecule-1 and von Willebrand factor in stroke," *Blood Coagul. Fibrinolysis* 10:277-284 (1999).

Blann, A.D. et al., "Evidence of platelet activation in hypertension," J. Hum. Hypertens. 11:607-609 (1997).

Blann, A.D. et al., "Soluble P-selectin in atherosclerosis: a comparison with endothelial cell and platelet markers," Thromb. Haemost. 77:1077-1080 (1997).

Bonfrer et al., "The luminescence immunoassay S-100: a sensitive test to measure circulating S-100B: its prognostic value in malignant melanoma," *Brit. Jour. Of Cancer* 77(12): 2210-2214 (1998).

Bollensen et al., "Adenylate kinase enzyme activity in cases of brain infarction," *Acta Neural. Scand.* 79:53-58 (1989).

Bonomini, M. et al., "Serum levels of soluble adhesion molecules in chronic renal failure and dialysis patients," *Nephron* 79:399-407 (1998).

Bonow, "New insights into the cardiac natriuretic peptides," *Circulation* 93:1946-1950 (1996).

Bossnik et al., "Plasma levels of the chemokines monocyte chemotactic proteins-1 and -2 are elevated in human sepsis," *Blood* 86(10): 3841-3847 (1995).

Bousquet et al., "Eosinophilic inflammation in asthma," *New Engl. J Med.* 323:1033-9 (1990).

Bowen-Pope, D.F. et al., "Platelet-derived growth factor in vivo: levels, activity, and rate of clearance," *Blood* 64:458-469 (1984).

Brooks and Ergul, "Identification of amino acid residues in the C-terminal tail of big endothelin-1 involved in processing to endothelin-1," *J. Mol. Endocrinol.* 21:307-15 (1998).

Brown, D.L. et al., "Identification of 92-kd gelatinase in human coronary atherosclerotic lesions," *Circulation* 91:2125-2131 (1995).

Caligiuri et al., "Immune system activation follows inflammation in unstable angina: pathogenetic implications," *J.Am. Coll. Cardiol.* 32:1295-1304 (1998).

Carlstedt et al., "Proinflammatory cytokines, measured in a mixed population on arrival in the emergency department, are related to mortality and severity of disease," *Journal of Internal Medicine* 242:361-365 (1997).

Carraro, U. and Franceschi, C., "Apoptosis of skeletal and cardiac muscles and physical exercise," *Aging* (Milano) 9:19-34 (1997).

Carter et al., "Platelet GP IIIa P1A and GP Ib variable number tandem repeat polymorphisms and markers of platelet activation in acute stroke," *Arterioscler. Thromb. Vasc.* 18:1124-1131 (1998).

Carter et al., "Purification, cloning, expression and biological characterization of an interleukin-1 receptor antagonist protein," *Nature* 344:633-638 (1990).

Carville, D.G. et al., "Thrombus precursor protein (TpP™): marker of thrombosis early in the pathogenesis of myocardial infarction," *Clin. Chem.* 42:1537-1541 (1996).

Catto et al., "von Willebrand factor and factor VIII: C in acute cerebrovascular disease," *Thromb. Haemost.* 77:1104-8 (1997).

Chong, B.H. et al., "Plasma P-selectin is increased in thrombotic consumptive platelet disorders," *Blood* 83:1535-1541 (1994).

Colucciello, S.A., *EMR Texbook*, pp. 1-23 http://www.thrombosis-consult.com/articles/Texbook/54_pulmonary, printed Nov. 4, 2002.

Cohen, A.M. et al., "Plasma clearance and tissue distribution of recombinant human platelet-derived growth factor (B-chain homodimer) in rats," *J. Surg. Res.* 49:447-452 (1990).

Crouch, "Surfactant protein-D and pulmonary host defense," *Respir. Res.* 1: 93-108 (2000).

Curzen et al., "Can C reactive protein or troponins T and I predict outcome in patients with intractable unstable angina?" *Heart* 80:23-27 (1998).

D'Astou, M., "Diastolic Heart Failure," *Persp. In Cardiology* pp. 30-37 (May 2002).

Dangas et al., "Correlation of serum lipoprotein(a) with the angiographic and clinical presentation of coronary artery disease," *Am. J. Cardiol.* 83:583-585 (1999).

Dao et al., "Utility of B-Type Natriuretic Peptide in the Diagnosisof Congestive Heart Failure in an Urgent-Care Setting," *J. Am. Coll. Cardiol.* 37:379-85 (2001).

Davi, G. et al., "Increased levels of soluble P-selectin in hypercholesterolemic patients," *Circulation* 97:953-957 (1998).

Davidson et al., "C-type natriuretic peptide," *Circulation* 93:1155-9 (1996).

Davie et al., "The coagulation cascade: initiation, maintenance and regulation," *Biochemistry* 30(43): 10363-10370 (1991).

De Caterina, R. et al., "Platelet activation in angina at rest. Evidence by paired measurement of plasma beta-thromboglobulin and platelet factor 4*," *Eur. Heart J.* 9:913-922 (1988).

De Rose et al., "Circulating adhesion molecules in cystic fibrosis," *Am. J. Respir. Crit. Care. Med.* 157: 1234-1239 (1998).

Depre, C. et al., "Expression of inducible nitric oxide synthase in human coronary atherosclerotic plaque," *Cardiovasc. Res.* 41:465-472 (1999).

Diller, M.P. et al., "Congestive Heart Failure Due to Diastolic or Systolic Dysfunction," *Arch Fam Med.* 8:414-420 (1999).

Dinerman, J.L. et al., "Incrreased neutrophil elastase release in unstable angina pectoris and acute myocardial infarction," *J. Am. Coll. Cardiol.* 15:1559-1563 (1990).

Doubell, A.F. et al., "Identification and immunolocalisation of annexins V and VI, the major cardiac annexins, in rat heart," *Cardiovasc. Res.* 27:1359-1367 (1993).

Dunlop, L.C. et al., "Characterization of GMP-140 (P-selectin) as a circulating plasma protein," *J. Exp. Med.* 175:1147-1150 (1992).

Durany, N. and Carreras, J., "Distribution of phosphyglycerate mutase isozymesin rat, rabbit and human tissues," *Comp. Biochem. Physiol. B. Biochem. Mol. Biol.* 114B:217-223 (1996).

Egermayer et al., "Usefulness of D-dimer, blood gas, and respiratory rate measurements for excluding pulmonary embolism," *Thorax* 53:830-34 (1998).

Eisenberg et al., "Interleukin 1 receptor antagonist is a member of the interleukin 1 gene family: evolution of a cytokine control mechanism," *Proc. Nat. Acad. Sci. USA*, 88: 5232-5236 (1991).

Emsley et al., "Crystal structure of the von Willebrand factor A1 domain and implications for the binding of platelet glycoprotein lb," *Journal of Biological Chemistry* 273(17): 10396-10401, (1998).

Endo et al., "Elevated levels of serum and plasma metalloproteinases in patients with gastric cancer," *Anticancer Research* 17:2253-2258 (1997).

Endo, S. et al., "Plasma interleukin 8 and polymorphonuclear leukocyte elastase concentrations in patients with septic shock," *J. Inflamm.* 45:136-142 (1995).

Eriksson, S. et al., "Leucocyte elastase as a marker in the diagnosis of acute appendicitis," *Eur. J. Surg.* 161:901-905 (1995).

Ertenli, I. et al., "P-selectin as a circulating molecular marker in rheumatoid arthritis with thrombocytosis," *J. Rheumatol.* 25:1054-1058 (1998).

Estrada et al., "High plasma levels of endothelin-1 and atrial natriuretic peptide in patients with acute ischemic stroke," *Am. J. of Hypertension* 7(12):1085-1089 (1994).

Falciani, M. et al., "Elevated tissue factor and tissue factor pathway inhibitor circulating levels in schaemic heart disease patients," *Thromb. Haemost.* 79:495-499 (1998).

Feinberg et al., "Hemostatic markers in acute ischemic stroke," *Stroke* 27:1296-1300 (1996).

Portales et al., "Utility of the serum biochemical markers CPK, CPK MB mass, myoglobin, and cardiac troponin T in a chest pain unit," *Rev. Esp. Cardio.* 55(9):913-20 (Sep. 2002).

Fernandes-Alnemri et al., "CPP32, a novel human apoptotic protein with homology to *Caenorhabditis elegans* cell death protein Ced-3 and mammalian interleukin-1β-converting enzyme," *Journal of Biological Chemistry* 269(49): 30761-30764 (1994).

Fisher et al., "Serum concentrations and peripheral secretion of the beta chemokines monocyte chemoattractant protein 1 and macrophage inflammatory protein 1α in alcoholic liver disease," *Gut* 45(3):416-420 (1999).

Fon et al., "Hemostatic markers in acute transient ischemic attacks," *Stroke* 25(2): 282-286 (1994).

Forssmann et al., "The endocrine heart and natriuretic peptides: histochemistry, cell biology, and functional aspects of the renal urodilatin system," *Histochem Cell Biol* 110: 335-357 (1998).

Fox, J.E., "Shedding of adhesion receptors from the surface of activated platelets," *Blood Coagul. Fibrinolysis* 5:291-304 (1994).

Fransen, E.J. et al., Evaluation of "new" cardiac markers for ruling out myocardial infarction *Chest* 122(4):1316-21 (Oct. 2002).

Frijns, C.J. et al., "Soluble adhesion molecules reflect endothelial cell activation in ischemic stroke and in carotid atherosclerosis," *Stroke* 28:2214-2218 (1997).

Fujii et al., "Hemostasis in spontaneous subarachnoid hemorrhage," *Neurosurgery* 37(2): 226-234 (1995).

Fujii et al., "Serial changes of hemostasis in aneurysmal subarachnoid hemorrhage with special reference to delayed ischemic neurological deficits," *J. Neurosurg.* 86:594-602 (1997).

Gaasch, W.H., Diagnosis and treatment of heart failure based on left ventricular systolic or diastolic dysfunction, *JAMA* 271:1276-80 (1994).

Gabay et al., "Interleukin 1 receptor antagonist (IL-1Ra) is an acute-phase protein," *J. Clin. Invest.* 99(12): 2930-2940 (1997).

Gallino, A. et al., "Fibrin formation and platelet aggregation in patients with acute myocardial infarction: effects of intravenous and subcutaneous low-dose heparin," *Am. Heart J.* 112:285-290 (1986).

Gamble, J.R. et al., "Prevention of activated neutrophil adhesion to endothelium by soluble adhesion protein," *Science* 249:414-417 (1990).

Gando, S. et al., "Increased neutrophil elastase, persistent intravascular coagulation, and decreased fibrinolytic activity in patients with posttraumatic acute respiratory distress syndrome," *J. Trauma* 42:1068-1072 (1997).

Garbisa, S. et al., "Correlation of serum metalloproteinase levels with lung cancer metastasis and response to therapy," *Cancer Res.* 52:4548-4549 (1992).

Genereau, T. et al., "Human neutrophil elastase in temporal (Giant Cell) arteritis: plasma and immunohistochemical studies," *J. Rheumatol.* 25:710-713 (1998).

Gensini, G.F. et al., "Increased protein C and fibrinopeptide: a concentration in patients with angina," *Thromb. Res.* 50:517-525 (1988).

George et al., "Evidence for altered hepatic matrix degradation in genetic haemochromatosis," *Gut* 42: 715-720 (1998).

Ghaisas, N.K. et al., "Elevated levels of circulating soluble adhesion molecules in peripheral blood of patients with unstable angina," *Am. J. Cardiol.* 80:617-619 (1997).

Ghanem, H. et al., "Increased low density lipoprotein oxidation in stable kidney transplant recipients," *Kidney Int.* 49:488-493 (1996).

Giambanco, I. et al., "Immunohistochemical localization of annexin V (CaBP33) in rat organs," *J. Histochem. Cytochem.* 39:p. 1189-1198 (1991).

Glatz, J.F. et al., "Fatty-acid-binding protein as a plasma marker for the estimation of myocardial infarct size in humans," *Br. Heart J.* 71:135-140 (1994).

Gleeson, M. et al., "The effect of severe eccentric exercise-induced muscle damage on plasma elastase, glutamine and zinc concentrations," *Eur. J. Appl. Physiol.* 77:543-546 (1998).

Gogos et al., "Pro-versus anti-inflammatory cytokine profile in patients with severe sepsis: a marker for prognosis and future therapeutic options," *J. Infect. Dis.* 181:176-80 (2000).

Gohji et al., "Elevation of serum levels of matrix metalloproteinase-2 and -3 as new predictors of recurrence in patients with urothelial carcinoma," *Cancer* 78(11):2379-2387 (Dec. 1, 1996).

Goldhaber, S.Z., "Modern treatment of pulmonary embolism," *Eur. Respir. J. Suppl.* 35:22s-27s (2002).

Goto et al., "Enhanced shear-induced platelet aggregation in acute myocardial infarction," *Circulation* 99:608-613 (1999).

Grisolia, S. et al., Influence of size, protein concentration, protein synthesis inhibitors, and carbon on clearance of enzymes and proteins from blood, *Physiol. Chem. Phys.* 8:37-52 (1976).

Gruber, B.L. et al., "Markedly elevated serum MMP-9 (Gelatinase B) levels in rheumatoid arthritis: a potentially useful laboratory marker," *Clin. Immunol. Immunopathol.* 78:161-171 (1996).

Gurfinkel, E. et al., "Importance of thrombosis and thrombolysis in silent ischaemia: comparison of patients with acute myocardial infarction and unstable angina," *Br. Heart J.* 71:151-55 (1994).

Hammer-Lercher et al., "Head-to-head comparison of N-terminal pro-brain natriuretic peptide, brain natriuretic peptideand N-terminal pro-atrial natriuretic peptide in diagnosis left ventricular dysfunction," *Clin. Chim. Acta* 310(2):193-7 (2001).

Hammerman, S.I. at al., "Endothelial cell nitric oxide production in acute chest syndrome," *Am. J. Physiol.* 277:H1579-H1592 (1999).

Hanley and McNeil, "The meaning and use of the area under a receiver operating characteristic (ROC) curve," *Radiology* 143:29-36 (1982).

Harris, "Emergency management of acute asthma," Aust. Fam. Physician 31:802-06 (2002).

Hasegawa, S. et al., "S100$a_0$ protein as a marker for tissue damage related to extracorporeal shock wave lithotripsy," *Eur. Urol.* 24:393-396 (1993).

Hasegawa et al., "Increased levels of calbindin-D in serum and urine from patients treated by extracorporeal shock wave lithotripsy," *Journal of Urology* 149:1414-1418 (1993).

Hayasaka et al., "Elevated plasma levels of matrix metalloproteinase-9 (92-kd type IV collagenase/gelatinase B) in hepatocellular carcinoma," *Hepatology* 24:1058-1062 (1996).

Haznedaroglu, I.C. et al., "Selectins and IL-6 during the clinical course of idiopathic thrombocytopenic purpura," *Acta Haematol.* 101:16-20 (1999).

Herraez-Dominguez, M.V. et al., "Immunological determination of muscle-type enolase in the serum as a diagnostic test for myocardial infarction," *Clin. Chim. Acta* 64:307-315 (1975).

Hirashima et al., "Cerebrospinal fluid tissue factor and thrombin-antithrombin III complex as indicators of tissue injury after subarachnoid hemorrhage," *Stroke* 28:1666-1670 (1997).

Hirashima et al., "Elevation of platelet activating factor, inflammatory cytokines, and coagulation factors in the internal jugular vein of patients with subarachnoid hemorrhage," *Neurochem. Res.* 22: 1249-1255 (1997).

Hoffmeister, H.M. et al., "Alterations of coagulation and fibrinolytic and kallibrein-kinin systems in the acute and postacute phases in patients with unstable angina pectoris," *Circulation* 91:2520-27 (1995).

Hoffmeister, H.M. et al., "Correlation between coronary morphology and molecular markers of fibrinolysis in unstable angina pectoris," *Atherosclerosis* 144:151-157 (1999).

Hollander, J.E. et al., "Risk stratification of emergency department patients with acute coronary syndromes using P-selectin," *J. Am. Coll. Cardiol.* 34:95-105 (1999).

Holvoet, P. et al., "Malondialdehyde-modified LDL as a marker of acute coronary syndromes," *JAMA* 281:1718-21 (1999).

Holvoet, P., "Oxidative modification of low-density lipoproteins in atherothrombosis," *Acta Cardiol.* 53:253-260 (1998).

Holvoet, P. et al., "Oxidized LDL and malondialdehyde-modified LDL in patients with acute coronary syndromes and stable coronary artery disease," *Circulation* 98:1487-94 (1998).

Hunt et al., "The amino-terminal portion of Pro-brain natriuretic peptide (pro-BNP) circulates in human plasma," *Biochem. Biophys. Res. Commun.* 214:1175-1183 (1995).

Iiyama, K. et al., "Patterns of vascular cell adhesion molecule-1 and intercellular adhesion molecule-1 expression in rabbit and mouse atherosclerotic lesions and at sites predisposed to lesion formation," *Circ. Res.* 85:199-207 (1999).

Iizasa, T. et al., "Elevated levels of circulating plasma matrix metalloproteinase 9 in non-small cell lung cancer patients," *Clin. Cancer Res.* 5:149-153 (1999).

Ikeda, H. et al., "Increased soluble form of P-selectin in patients with unstable angina," *Circulation* 92:1693-1696 (1995).

Ikeda, H. et al., "Soluble form of P-selectin in patients with acute myocardial infarction," *Coron. Artery Dis.* 5:515-518 (1994).

Isgro et al., "A predictive parameter in patients with brain related complications after cardiac surgery," *Eur. J. Cardiothorac. Surg.* 11:640-644 (1997).

Ishii, J. et al., "Serum concentrations of myoglobin vs human heart-type cytoplasmic fatty acid-binding protein in early detection of acute myocardial infarction," *Clin. Chem.* 43:1372-1378 (1997).

Jacque et al., "Myelin basic protein in CSF and blood," Arch. Neurol.. 39: 557-560, 1982.

James, T., "The variable morphological coexistence of apoptosis and necrosis in human myocardial infarction: significance for understanding its pathogenesis, clinical course, diagnosis and prognosis," *Coron. Artery Dis.* 9:291-307 (1998).

Janoff, A., "Elastase in tissue injury," *Annu Rev Med* 36:207-216 (1985).

Jensen et al., Characterization of human brain S100 protein fraction: amino acid sequence of S100β, *J. Neurochem.* 45:700-705 (1985).

Jimenez, W. et al., "Nitric oxide production and inducible nitric oxide synthase expression in peritoneal macrophages of cirrhotic patients," *Hepatology* 30:670-676 (1999).

Johnson et al., "Activation of matrix-degrading metalloproteinases by mast cell proteases in atherosclerotic plaques," *Arterioscler. Thromb. Vasc. Biol.* 18:1707-1715 (1998).

Johnsson et al., "Markers of cerebral ischemia after cardiac surgery," *J. Cardiothorac. Vasc. Anesth.* 10: 120-126 (1996).

Johnston, G.I. et al., "Structure of the human gene encoding granule membrane protein-140, a member of the selectin family of adhesion receptors for leukocytes," *J. Biol. Chem.* 265:21381-21385 (1990).

Kai, H. et al., "Peripheral blood levels of matrix metalloproteases-2 and -9 are elevated in patients with acute coronary syndromes," *J. Am. Coll. Cardiol.* 32:368-372 (1998).

Kaikita, K. et al., "Soluble P-selectin is released into the coronary circulation after coronary spasm," *Circulation* 92:1726-1730 (1995).

Kaikita, K. et al., "Tissue factor expression on macrophages in coronary plaques in patients with unstable angina," *Arterioscler. Thromb. Vasc. Biol.* 17:2232-2237 (1997).

Kaneko et al., "Circulating levels of β-chemokines in systemis lupus erythematosus," *J. Rheumatol.*, 26:568-573 (1999).

Kaneko, N. et al., "Measurement of plasma annexin V by ELISA in the early detection of acute myocardial infarction," *Clin. Chim. Acta* 251:65-80 (1996).

Katayama, M. et al., "Soluble P-selectin is present in normal circulation and its plasma level is elevated in patients with thrombotic thrombocytopenic purpura and haemolytic uraemic syndrome," *Br. J. Haematol.* 84:702-710 (1993).

Kato, K. et al., "Immunoassay of human muscle enolase subunit in serum: a novel marker antigen for muscle diseases," *Clin. Chim. Acta* 131:75-85 (1983).

Kato, K. and Kimura, "S100a$_0$(αα) protein is mainly located in the heart and striated muscles," S., *Biochim. Biophys. Acta* 842:146-150 (1985).

Kaye, D.M. et al., "The failing human heart does not release nitrogen oxides," *Life Sci.* 62:883-887 (1998).

Keyszer et al., "Circulating levels of matrix metalloproteinases MMP-3 and MMP-1, tissue inhibitor of metalloproteinases 1 (TIMP-1), and MMP-1/TIMP-1 complex in rheumatic disease. Correlation with clinical activity of rheumatoid arthritis versus other surrogate markers," *J. Rheumatol.*, 26:251-258 (1999).

Keyszer, G. et al., "Matrix metalloproteinases, but not cathepsisn B, H, and L or their inhibitors in peripheral blood of patients with rheumatoid arthritis are potentially useful markers of disease activity," *Z Rheumatol.* 57:392-398 (1998).

Kienast, J. et al., "Prothrombin activation fragment 1+2 and thrombin antithrombin III complexes in patients with angina pectoris: relation to the presence and severity of coronary atherosclerosis," *Thromb. Haemost.* 70:550-553 (1993).

Kikuchi, T. et al., "Clinical evaluation of serum S100$_{ao}$ protein in patients with urogenital diseases and healthy volunteers,"*Hinyokika Kiyo* 36:1117-1123 (1990).

Kim et al., "Cytokines and adhesion molecules in stroke and related diseases," *J. Neurol. Sci.*, 137:69-78 (1996).

Kohno, "Serum marker KL-6/MUC1 for the diagnosis and management of interstital pneumonits," *J. Med. Invest.* 46:151-58 (1999).

Koller et al., "Clinical value of monitoring eosinophil activity in asthma," *Arch. Dis. Childhood* 73:413-7 (1995).

Konstantinides S. et al., "Importance of cardiac troponins I and T in risk stratification of patients with acute pulmonary embolism," *Circulation* 106(10):1263-8 (Sep. 2002).

Kosar, F. et al., "Plasma leukocyte elastase concentration and coronary artery disease," *Angiology* 49:193-201 (1998).

Koukkunen, H. et al., "Troponin T and creatinine kinase isoenzyme MB mass in the diagnosis of myocardial infarction," *Ann. Med.* 30:488-496 (1998).

Koyama et al., "Determination of plasma tissue factor antigen and its clinical significance," *Br. J. Haematol.*, 87:343-347 (1994).

Krause, E.G. et al., "Glycogen phosphorylase isoenzyme BB in diagnosis of myocardial ischaemic injury and infarction," *Mol. Cell Biochem.* 160-161:289-295 (1996).

Krishnaswamy et al., "Utility of B-natriuretic peptide levels in identifying patients with left ventricular systolic or diastolic dysfunction," *Am. J. Med.* 111:274-79 (2001).

Kruip, M.J. et al., "Use of a clinical decision rule in combination with D-diner concentration in diagnostic workup of patients with suspected pulmonary embolism," *Arch Intern Med* 162(14):1631-5 (Jul. 22, 2002).

Krupinski, J. et al., "Protein kinase C expression and activity in the human brain after ischaemic stroke," *Acta Neurobiol. Exp.* (Warz) 58:13-21 (1998).

Kruskal, J.B. et al., "Fibrin and fibrinogen-related antigens in patients with stable and unstable coronary artery disease," *N. Engl. J. Med.* 317: 1361-65 (1987).

Kudo, S. et al., "Clearance and tissue distribution of recombinant human interleukin 1β in rats," *Cancer Res.* 50:5751-5755 (1990).

Kurimoto, M. et al., "Plasma platelet-derived growth factor-B chain is elevated in patients with extensively large brain tumour," *Acta Neurochir.* (Wien) 137:182-187 (1995).

Kuwasako et al., "Increased plasma proadrenomedullin N-terminal 20 peptide in patients with essential hypertension," *Ann. Clin. Biochem.* 36:622-628 (1999).

Lai, R.S. et al., "Evaluation of cytokeratin 19 fragment (CYFRA 21-1) as a tumor marker in malignant pleural effusion," *Jpn J Clin Oncol* 29(9):421-4 (Sep. 1999).

Landi et al., "Hypercoagulability in acute stroke: Prognostic significance," *Neurol.*, 37:1667-1671 (1987).

Laskowitz et al., "Serum markers of cerebral ischemia," *J. Stroke Cerebrovasc. Dis.*, 7:234-241 (1998).

Latini et al., "Cytokines in acute myocardial infarction: selective increase in circulating tumor necrosis factor, its soluble receptor, and interleukin-1 receptor antagonist," J.Cardiovasc. Pharmacol., 23:1-6 (1994).

Laurino J.P. et al., "Thrombus precursor protein™ and the measurement of thrombosis inpatients with acute chest pain syndrome," *Ann. Clin. Lab. Sci.* 27:338-345 (1997).

Lee et al., "Insulin-like growth factors and cerebral ischemia," *Ann. N.Y. Acad. Sci.* 679:418-422 (1993).

Lee et al., "Proteolytic processing of big endothelin-3 by the kell blood group protein," *Blood* 94:1440-50 (1999).

Lein et al., "Metalloproteinasen (MMP-1, MMP-3) and ihre inhibitoren (TIMP) im blutplasma bei patienten mit prostatakarzinom," *Urologe [A]* 37:377-381 (1998).

Li, D. et al., "Acute ischemic heart disease," *Am. Heart J.* 137:1145-1152 (1999).

Li et al., "The expression of monocyte chemotactic protein (MCP-1) in human vascular endothelium in vitro and in vivo," *Mol. Cell. Biochem.* 126:61-68 (1993).

Ling, W. et al., "Oxidized or acetylated low density lipoproteins are rapidly cleared by the liver in mice with disruption of the scavenger receptor class A type I/II gene," *J. Clin. Invest.* 100:244-252 (1997).

Liras, G. et al., "Clinical value of an automated granulocyte elastase assay in predicting severity of acute pancreatitis," *Rev. Esp. Enferm. Dig.* 87:647-652 (1995).

Liu et al., "Purification and characterization of an interleukin-1β-converting enzyme family protease that activates cysteine protease P32 (CPP32)," *J. Biol. Chem.* 271:13371-13376 (1996).

Liuzzo et al., "Plasma protein acute-phase response in unstable angina is not induced by ischemic injury," *Circulation* 94:2373-2380 (1996).

Livrea, M.A. et al., "Oxidative modification of low-density lipoprotein and atherogenetic risk in β-thalassemia," *Blood* 92:3936-3942 (1998).

Long et al., "p53 and the hypoxia-induced apoptosis of cultured neonatal rat cardiac myocytes," *J. Clin. Invest.* 99:2635-2643 (1997).

Lundergan et al., "Clinical investigations: acute ischemic heart disease," *Am. Heart J.* 144:456-62 (2002).

MacManus, J.P. et al., "Cerebral Ischemia produces laddered DNA fragments distinct from cardiac ischemia & Archetypal apoptosis," *J. Cereb. Blood Flow Metab.* 19:502-510 (1999).

Mahadevan, D. et al., "Structural role of extracellular domain 1 of α-platelet-derived growth factor (PDGF) receptorfor PDGF-AA and PDGF-BB binding," *J. Biol. Chem.* 270:27595-27600 (1995).

Mair, J. et al., "Early release of glycogen phosphorylase in patients with unstable angina and transiet ST-T alterations," *Br. Heart J.* 72:125-127 (1994).

Mair, J., "Glycogen phosphorylase isoenzyme BB to diagnose ischaemicmyocardial damage," *Clin. Chim. Acta* 272:79-86 (1998).

Mair, J., "Progress in myocardial damage detection: new biochemical markers for clinicians," *Crit. Rev. Clin. Lab. Sci.* 34:1-66 (1997).

Mair, P. et al., "Glycogen phosphorylase isoenzyme BB mass releaseafter coronary artery bypass grafting," *Eur. J. Clin. Chem. Clin. Biochem.* 32:543-547 (1994).

Maiuri et al., "Serum and cerebrospinal fluid enzymes in subarachnoid haemorrhage," Neurol. Res., 11:6-8 (1989).

Mallamaci, F. et al., "Diagnostic value of troponin T for alterations in left ventricular mass and function in dialysis patients," *Kidney Int.* 62(5):1884-1890 (Nov. 2002).

Manicourt et al., "Serum levels of collagenase, stromelysin-1, and TIMP-1," Arthritis Rheum., 37:1774-1783 (1994).

Manten, A. et al., "Procoagulant and proinflammatory activity in acute coronary syndromes," *Cardiovasc. Res.* 40:389-395 (1998).

Martens et al., "Serum S-100 and neuron-specific enolase for prediction of regaining consciousness after global cerebral ischemia," Stroke, 29: 2363-2366 (1998).

Matsuda, H. et al., "A sandwich enzyme immunoassay for human muscle-specific β-enolase and its application for the determination of skeletal muscle injury," *Forensic Sci. Int.* 99:197-208 (1999).

Matsumori et al., "Plasma levels of the monocyte cnemotactic and activating factor/monocyte chemoattractant protein-1 are elevated in patients with acute myocardial infarction," J. Mol. Cell. Cardiol., 29:419-423 (1997).

Mehta, J. et al., "Neutrophil function in ischemic heart disease," *Circulation* 79:549-556 (1989).

Merlini, P.A. et al., "Persistent activation of coagulation mechanism in unstable angina and myocardial infarction," *Circulation* 90:61-68 (1994).

Michelson, A.D. et al., "In vivo tracking of platelets: circulating degranulated platelets rapidly lose surface P-selectin but continue to circulate and function," *Proc. Natl. Acad. Sci. U S. A.* 93:11877-11882 (1996).

Missler et al., "S-100 protein and neuron-specific enolase concentrations in blood as indicators of infarction volume and prognosis in acute ischemic stroke," *Stroke* 28, 1956-1960 (1997).

Misumi, K. et al., "Comparison of plasma tissue factor levels in unstable and stable angina pectoris," *Am. J. Cardiol.* 81:22-26 (1998).

Miwa, K. et al., "Soluble E-selectin, ICAM-1 and VCAM-1 levels in systemic and coronary circulation in patients with variant angina," *Cardiovasc. Res.* 36:37-44 (1997).

Miyata et al., "Conformational changes in the A1 domain of von Willebrand factor modulating the interaction with platelet glycoprotein Ibα," *J. Biol. Chem.* 271:9046-9053 (1996).

Montalescot et al., "Early increase of von Willebrand factor predicts adverse outcome in unstable coronary artery disease," *Circulation* 98:294-299 (1998).

Moore et al., "Collagenase expression in ovarian cancer cell lines," *Gynecol. Oncol.* 65:78-82 (1997).

Mooser, V. et al., "Effect of cardiopulmonary bypass and heparin on plasma levels of Lp(a) and Apo(a) fragments," *Arterioscler. Thromb. Vasc. Biol.* 19:1060-1065 (1999).

Morgan and Hodge, "Diagnostic evaluation of dyspnea," *Am. Fam. Physician* 57:711-16 (1998).

Morita, T. et al., "Evaluation of serum S100ao protein in patients with renal cell carcinoma," *Nippon Hinyokika Gakkai Zasshi* 81:1162-1167 (1990).

Mowla et al., "Biosynthesis and post-translational processing of the precursor to brain-derived neurotrophic factor," *J.Biol. Chem.* 276: 12660-12666 (2001).

Mulrow et al., "Discriminating causes of dyspnea through clinical examination," *J. Gen. Int. Med.* 8:383-92 (1993).

Mulvihill, N. et al., "Early temporal expression of soluble cellular adhesion molecules in patients with unstable angina and subendocardial myocardial infarction," *Am. J. Cardiol.* 83:1265-7, A9 (1999).

Mun-Bryce et al., "Matrix metalloproteinases in cerebrovascular disease," *J. Cereb. Blood Flow Metab.* 18:1163-1172 (1998).

Murawaki, Y. et al., "Serum matrix metalloproteinase-1 in patients with chronic viral hepatitis," *J. Gastroenterol. Hepatol.* 14:138-145 (1999).

Murawaki, Y. et al., "Clinical usefulness of serum matrixmetalloproteinase-2 concentration in patients with chronic viral liver disease," *J. Hepatol.* 30:1090-1098 (1999).

Musso, P. et al., "Troponina I cardiaca E troponina T cardiaca nell'angina instabile: indicenza, correlazione, cinetica di rilasciamento e valore prognostico," *J. Ital. Cardiol.* 26:1013-23 (1996).

Nakamura, T. et al., "Modulation of plasma metalloproteinase-9 concentrations and peripheral blood monocyte mRNA levels inpatients with septic shock: effect of fiber-immobilized polymyxin B treatment," *Am. J. Med. Sci.* 316:355-360 (1998).

Ng and Ilag, Biomedical applications of protein chips, *J. Cell Mol. Med.* 6:329-340 (2002).

Ni, Z. et al., "Up-regulation of renal and vascular nitric oxide synthase in iron-deficiency anemia," *Kidney Int.* 52:195-201 (1997).

Niebroj-Dobosz, I., et al., "Immunochemical analysis of some proteins in cerebrospinal fluid and serum of patients with ischemic strokes," *Folia Neuropathol.* 32:129-137 (1994).

Nishiyama et al., "Simultaneous elevation of the levels of circulating monocyte chemoattractant protein-1 and tissue factor in acute coronary syndromes," *Jpn. Circ. J.* 62:710-712 (1998).

Nishizawa et al., "Protein kinase Cδ and α are invloved in the development of vasospasm after subarachnoid hemorrhage," *Eur. J. Pharmacol.* 398: 113-119 (2000).

Nomura, M. et al., "Serum β-enolase in acute myocardial infarction," *Br. Heart J.* 58:29-33 (1987).

Nomura, S. et al., "Effect of cilostazol on soluble adhesion molecules and platelet-derived microparticles in patients with diabetes," *Thromb. Haemost.* 80:388-392 (1998).

Norregaard-Hansen, K. et al., "Lack of indication of myocardial cell damage after myocardial ischaemia in patients with severe stable angina," *Eur. Heart J.* 13:188-193 (1992).

O'Connor, C.M. et al., "Usefulness of soluble and surface-bound P-selectin in detecting heightened platelet activity in patients with congestive heart failure," *Am. J. Cordial.* 83:1345-1349 (1999).

Ogawa, H. et al., "Plasma platelet-derived growth factor levels in coronary circulation in unstable angina pectoris," *Am. J. Cardiol.* 69:453-456 (1992).

Ogawa, H. et al., "Plasma soluble intercellular adhesion molecule-1 levels in coronary circulation in patients with unstable angina," *Am. J. Cardiol.* 83:38-42 (1999).

Ogawa, H. et al., "Platelet-derived growth factor is released into the coronary circulation after coronary spasm," *Coron. Artery Dis.* 4:437-442 (1993).

Ohtsuka et al., "Clinical implications of circulating soluble Fas and Fas ligand in patients with acute myocardial infarction," *Coron. Artery Dis.* 10:221-225 (1999).

Otsuki et al., "Circulating vascular cell adhesion molecule-1 (VCAM-1) in atherosclerotic NIDDM patients," *Diabetes* 46:2096-2101 (1997).

Paganuzzi, M. et al., "Diagnostic value of CYFRA 21-1 tumor marker and CEA in pleural effusion due to mesathelioma," *Chest* 119(4):1138-42 (2001).

Palfreyman, J.W. et al., "Radioimmunoassay of serum myelin basic protein and its application to patients with cerebrovascular accident," *Clin. Chim. Acta* 92:403-409 (1979).

Pellegatta, F. et al., "Soluble E-selectin and intercellular adhesion molecule-1 plasma levels increase during acutemyocardial infarction," *J. Cardiovasc. Pharmacol.* 30:455-460 (1997).

Persson et al., "S-100 protein and neuron-specific enolase in cerebrospinal fluid and serum: markers of cell damage in human central nervous system," *Stroke* 18:911-918 (1987).

Peter, K. et al., "Circulating vascular cell adhesion molecule-1 correlates with the extent of human atherosclerosis in contrast to circulating intercellular adhesion molecule-1, E-selectin, P-selectin, and thrombomodulin," *Arterioscler. Thromb. Vasc. Biol.* 17:505-512 (1997).

Pettila et al., "Predictive value of procalcitonin and interleukin 6 in critically ill patients with suspected sepsis," *Intensive Care Med.* 28:1220-25 (2002).

Plow, E.F., "Leukocyte elastate release during blood coagulation," *J. Clin. Invest.* 69:564-572 (1982).

Plow, E.F. and Plescia, J., "Neutrophil secretion during blood coagulation: evidence for a prekallikrein independent pathway," *Thromb. Haemost.* 59:360-363 (1988).

Polin et al., "Detection of soluble E-selectin, ICAM-1, VCAM-1, and L-selectin in the cerebrospinal fluid of patients after subarachnoid hemorrhage," *J. Neurosurg.* 89:559-567 (1998).

Prickett et al., "Identification of amino-terminal pro-C-type natriuretic peptide in human plasma," *Biochem. Biophys. Res. Commun.* 286:513-517 (2001).

Quinn et al., "Mapping of antigenic sites in human neuron-specific enolase by expression subcloning," *Clin. Chem.* 40: 790-795 (1994).

Rabitzsch, G. et al., "Immunoinhibition assay of the serum activity of human glycogen isophosphorylase BB in the diagnosis of the acutemyocardial ischaemia," *Biomed. Biochim. Acta* 46:S584-S588 (1987).

Rabitzsch, G. et al., "Immunoenzymometric assay of human glycogen phosphorylase isoenzyme BB in diagnosis of ischemic myocardial injury," *Clin. Chem.* 41:966-978 (1995).

Rabitzsch, G. et al., "Isoenzyme BB of glycogen phosphorylase b and myocardial infarction," *Lancet* 341:1032-1033 (1993).

Ray et al., "Predictive factors of tumor esponse and prognostic factors of survival during lung cancer chemotherapy," *Cancer Detect. Prev.* 22: 293-304 (1998).

Reeves, D., "Tryptase," *Immunology HAPS* (Jun. 1998).

Robey et al., "Binding of C-reactive protein to chromatin and nucleosome core particles," *J. Biol. Chem.* 259:7311-7316 (1984).

Romanic et al., "Matrix metalloproteinase expression increases after cerebral focal ischemia in rats," *Stroke* 29:1020-1030 (1998).

Rosenberg, "Matrix metalloproteinases in brain injury," *J. Neurotrauma* 12:833-842 (1995).

Rossi et al., "Natriuretic peptide levels in atrial fibrillation," *Journal of the American College of Cardiology* 35: 1256-62 (2000).

Rossi, E. et al., "Increased plasma levels of platelet-derived growth factor(PDGF-BB+PDGF-AB) in patients with never-treated mild essential hypertension," *Am. J. Hypertens.* 11:1239-1243 (1998).

Rubattu et al., "The gene encoding atrial natriuretic peptide and the risk of human stroke," *Circulation* 100:1722-1726 (1999).

Rucinski et al., "Clearance of human platelet factor 4 by liver and kidney: its alteration by heparin," *Am. J. Ohysiol.* 251: H800-H807 (1986).

Sagnella, G.A., "Measurement and significance of circulating natriuretic peptidesin cardiovascular disease," *Clinical Science* 95:519-29 (1998).

Sakamaki, F. et al., "Soluble form of P-selecting in plasma is elevatedin acute lung injury," *A. J. Respir. Crit. Care Med.* 151:1821-1826 (1995).

Sakata, K. et al., Characteristics of vasospastic angina with exercised-induced ischemia—analysis of parameters of hemostatis and fibrinolysis. *Jpn. Circ. J.* 60:277-284 (1996).

Saraste A., "Morphologic criteria and detection of apoptosis," *Herz.* 24:189-195 (1999).

Sasagawa, T. et al., "The significance of plasma lysophospholipids in patients with renal failure on hemodialysis," *J. Nutr. Sci. Vitaminol.* (Tokyo) 44:809-818 (1998).

Sawicki, G. et al., "Localization and translocation of MMP-2 during aggregation of human platelets," *Thromb. Haemost.* 80:836-839 (1998).

Schabiltz et al., "Intraventricular brain-derived neurotropic factor reduces infarct size after focal cerebral ischemia in rats," *J. Cereb. Blood Flow Metab.* 17: 500-506 (1997).

Schaller et al., "Elevated levels of head activator in human brain tumors and in serum of patients with brain and other neurally derived tumors," *J. Neuro. Oncol.* 6:251-258 (1988).

Schins and Borm, "Epidermological evaluation or release of monocyte TNF-αas an exposure and effect marker in pneumonoconiosis: a five year follow up study of coal workers," *Occup. Environ. Med.* 52:441-50 (1995).

Schwab et al., "Plasma insulin-like growth factor I and IGF binding protein 3 levels in patients with acute cerebral ischemic injury," *Stroke* 28:1744-1748 (1997).

Schwartz et al., "Tryptase levels as an indicator of mast-cell activation in systemic anaphylaxis and mastocytosis," *N. Engl. J. Med.* 316:1622-26 (1987).

Seki et al., "Sustained activation of blood coagulation in patients with cerebral thrombosis," *A. J. Hematol.* 50: 155-160 (1995).

Seki et al., "Plasma levels of thrombomodulin and lipoprotein (a) in patients with cerebral thrombosis," *Blood Coagul. Fibrinolysis* 8:391-396 (1997).

Seymour, L. et al., "Tissue platelet derived-growth factor (PDGF) predicts for shortened survival and treatment failure in advanced breast cancer," *Breast Cancer Res. Treat.* 26:247-252 (1993).

Shamsham and Mitchell, "Essentials of the diagnosis of heart failure," *Am. Fam. Physician* 61:1319-28 (2000).

Shibata, M. et al., "Effect of magnesium sulfate pretreatment and significance of matrix metalloproteinase-1 and interleukin-6 Levels in coronary reperfusion therapy for patients with acute myocardial infarction," *Angiology* 50:573-582 (1999).

Shimomura, H. et al., "Serial changes in plasma levels of soluble P-selectin in patients with acute myocardial infarction," *Am. J. Cardiol.* 81:397-400 (1998).

Shyu et al., "Serum levels of intercellular adhesion molecule-1 and E-selectin in patients with acute ischaemic stroke," *J. Neurol.* 244:90-93 (1997).

Siess, W., "Lysophosphaditic acid mediates the rapid activation of platelets and endothelial cells by mildly oxidized low density lipoprotein and accumulates in human atherosclerotic lesions," *Proc. Natl. Acad. Sci. U.S.A.* 96, 6931-6936 (1999).

Sixma et al., "Von Willebrand factor and the blood vessel wall," *Mayo Clin. Proc.* 66:628-633 (1991).

Skogseid et al., "Increased serum creatine kinase BB and neuron specific enolase following head injury indicates brain damage," *Acta Neurochir* (Wein), 115: 106-111 (1992).

Sobel, M. et al., "Circulating platelet products in unstable angina pectoris," *Circulation* 63:300-306 (1981).

Soejima, H. et al., "Heightened tissue factor associated with tissue factor pathway inhibitor and prognosis in patients with unstable angina," *Circulation* 99:2908-2913 (1999).

Soejima, H. et al., "Angiotensin-converting enzyme inhibition reduces monocyte chemoattractant protein-1 and tissue factor levels in patients with myocardial infarction," *J. Am. Coll. Cardiol.* 34:983-988 (1999).

Sorbi et al., "Elevated levels of 92-kd type IV collagenase (Matrix metalloproteinase 9) in giant cell arteritis," *Arthritis Rheum.* 39:1747-1753 (1996).

Sorkness et al., "Evaluation of serum eosinophil cationic protein as a predictive marker for asthma exacerbation in patients with persistent disease," *Clin. Exp. Allergy* 32:1355-59 (2002).

Soufer et al., "Intact systolic left ventricular function in clinical congestive heart failure," *Am. J. Cardiol.* 55:1032-6 (1985).

Squadrito, F. et al., "Thrombolytic therapy with urokinase reduces increased circulating endothelial adhesion molecules in acute myocardial infarction," *Inflamm. Res.* 45:14-19 (1996).

Steiner et al., "Increased levels of soluble adhesion molecules in Type 2 (Non-insulin dependent) diabetes mellitus are independent of glycaemic control," *Thromb. Haemost.* 72:979-984 (1994).

Stockman et al., "Secondary structure and topology of interleukin-1 receptor antagonist protein determined by heteronuclear three-dimensional NMR spectroscopy," *Biochemistry* 31:5237-5245 (1992).

Suefuji, H. et al., "Increased plasma tissue factor levels in acute myocardial infarction," *Am. Heart J.* 134:253-259 (1997).

Suga et al., "Clinical significance of MCP-1 levels in BALF and serum in patients with interstitial lung diseases," *Eur. Respir. J.* 14:376-382 (1999).

Switaiska et al., "Radioimmunoassay of human platelet thrombospondin: different patterns of thrombospondin and β-thromboglobulin antigen secretion and clearance from the circulation," *J. Lab. Clin. Med.* 106: 690-700 (1985).

Taira et al., "Serum B12 tryptase level as a marker of allergic airway inflammation in asthma," *J. Asthma* 39:315-22 (2002).

Takahashi et al., "Tissue factor in plasma of patients with disseminated intravascular coagulation," *Am. J. Hematol.* 46:333-337 (1994).

Takeda, I. et al., "Soluble P-selectin in the plasma of patients with connective tissue diseases," *Int. Arch. Allergy Immunol.* 105:128-134 (1994).

Tanaka, M. and Suzuki, A., Hemostatic abnormalities in acute myocardial infarction as detected by specific blood markers, *Thromb. Res.* 76:289-98 (1994).

Tanaka, T. et al., "Serum and urinary human heart fatty acid-binding protein in acute myocardial infarction," *Clin. Biochem.* 24:195-201 (1991).

Tanasijevic, M.J., "The role of cardiac troponin-I (cTnI) in risk stratification of patients with unstable coronary artery disease," et al., *Clin. Cardiol.* 22:13-16 (1999).

Tateyama et al., "Concentrations and molecular forms of human brain natriuretic peptide in plasma," *Biochem. Biophys. Res. Commun.* 185:760-7 (1992).

Tenaglia, A.N. et al., "Levels of expression of P-selectin, E-selectin, and intercellular adhesion molecule-1 in coronary atherectomy specimens from patients with stable and unstable angina pectoris," *Am. J. Cardiol.* 79:742-747 (1997).

Thomas et al., "Serum myelin basic protein, clinical responsiveness, and outcome of severe head injury," *Acta Neurochir. Suppl.* 28: 93-95 (1979).

Thygesen, K. et al., "Creatine kinase and creatine kinase B-subunit in stable and unstable angina pectoris," *Eur. J. Clin. Invest.* 16:1-4 (1986).

Burtis et al "Tietz Textbook of Clinical Chemistry"; 2nd edition, Carl Burtis and Edward Ashwood eds., W.B. Saunders and Company, p. 485-507.

Tohgi et al., "Coagulation-fibrinolysis abnormalities in acute and chronic phases of cerebral thrombosis and embolism," *Stroke* 21: 1663-1667 (1990).

Tomoda, H. and Aoki, N., "Plasma soluble P-selectin in acute myocardial infarction: effects of coronary recanalization therapy," *Angiology* 49:807-813 (1998).

Tousoulis et al., "Von Willebrand factor in patients evolving Q-wave versus non-Q-wave acute myocardial infarction," *Int. J. Cardiol.* 56:259-262 (1996).

Trotter et al., "Immunoreactive myelin proteolipid protein-like activity in cerebrospinal fluid and serum of neurologically impaired patients," *Ann. Neurol.*, 14: 554-558 (1983).

Tsuji, R. et al., "Human heart-type cytoplasmic fatty acid-binding protein in serum and urine during hyperacute myocardial infarction," *Int J. Cardiol.* 41:209-217 (1993).

Uchiyama et al., "Alterations of platelet, coagulation, and fibrinolysis markers in patients with acute ischemic stroke," *Semin. Thromb. Hemost.* 23: 535-541 (1997).

Ushiyama, S. et al., "Structural and functional characterization of monomeric soluble P-selectin and comparison with membrane P-selectin," *J. Biol. Chem.* 268:15229-15237 (1993).

Usui, A. et al., "β-Enolase in blood plasma during open heart surgery," *Cardiovasc. Res.* 23:737-740 (1989).

Usui, A. et al., "Neural tissue-related proteins (NSE, $G_0\alpha$, 28-kDa calbidin-D, S100b and CK-BB) in serum and cerebrospinal fluid after cardiac arrest," *J. Neurol. Sci.* 123:134-139 (1994).

Usui, A. et al., "S-100$a_o$ protein in blood and urine during open-heart surgery," *Clin. Chem.* 35:1942-1944 (1989).

Usui, A. et al., "S-100$a_o$ protein in serum during acute myocardial infarction," *Clin. Chem.* 36:639-641 (1990).

van den Dorpel, M.A. et al., "Low-density lipoprotein oxidation is increased in kidney transplant recipients," *Transpl. Int. 9 Suppl.* 1:S54-S57 (1996).

Van Nieuwenhoven, F.A. et al., "Discrimination between myocardial and skeletal muscle injury by assessment of the plasma ratio of myoglobin over fatty acid-binding protein," *Circulation* 92:2848-2854 (1995).

Veerkamp, J.H. and Maatman, R.G., "Cytoplasmic fatty acid-binding proteins: their structure and genes," *Prog. Lipid Res.* 34:17-52 (1995).

Venge, "Serum measurements of eosinophil cationic protein (ECP) in bronchial asthma" *Clinical and experimental allergy*, 23 ( 2):3-7 (1993).

Viera et al., "Isolation and expression of human cytokine synthesis inhibitory factor cDNA clones: homologyto Epstein-Barr virus open reading frame BCRFI," *Proc. Natl. Acad Sci. USA* 88:1172-76 (1991).

Virchow et al., "Sputum ECP levels correlate with parameters of airflow obstruction," *Am. Rev. Respir. Dis.* 146:604-6 (1992).

Wallace, J.M. et al., "The assessment of platelet derived growth factor concentration in post myocardial infarction and stable angina patients," *Ann. Clin. Biochem.* 35:236-241 (1998).

Ward et al., Binding activities of a repertoireof singleimmunoglobulin variable domains secreted from *Escherichia coli*, *Nature* 341:544-546 (1989).

Whicher et al., "Procalcitonin asan acute phase marker," *Ann. Clin. Biochem.* 38: 483-93 (2001).

Wilkins et al., "The natriuretic-peptide family," *Lancet*, 349:1307-1310 (1997).

Wilson et al., "Simplified conjugation chemistry for coupling peptides to F(ab') fragments: autologous red cell agglutination assay for HIV-1 antibodies," *J. Immunol. Methods* 175:267-273 (1994).

Winnikes et al., "Head activator as a potential serum marker for brain tumor analysis," *Eur. J. Cancer* 28:421-424 (1992).

Woertgen et al., "Comparison of serial S-100 and NSE serum measurements after severe head injury," *Acta Neurochir* (Wien) 139: 1161-1165 (1997).

Xu, Y. et al., "Lysophosphatidic Acid as a potential biomarker for ovarian and other gynecologic cancers," *JAMA* 280:719-723 (1998).

Yamane et al., "Serum levels of KL-6 as a useful marker for evaluating pulmonary fibrosis in patients with systemic sclerosis," *J. Rheumatol.* 27:930-4 (2000).

Yamazaki et al., "Alterations of haemostatic markers in various subtypes and phases of stroke," *Blood Coagul. Fibrinolysis* 4:707-712 (1993).

Yap et al., "Contraction to big endothelin-1, big endothelin-2 and big endothelin-3, and endothelin-converting enzyme inhibition in human isolated bronchi," *Br. J. Pharmacol.* 129:170-6 (2000).

Yarmush et al., "Coupling of antibody-binding fragments to solid-phase supports: site directed binding of $F(ab')_2$ fragments," *J. Biochem. Biophys. Methods* 25:285-297 (1992).

Yazdani, S. et al., "Percutaneous interventions alter the hemostatic profile of patients with unstable versus stable angina," *J Am Coll Cardiol* 30:1284-1287 (1997).

Yoneda et al., "Identification of a novel adenylate kinase system in the brain: Cloning of the fourth adenylate kinase," *Mol. Brain Res.* 62:187-195 (1998).

Yoshimoto, K. et al., "Human heart-type cytoplasmic fatty acid-binding protein as an indicator of acute myocardial infarction," *Heart Vessels* 10:304-309 (1995).

Yoshimura et al., "Human monocyte chemoattractant protein-1 (MCP-1)," *FEBS Lett.* 244:487-493 (1989).

Yoshitomi et al., "Plasma levels of adrenomedullin in patients with acute myocardial infarction," *Clin. Sci.* 94:135-9 (1998).

Yukioka et al., "Plasma procalcitonin in sepsis and organ failure," *Ann. Acad. Med. Singapore* 30:528-31 (2001).

Zucker et al., "Increased serum stromelysin-1 levels in systemic lupus erythematosus: lack of correlation with disease activity," *J. Rheumatol.* 26:78-80 (1999).

International Search Report mailed Jan. 5, 2005 for International Application No. PCT/US2003/41453.

International Search Report for PCT application No. PCT/US03/41426.

Humes, D.H., *Kelley's Textbook of Internal Medicine*, 4th Ed., Lippincott Williams & Wilkins, Philadelphia, PA, 2000, pp. 2349-2354, "Approach to the Patient With Dyspnea."

Kim et al., "Kidney as a major clearance organ for recombinant human interleukin-1 receptor antagonist," *J. Pharm. Sci.*, 84:575-580 (1995).

Kim et al., "Structure of the mouse IL-10 gene and chromosomal localization of the mouse and human genes," *J. Immunol.* 148:3618-23 (1992).

Kobayashi and Kitamura, "KL-6: a serum marker for interstitial pneumonia," *Chest* 108:311-15 (1995).

Theroux, P. et al., "Febrinopeptide A and platelet factor levels in unstable angina pectoris," *Circulation* 75:156-162 (1987).

Albrechtsen, M. and Bock, E. J., Quantification of Glial Fibrillary Acidic Protein (GFAP) in Human Body Fluids by means of ELISA Employing a Monoclonal Antibody, *Neuroimmunol.* 8:301-309 (1985).

Ardissino, D. et al., "Tissue-factor antigen and activity in human coronary atherosclerotic plaques," *Lancet* 349:769-771 (1997).

Bialik et al., "Myocyte apoptosis during acute myocardial infarction in the mouse localizes to hypoxic regions but occurs independently of p53," *J. Clin. Invest.* 100(6): 1363-1372 (1997).

Blann, A.D. et al., "Evidence of platelet activation in hypertension," *J. Hum. Hypertens.* 11:607-609 (1997).

Blann, A.D. et al., "Soluble P-selectin in atherosclerosis: a comparison with endothelial cell and platelet markers," *Thromb. Haemost.* 77:1077-1080 (1997).

Bonfrer et al., "The luminescence immunoassay S-100: a sensitive test to measure circulating S-100B: its prognostic value in malignant melanoma," *Brit. Jour. of Cancer* 77(12): 2210-2214 (1998).

Colucciello, S.A., *EMR Textbook*, pp. 1-23 http://www.thrombosis-consult.com/articles/Texbook/54_pulmonary, printed Nov. 4, 2002.

Dao et al., "Utility of B-Type Natriuretic Peptide in the Diagnosis of Congestive Heart Failure in an Urgent-Care Setting," *J. Am. Coll. Cardiol.* 37:379-85 (2001).

Dinerman, J.L. et al., "Increased neutrophil elastase release in unstable angina pectoris and acute myocardial infarction," *J. Am. Coll. Cardiol.* 15:1559-1563 (1990).

Portales, P.J. et al., "Utility of the serum biochemical markers CPK, CPK MB mass, myoglobin, and cardiac troponin T in a chest pain unit," *Rev. Esp. Cardio.* 55(9):913-20 (Sep 2002).

Hammer-Lercher et al., "Head-to-head comparison of N-terminal pro-brain natriuretic peptide, brain natriuretic peptideand N-terminal pro-atrial natriuretic peptide in diagnosis left ventricular dysfunction," *Clin. Chim. Acta* 310(2):193-7 (2001).

Hasegawa, S. et al., "S100$a_0$ protein as a marker for tissue damage related to extracorporeal shock wave lithotripsy," *Eur. Urol.* 24:393-396 (1993).

Humes, D.H., *Kelley's Textbook of Internal Medicine*, 4th Ed., Lippincott Williams & Wilkins, Philadelphia, PA, 2000, pp. 2349-2354, "Approach to the Patient With Dyspnea."

Keyszer, G. et al., "Matrix metalloproteinases, but not catharsis B, H, and L or their inhibitors in peripheral blood of patients with rheumatoid arthritis are potentially useful markers of disease activity," *Z Rheumatol.* 57:392-398 (1998).

Kim et al., "Kidney as a major clearance organ for recombinant human interleukin-1 receptor antagonist," *J. Pharm. Sci.*, 84:575-580 (1995).

Kim et al., "Structure of the mouse IL-10 gene and chromosomal localization of the mouse and human genes," *J. Immunol.* 148:3618-23 (1992).

Kobayashi and Kitamura, "KL-6: a serum marker for interstitial pneumonia," *Chest* 108:311-15 (1995).

Laurino, J.P. et al., "Thrombus precursor protein™ and the measurement of thrombosis in patients with acute chest pain syndrome," *Ann. Clin. Lab. Sci.* 27:338-345 (1997).

MacManus, J.P. et al., "Cerebral ischemia produces laddered DNA fragments distinct from cardiac ischemia and archetypal apoptosis," *J. Cereb. Blood Flow Metab.* 19:502-510 (1999).

Mair, J., "Glycogen phosphorylase isoenzyme BB to diagnose ischaemic myocardial damage," *Clin. Chim. Acta* 272:79-86 (1998).

Mair, P. et al., "Glycogen phosphorylase isoenzyme BB mass release after coronary artery bypass grafting," *Eur. J. Clin. Chem. Clin. Biochem.* 32:543-547 (1994).

Sakamaki, F. et al., "Soluble form of P-selecting in plasma is elevated in acute lung injury," *A. J. Respir. Crit. Care Med.* 151:1821-1826 (1995).

Sakata, K. et al., Characteristics of vasosplastic angina with exercised-induced ischemia—analysis of parameters of hemostatis and fibrinolysis. *Jpn. Circ. J.* 60:277-284 (1996).

Theroux, P. et al., "Febrinopeptide A and platelet factor levels in unstable angina pectoris," *Circulation* 75:156-162 (1987).

Tietz Textbook of Clinical Chemistry, 2nd edition, Carl Burtis and Edward Ashwood eds., W.B. Saunders and Company, p. 485-507.

Venge, "Serum measurements of eosinophil cationic protein (ECP) in bronchial asthma," *Clinical and experimental allergy*, 23 ( 2):3-7 (1993).

Ward et al., Binding activities of a repertoire of single immunoglobulin variable domains secreted from *Escherichia coli*, *Nature* 341:544-546 (1989).

Whicher et al., "Procalcitonin as an acute phase marker," *Ann. Clin. Biochem.* 38: 483-93 (2001).

De Bruyn et al., *A systematic review of the diagnostic accuracy of physical examination for the detection of cirrhosis*, BMC Medical Informatics and Decision Making, 2001, pp. 1-11, vol. 1.

Hassan et al., "Non-viable myocardium, documented by TL-201 SPECT, is a main determinant of the increase in the secretion of cardiac natriuretic peptides" Medecine Nucleaire, 2000, 24/6, pp. 301-310 (Database EMBASE Accession No. 2001129199 and English language translation).

Singh et al., "Optimization technique in human gall bladder health care system." The 1996 IEEE International Conference on Systems, Man and Cybernetics. Part 4 of 4. vol. 4, pp. 2855-2857.

Takebayashi et al. "Association between circulating monocyte chemoattractant protein-1 and urinary albumin excretion in nonobese Type 2 diabetic patients", J. Diabetes and its Complications, 2006, vol. 20, pp. 98-104.

Vasan, "Biomarkers of cardiovascular disease: molecular basis and practical considerations", Circulation, 2006, vol. 113, pp. 2335-2362.

Zweig et al. "Receiver-operating characteristic (ROC) Plots: A fundamental evaluation tool in clinical medicine", Clin. Chem. 1993, vol. 39, pp. 561-577.

Heeschen et al. "Troponin concentrations for stratification of patients with acute coronary syndromes in relation to therapeutic efficacy of tirofiban", The Lancet, 1999,, vol. 354, pp. 1757-1762.

Indik et al., "Detection of pulmonary embolism by D-dimer assays, spiral computed tomography, and magnetic resonance imaging", Progress in Cardiovascular Diseases, 2000, vol. 42, pp. 261-272.

European Search Report dated Oct. 16, 2007 for EP Application No. EP 07107064.3.

International Search Report dated Apr. 30, 2008 from PCT Application No. US 2007/69475.

Adams, et al. Cardiac troponin I. A marker with high specificity for cardiac injury.Circulation. 1993; 88: 101-106.

Adams, et al., Diagnosis of Perioperative Myocardial Infarction with Measurement of Cardiac Troponin I N Engl J Med, 330:670-674 (1994).

Al-Ahmad et al. Reduced Kidney Function and Anemia as Risk Factors for Mortality in Patients With Left Ventricular Dysfunction. Journal of the American College of Cardiology. Oct. 2001; 38(4), pp. 955-962.

Bellorini et al. Interest of BNP and Troponin in the Management of Cardiologic Emergency. J. of European Society of Cardiology. Sep. 1-5, 2001; 22: 518.

Bettencourt, et al. Evaluation of brain natriuretic peptide in the diagnosis of heart failure. Cardiology. 2000;93(1-2):19-25.

Blennow, et al. Combination of the different biological markers for increasing specificity of in vivo Alzheimer's testing. J Neural Transm Suppl. 1998;53:223-35.

Blum, et al. The role of inflammation in atherosclerosis. Isr J Med Sci. Nov. 1996;32(11):1059-65.

Boomsma, et al. Plasma A- and B-type Natriuretic Peptides: Physiology; Methodology and Clinical Use. Cardiovascular Research. 2001; 51:442-449.

Brunner-La Rocca, et al. Is blood pressure response to the Valsalva maneuver related to neurohormones, exercise capacity, and clinical findings in heart failure? Chest. Oct. 1999;116(4):861-7.

Chen et al. The Natriuretic Peptides in Heart Failure: Diagnostic and Therapeutic Potentials. Proceedings of the Assoc of American Physicians. Sep./Oct. 1999; 11 1(5):406-416.

Cho, et al. Natriuretic peptides and their therapeutic potential. Heart Dis. 1: 305-28, (1999).

Christenson, et al. Biochemical markers of the acute coronary syndromes. Clin Chem. Aug. 1998;44(8 Pt 2):1855-64.

Chu et al. A Review of Clinically Relevant Cardiac Biochemical Markers, Wisconsin Medical Journal. 2002; 101(3):40-48.

Clerico, et al. Diagnostic Accuracy and Prognostic Relevance of the Measurement of Cardiac Natriuretic Peptides: A Review. Clinical Chemistry. 2004; 50(1):33-50.

Daggubati, et al. Adrenomedullin, endothelin, neuropeptide Y, atrial, brain, and C-natriuretic prohormone peptides compared as early heart failure indicators. Cardiovasc Res. Nov. 1997;36(2):246-55.

De Lemos et al. Combining Natriuretic Peptides and Necrosis Markers in the Assessment of Acute Coronary Syndromes. Reviews in Cardiovascular Medicine. 2003; 4(4): S37-S46.

Duffus, et al. Glossary for chemists of terms used in toxicology. 1993;Pure & Appl. Chem. 65 (9) : 2003-2122.

Espiner, et al. Natriuretic hormones. Endocrinol Metab Clin North Am. Sep. 1995;24(3):481-509.

Fonarow, et al. Combining Natriuretic Peptides and Necrosis Markers in Determining Prognosis in Heart Failure. Reviews in Cardiovascular Medicine. 2003; 4(4):S20-S28.

Fu, et al. Proteomics and heart disease: identifying biomarkers of clinical utility. Expert Rev Proteomics. Apr. 2006;3(2):237-49.

Harrington, J.R. The Role of MCP-1 in Atherosclerosis. Stem Cells. 2000;18: 65-66.

Jancin B. Rapid test Helps Identify Cause of Dyspnea—Point-of-Care Brain Natriuretic Peptide Immunoassay, [on-line]. <uRL: http://www.findarticles.com/p/articles/mi_mOBJI/is_9_30/ai_63125276/0...: 2, 2000.

Jeffrey, S. BNP Diagnostic Test for CHF Receives FDA Approval. TheHeart.org. Available at: http://www.theheart.org, Nov. 28, 2000.

Jones, et al. Elevated brain natriuretic peptide in septic patients without heart failure. Ann Emerg Med. Nov. 2003;42(5):714-5.

Alpert et al., Journal of the American College of Cardiology, Myocardial infarction redefined—A Consensus document of the Joint European Society of Cardiology/American College of Cardiology Committee for the redefinition of myocardial infarction. 36:959-969, 2000.

Katrukha, et al. Troponin I is released in bloodstream of patients with acute myocardial infarction not in free form but as complex. Clin Chem. Aug. 1997;43(8 Pt 1):1379-85.

Kucher, et al. Low pro-brain natriuretic peptide levels predict benign clinical outcome in acute pulmonary embolism. Circulation. Apr. 1, 2003;107(12):1576-8.

Kucher, et al. Prognostic role of brain natriuretic peptide in acute pulmonary embolism. Circulation. May 27, 2003;107(20):2545-7.

Lainchbury, et al. Brain Natriuretic Peptide and N-Terminal Brain Natriuretic Peptide in the Diagnosis of Heart Failure in Patients With Acute Shortness of Breath. J. Am. Coll. Cardiol. Aug. 20, 2003; 42(4):728-35.

Lindon, J. C. Biomarkers: Present concepts and future promise. Preclinica. 2003;1: 221.

Maeder, et al. Elevation of B-type natriuretic peptide levels in acute respiratory distress syndrome. Swiss Med Wkly. Sep. 26, 2003;133(37-38):515-8.

Maisel A. Cardiac Biomarkers Aid in Diagnosing Ischemia and Heart Failure. CVR&R, Apr. 2001; 22(4): 217-222.

Maisel, A. Algorithms for using B-type natriuretic Peptide levels in the diagnosis and management of congestive heart failure. Crit Pathw Cardiol. Jun. 2002;1(2):67-73.

Maisel, A. B-type natriuretic peptide (BNP) levels: diagnostic and therapeutic potential. Rev Cardiovasc Med. 2001;2 Suppl 2:S13-8.

Maisel, A. Practical approaches to treating patients with acute decompensated heart failure. J Card Fail. Jun. 2001;7(2 Suppl 1):13-7.

Maisel, et al. Measuring BNP levels in the diagnosis and treatment of CHF. Journal of Critical Illness. 2002; 17(11), pp. 434-442.

Maisel, et al. Rapid measurement of B-type natriuretic peptide in the emergency diagnosis of heart failure. N. Engl J Med. Jul. 18, 2002;347(3):161-7.

McCullough et al. B-Type Natriuretic Peptide and Renal Function in the Diagnosis of Heart Failure: An Analysis From the Breathing Not Properly Multinational Study, Circulation, 2002, vol. 106, pp. 416-422.

McGeoch, et al. Plasma Brain Natriuretic Peptide After Long-Term Treatment for Heart Failure in General Practice, The European Journal of Heart Failure, 2002, pp. 479-483, vol. 4, Elsevier Science B.V.

McLean, et al. Increased B-type natriuretic peptide (BNP) level is a strong predictor for cardiac dysfunction in intensive care unit patients.Anaesth Intensive Care. Feb. 2003;31(1):21-7.

McNairy, et al. Stability of B-type natriuretic peptide levels during exercise in patients with congestive heart failure: implications for outpatient monitoring with B-type natriuretic peptide. Am Heart J. Mar. 2002;143(3):406-11.

Meyer, et al. Cardiac troponin I elevation in acute pulmonary embolism is associated with right ventricular dysfunction. J Am Coll Cardiol. Nov. 1, 2000;36(5):1632-6.

Naganuma, et al. The prognostic role of brain natriuretic peptides in hemodialysis patients. Am J Nephrol. Sep.-Dec. 2002;22(5-6):437-44.

Peacock, W. The B-type natriuretic peptide assay: a rapid test for heart failure. Cleve Clin J Med. Mar. 2002;69(3):243-51.

Richards et al., B-Type Natriuretic Peptides and Ejection Fraction for Prognosis After Myocardial Infarction, Circulation, Jun. 10, 2003; 107:2786-92.

Richards et al., Plasma N-Terminal Pro-Brain Natriuretic Peptide and Adrenomedullin; New Neurohormonal Predictors of Left Ventricular Function and Prognosis After Myocardial Infarction, May 19, 1998; 97:1921-1929.

Ristori, et al. Serum amyloid a protein is elevated in relapsing-remitting multiple sclerosis. J Neuroimmunol. Aug. 1, 1998;88(1-2):9-12.

Safley, et al. The emerging role of brain natriuretic peptide in the management of acute and chronic heart failure in outpatients. Heart Fail Monit. 2003;4(1):13-20.

Samama, M. Pulmonary embolism: controversies in laboratory studies J. Pathophysiol Haemost Thromb. 2006;35(1-2):157-61.

Schwagerl, et al. Elevated levels of the endosomal-lysosomal proteinase cathepsin D in cerebrospinal fluid in Alzheimer disease. J. neurochem. 1995, vol. 64, No .1, pp. 443-446.

Shapiro, et al. Use of Plasma Brain Natriuretic Peptide Concentration to Aid in the Diagnosis of Heart Failure. Mayo Clin Proc. 2003;78:481-486.

Tsekoura, et al. Brain natriuretic peptide. Hellenic J. Cardiol. 2003; 44:266-270.

Tulevski, I. Utility of a BNP as a marker for RV dysfunction in acute pulmonary embolism. J Am Coll Cardiol. Jun. 19, 2002;39(12):2080-2 081.

Watson, et al. Clinical utility of biochemical analysis of cerebrospinal fluid. Clin Chem. Mar. 1995;41(3):343-60.

Wieczorek, et al. A rapid B-type natriuretic peptide assay accurately diagnoses left ventricular dysfunction and heart failure: a multicenter evaluation. Am Heart J. Nov. 2002; 144(5):834-9.

Wijnberger, et al. Expression in the placenta of neuronal markers for perinatal brain damage. Pediatr Res. Apr. 2002;51(4):492-6.

Wood, S. Breathing Not Properly Trial Indicates BNP Tests Should Be Incorporated Into ACC/AHA CHF Guidelines. TheHeart.org. Available at:http://www.theheart.org, Mar. 19, 2002.

Wright et al., Plasma Amino-terminal Pro-Brain Natriuretic Peptide and accuracy of Heart-Failure Diagnosis in Primary Care, J. Am. Coll. Cardiol., Nov. 19, 2003; Elsevier Inc. 42:10:1793-1800.

Yamamoto, et al. Effect of endogenous natriuretic peptide system on ventricular and coronary function in failing heart. Am J Physiol. Nov. 1997;273(5 Pt 2):H2406-14.

Zoccali et al., Cardiac Natriuretic Peptides are Related to Left Ventricular Mass and Function and Predict Mortality in Dialysis Patients, J. Am. Soc. Nephrol, 2001; 12:1508-1515.

Baig, et al. The pathophysiology of advanced heart failure. Am Heart J. Jun. 1998;135(6 Pt 2 Su):S216-230.

Biasucci, L. M. CDC/AHA Workshop on Markers of Inflammation and Cardiovascular Disease: Application to Clinical and Public Health Practice: clinical use of inflammatory markers in patients with cardiovascular diseases: a background paper. *Circulation*. Dec. 21, 2004;110(25):e560-7.

Fassbender, et al. Changes in coagulation and fibrinolysis markers in acute ischemic stroke treated with recombinant tissue plasminogen activator. Stroke. Oct. 1999;30(10):2101-4.

Felker, et al. Natriuretic peptides in the diagnosis and management of heart failure CMAJ. Sep. 12, 2006; 175(6): 611-617.

Freitag, et al. Plasma Brain Natriuretic Peptide Levels and Blood Pressure Tracking in the Framingham Heart Study. Hypertension. 2003;41:978-983.

Lecapra, et al. The Use of Thrombus Precursor Protein, D-dimer, prothrombin fragment 1.2, and thrombin antithrombin in the exclusion of proximal deep vein thrombosis and pulmonary embolism. Blood Coagul. Fibrinolysis 2000;11: 371-7.

Watanabe, et al. Plasma levels of activated protein C-protein C inhibitor complex in patients with hypercoagulable states. Am. J. Hematol. 2000;65: 35-40.

Wells, et al., Excluding Pulmonary Embolism at the Bedside Without Diagnostic Imaging: Management of Patients with Suspected Pulmonary Embolism Presenting to the Emergency Department by Using a Simple Clinical Model and b-Dimer Ann. Intern. Med. 135:98-107 (2001).

Morrison, et al. Utility of a rapid B-natriuretic peptide assay in differentiating congestive heart failure from lung disease in patients presenting with dyspnea. J Am Coll Cardiol. 2002; 39(2):202-9.

International Search Report for PCT application No. PCT/US03/41426, Feb. 18, 2005.

Ay et al., Creatine kinase-MB elevation after stroke is not cardiac in origin: Comparison with troponin T levels. Stroke 33:286-289, 2002.

Ben-Dor et al., Tissue classification with gene expression profiles. Proceedings of the Fourth Annual International Conference on Computational Molecular Biology, 2000, p. 54-64.

Futterman et al., Novel markers in the acute coronary syndrome: BNP, IL-6, PAPP-A, American Journal of Critical care, 11(2): 168-172, 2002.

Lamers et al., Cerebrospinal neuron-specific enolase, S-100 and myelin basic protein in neurological disorders. Acta Neurologica Scand 92:247-251, 1995.

Persson et al., S-100 protein and neuron-specific enolase in cerebrospinal fluid and serum: markers of cell damage in human contral nervous system. Stroke 18:911-918, 1987.

Quinn et al., D-Dimers in the diagnosis of pulmonary embolism. Am J Respir Crit Care Med 159:1445-1449, 1999.

Sagnella, Measurement and significance of circulating natriuretic peptides in cardiovascular disease. Clinical Science 95:519-529, 1998.

Schneider et al., Fuzzy logic-based tumor-marker profiles improved sensitivity in the diagnosis of lung cancer. International Journal of Clinical Oncology, Churchill Livingston Japan, 7(3): 145-151, 2002.

Sonel et al., Prospective study correlating fibrinopeptide A, Troponin I, myoglobin and myosin light chain levels with early and late lschemic events in consecutive patients presenting to the emergency department with chest pain. Circulation 102:1107-1113, 2000.

Veer et al., Gene expression profiling predicts clinical outcome of breast cancer. Nature, 415(6871): 530-536, 2002.

Villacorta et al., The role of B-type natriuretic peptide in the diagnosis of congestive heart failure in patients presenting to an emergency department with dyspnea. Arq Bras Cardiol 79(6): 569-572, 2002.

Zhang et al., Recursive partitioning for tumor classification with gene expression microarray data. Proceedings of the National Academy of Sciences, 98(12): 6730-6735, 2001.

European Search Report for EP Application No. 03 81 0896, Mar. 19, 2007.

Supplementary Partial European Search Report for EP Application EP 03 81 4398, Apr. 19, 2007.

* cited by examiner

MARKERS FOR DIFFERENTIAL DIAGNOSIS AND METHODS OF USE THEREOF

This application is related to U.S. Provisional Patent Application No. 60/436,301, filed Dec. 24, 2002, from which priority is claimed, and which is hereby incorporated by reference in its entirety, including all tables, figures, and claims.

FIELD OF THE INVENTION

The present invention relates to the identification and use of diagnostic markers for differential diagnosis of diseases. In a various aspects, the invention relates to methods and compositions able to determine the presence or absence of one, and preferably a plurality, of diseases that exhibit one or more similar or identical symptoms.

BACKGROUND OF THE INVENTION

The following discussion of the background of the invention is merely provided to aid the reader in understanding the invention and is not admitted to describe or constitute prior art to the present invention.

The clinical presentation of certain diseases can often be strikingly similar, even though the underlying diseases, and the appropriate treatments to be given to one suffering from the various diseases, can be completely distinct. For example, subjects may present in an urgent care facility exhibiting a deceptively simple constellation of apparent symptoms (e.g., fever, shortness of breath, dizzyness, headache) that may be characteristic of a variety of unrelated conditions. Differential diagnosis methods involve the comparison of symptoms and/or diagnostic test results known to be associated with one or more diseases that exhibit a similar clinical presentation to the symptoms and/or diagnostic results exhibited by the subject, in order to identify the underlying disease or condition present in the subject.

Taking shortness of breath (referred to clinically as "dyspnea") as an example, patients often present in a clinical setting with this symptom as the initial clinical presentation. This symptom considered in isolation may be indicative of conditions as diverse as asthma, chronic obstructive pulmonary disease ("COPD"), tracheal stenosis, obstructive endobroncheal tumor, pulmonary fibrosis, pneumoconiosis, lymphangitic carcinomatosis, kyphoscoliosis, pleural effusion, amyotrophic lateral sclerosis, congestive heart failure, coronary artery disease, myocardial infarction, cardiomyopathy, valvular dysfunction, left ventricle hypertrophy, pericarditis, arrhythmia, pulmonary embolism, metabolic acidosis, chronic bronchitis, pneumonia, anxiety, sepsis, aneurismic dissection, etc. See, e.g., *Kelley's Textbook of Internal Medicine*, 4th Ed., Lippincott Williams & Wilkins, Philadelphia, Pa., 2000, pp. 2349-2354, "Approach to the Patient With Dyspnea"; Mulrow et al., *J. Gen. Int. Med*. 8: 383-92 (1993).

Differential diagnosis in the case of dyspnea involves identifying the particular condition causing shortness of breath in a given subject from amongst numerous possible causes. These methods often require that the clinician integrate information obtained from a battery of tests, leading to a clinical diagnosis that most closely represents the range of symptoms and/or diagnostic test results obtained for the subject. The tests required may include radiography, electrocardiogram, exercise treadmill testing, blood chemistry analysis, echocardiography, bronchoprovocation testing, spirometry, pulse oximetry, esophageal pH monitoring, laryngoscopy, computed tomography, histology, cytology, magnetic resonance imaging, etc. See, e.g., Morgan and Hodge, *Am. Fam. Physician* 57: 711-16 (1998). Because of the variety of tests that may need to be performed, obtaining sufficient information to arrive at a diagnosis can take hours or even days.

Differential diagnosis of chest pain requires the clinician to consider many possible causes, including differentiating between respiratory pain and pain associated with angina, or myocardial infarction and pleuritic and chest wall pain.

Differential diagnosis of diastolic and systolic dysfunction in patients suffering from heart failure is important since the therapies for each dysfunction are different. Further differentiation of atrial fibrillation from heart failure is critical for appropriate therapy.

In the area of infection, diffential diagnosis of viral versus bacterial is critical to the clinician delivering the appropriate therapy.

The acuteness or severity of the symptoms often dictates how rapidly a diagnosis must be established and treatment initiated. Immediate diagnosis and care of a patient experiencing a variety of acute conditions associated with dyspnea and chest pain can be critical. See, e.g., Harris, *Aust. Fam. Physician* 31: 802-06 (2002) (asthma); Goldhaber, *Eur. Respir. J. Suppl*. 35: 22s-27s (2002) (pulmonary embolism); Lundergan et al., *Am. Heart J*. 144: 456-62 (2002) (myocardial infarction). However, even in cases where the apparent symptoms appear relatively stable, rapid diagnosis, and the rapid initiation of treatment, can provide both relief from immediate discomfort and advantageous improvement in prognosis.

Each reference cited in the preceeding section is hereby incorporated by reference in its entirety, including all tables, figures, and claims.

SUMMARY OF THE INVENTION

The present invention relates to the identification and use of diagnostic markers for differential diagnosis of diseases. The methods and compositions described herein can meet the need in the art for rapid, sensitive and specific diagnostic assays to be used in the diagnosis and differentiation of various diseases that are related in terms of one or more clinical characteristics.

In various aspects, the invention relates to materials and procedures for identifying the underlying cause of one or more symptoms that, when considered in isolation, may be related to a plurality of possible underlying diseases or conditions; to using such markers in diagnosing and treating a patient and/or to monitor the course of a treatment regimen; to using such markers to identify subjects at risk for one or more adverse outcomes an underlying disease or condition; and for screening compounds and pharmaceutical compositions that might provide a benefit in treating or preventing such diseases or conditions.

In a first aspect, the invention discloses methods for determining the presence or absence of a disease in a subject that is exhibiting a perceptible change in one or more physical characteristics (that is, one or more "symptoms") that are indicative of a plurality of possible etiologies underlying the observed symptom(s). These methods comprise analyzing a test sample obtained from the subject for the presence or amount of one or more markers for one or more of the possible etiologies of the observed symptom(s). The presence or amount of such marker(s) in a sample obtained from the subject can be used to rule in or rule out one or. more of the possible etiologies, thereby either providing a diagnosis (rule-in) and/or excluding one or more diagnoses (rule-out).

In certain embodiments, these markers can be used to rule in or rule out one or more possible etiologies of shortness of breath, or "dyspnea." While the present invention is described hereinafter generally in terms of the differential diagnosis of diseases related to dyspnea, the skilled artisan will understand that the concepts of symptom-based differential diagnosis described herein are generally applicable to any physical characteristics that are indicative of a plurality of possible etiologies such as fever, chest pain (or "angina"), abdominal pain, neurologic dysfunction, disturbances in metabolic state, such as aberrant water, electrolyte, mineral, or acid-base metabolism, hypertension, dizzyness, headache, etc.

In preferred embodiments, the present invention relates to methods in which a test sample is analyzed for the presence or amount of a plurality of markers related to a plurality of possible etiologies, so that the method is adapted to rule in or out a plurality of possible underlying causes based upon the analysis of a single sample. In the case of dyspnea, the plurality of markers are preferably selected to rule in or out a plurality of the following: asthma, atrial fibrillation, chronic obstructive pulmonary disease ("COPD"), tracheal stenosis, obstructive endobronchial tumor, pulmonary fibrosis, pneumoconiosis, lymphangitic carcinomatosis, kyphoscoliosis, pleural effusion, amyotrophic lateral sclerosis, congestive heart failure, coronary artery disease, myocardial infarction, cardiomyopathy, valvular dysfunction, left ventricle hypertrophy, pericarditis, arrhythmia, pulmonary embolism, metabolic acidosis, chronic bronchitis, pneumonia, anxiety, sepsis, or aneurismic dissection. In a particularly preferred embodiment, the methods relate to defining the cause of dyspnea to rule in or rule out myocardial ischemia and cardiac necrosis, heart failure and pulmonary embolism. In yet another particularly preferred embodiment, the methods relate to defining the cause of dyspnea to rule in or rule out myocardial ischemia and cardiac necrosis, heart failure, pulmonary embolism and atrial fibrillation.

In the case of abdominal pain, the plurality of markers are preferably selected to rule in or out a plurality of the following: aortic aneurysm, mesenteric embolism, pancreatitis, appendicitis, myocardial infarction, one or more infectious diseases described above, influenza, esophageal carcinoma, gastric adenocarcinoma, colorectal adenocarcinoma, pancreatic tumors including ductal adenocarcinoma, cystadenocarcinoma, and insulinoma.

In the case of disturbanes of metabolic state, the plurality of markers are preferably selected to rule in or out a plurality of the following: diabetes mellitus, diabetic ketoacidosis, alcoholic ketoacidosis, respiratory acidosis, respiratory alkalosis, nonketogenic hyperglycemia, hypoglycemia, renal failure, interstitial renal disease, COPD, pneumonia, pulmonary and edema, asthma.

In another aspect, the present invention relates to methods and compositions for further subdividing congestive heart failure by distinguishing between systolic heart failure and diastolic heart failure. These methods comprise analyzing a test sample obtained from the subject for the presence or amount of one or more markers, the presence or amount of which can be used to rule in or out systolic heart failure and/or diastolic heart failure, or that can be used to distinguish between these two causes of congestive heart failure.

In another aspect, the present invention relates to methods and compositions for the differential diagnosis of atrial fibrillation and heart failure. The methods comprise analyzing a test sample obtained from the subject for the presence or amount of one or more markers, the presence or amount of which can be used to rule in or out heart failure or atrial fibrillation. In another aspect of this embodiment, the methods can be used to distinguish between systolic and diastolic dysfunction and atrial fibrillation. In yet another aspect of this embodiment, the methods can be used to distinguish between systolic and diastolic dysfunction, atrial fibrillation, myocardial ischemia and cardiac necrosis.

In another aspect, the present invention relates to methods and compositions for the differential diagnosis of aortic dissection and myocardial ischemia and necrosis. The methods comprise analyzing a test sample obtained from the subject for the presence or amount of one or more markers, the presence or amount of which can be used to rule in or out aortic dissection and myocardial ischemia and cardiac necrosis. In another aspect of this embodiment, the methods can be used to distinguish between aortic dissection, myocardial ischemia and cardiac necrosis and heart failure. In another aspect of this embodiment, the methods can be used to distinguish between aortic dissection, myocardial ischemia and cardiac necrosis, heart failure and atrial fibrillation. necrosis.

Preferred markers of the invention can differentiate between myocardial infarction, congestive heart failure, and pulmonary embolism as a cause of dyspnea. Particularly preferred markers for these diseases are cardiac-specific troponin isoforms, B-type natriuretic peptide, and D-dimer, respectively. Each of these preferred markers are described in detail hereinafter.

The markers described herein may be used individually, but are preferably used as members of a marker "panel" comprising a plurality of markers that are measured in a sample. Such a panel may be analyzed in a number of fashions well known to those of skill in the art. For example, each member of a panel may be compared to a "normal" value, or a value identified as being indicative of the presence or absence of a particular disease. A particular diagnosis may depend upon the comparison of each marker to this value; alternatively, if only a subset of markers are outside of a normal range, this subset may be indicative of a particular diagnosis.

In a related aspect, the present invention relates to methods for identifying marker panels for use in the foregoing methods. The sensitivity and specificity of a diagnostic test depends on more than just the "quality" of the test—they also depend on the definition of what constitutes an abnormal test. In practice, Receiver Operating Characteristic curves, or "ROC" curves, are typically calculated by plotting the value of a variable versus its relative frequency in "normal" and "disease" populations. For any particular marker, a distribution of marker levels for subjects with and without a disease will likely overlap. Under such conditions, a test does not absolutely distinguish normal from disease with 100% accuracy, and the area of overlap indicates where the test cannot distinguish normal from disease. A threshold is selected, above which (or below which, depending on how a marker moves with the disease) the test is considered to be abnormal and below which the test is considered to be normal. The area under the ROC curve is a measure of the probability that the perceived measurement will allow correct identification of a condition. ROC curves can be used even when test results don't necessarily give an accurate numeric value for a marker level; that is, as long as one can rank results, one can create an appropriate ROC curve. Such methods are well known in the art. See, e.g., Hanley et al., *Radiology* 143: 29-36 (1982).

In preferred embodiments, particular thresholds for one or more markers in a panel are not relied upon to determine if a profile of marker levels obtained from a subject are indicative of a particular diagnosis. Rather, the present invention may utilize an evaluation of the entire profile of markers. By plotting ROC curves for the sensitivity of a particular panel of markers versus 1-(specificity) for the panel at various cutoffs, a profile of marker measurements from a subject may be considered together to provide a global probability (expressed either as a numeric score or as a percentage risk) that the symptom(s) observed in an individual are caused by a partiuclar underlying disease. In such embodiments, an increase in a certain subset of markers may be sufficient to indicate a particular diagnosis in one patient, while an increase in a different subset of markers may be sufficient to indicate the same or a different diagnosis in another patient.

One or more markers may lack predictive value when considered alone, but when used as part of a panel, such markers may be of great value in determining a particular diagnosis. Weighting factors may also be applied to one or more markers in a panel, for example, when a marker is of particularly high utility in identifying a particular diagnosis. While the exemplary panels described herein can provide the ability to determine a diagnosis underlying, e.g., dyspnea, one or more markers may be replaced, added, or subtracted from these exemplary panels while still providing clinically useful results.

In yet other embodiments, multiple determinations of one or more markers can be made, and a temporal change in the markers can be used to rule in or out one or more particular etiologies for observed symptom(s). For example, one or more markers may be determined at an initial time, and again at a second time, and the change (or lack thereof) in the marker level(s) over time determined. In such embodiments, an increase in the marker from the initial time to the second time may be diagnostic of a particular disease underlying one or more symptoms. Likewise, a decrease in the marker from the initial time to the second time may be indicative of a particular disease underlying one or more symptoms.

In yet another embodiment, multiple determinations of one or more diagnostic or prognostic markers can be made, and a temporal change in the marker can be used to monitor the efficacy appropriate therapies. In such an embodiment, one might expect to see a decrease or an increase in the marker(s) over time during the course of effective therapy.

The skilled artisan will understand that, while in certain embodiments comparative measurements are made of the same diagnostic marker at multiple time points, one could also measure a given marker at one time point, and a second marker at a second time point, and a comparison of these markers may provide diagnostic information. Similarly, the skilled artisan will understand that serial measurements and changes in markers or the combined result over time may also be of diagnostic and/or prognostic value.

The skilled artisan will understand that associating one or more diagnostic markers with the presence or absence of a particular disease is a statistical analysis. For example, the presence or absence of a particular marker level may signal that a patient is more likely to suffer from a disease, as determined by a level of statistical significance. Statistical significance is often determined by comparing two or more populations, and determining a confidence interval and/or a p value. See, e.g., Dowdy and Wearden, *Statistics for Research*, John Wiley & Sons, New York, 1983. Preferred confidence intervals of the invention are 90%, 95%, 97.5%, 98%, 99%, 99.5%, 99.9% and 99.99%, while preferred p values are 0.1, 0.05, 0.025, 0.02, 0.01, 0.005, 0.001, and 0.0001.

In yet another aspect, the invention relates to methods for determining a treatment regimen for use in a subject. The methods preferably comprise identifying the underlying cause of one or more symptoms that, when considered in isolation, may be related to a plurality of possible underlying diseases or conditions as described herein. One or more treatment regimens can then be selected to treat the underlying disease in the subject.

In a related aspect, the invention relates to methods for determining a treatment regimen for use in a subject suffering from congestive heart failure. The methods preferably comprise performing the methods described herein to rule in or out systolic heart failure and/or diastolic heart failure, or to distinguish between these two causes of congestive heart failure. One or more treatment regimens can then be selected to treat the type of congestive heart failure in the subject.

In a further aspect, the invention relates to kits for identifying the underlying cause of one or more symptoms that, when considered in isolation, may be related to a plurality of possible underlying diseases or conditions. These kits preferably comprise devices and reagents for measuring one or more marker levels in a patient sample, and instructions for performing the assay. Optionally, the kits may contain one or more means for correlating marker level(s) in order to rule in or rule out one or more potential etiologies of the observed symptoms. Such kits preferably contain sufficient reagents to perform one or more such determinations, and/or Food and Drug Administration (FDA)-approved labeling.

In a related aspect, the invention relates to kits to rule in or out systolic heart failure and/or diastolic heart failure, or to distinguish between these two causes of congestive heart failure. These kits preferably comprise devices and reagents for measuring one or more marker levels in a patient sample, and instructions for performing the assay. Optionally, the kits may contain one or more means for correlating marker level(s) in order to distinguish between systolic heart failure and diastolic heart failure. Such kits preferably contain sufficient reagents to perform one or more such determinations, and/or Food and Drug Administration (FDA)-approved labeling.

In yet a further aspect, the invention relates to devices for identifying the underlying cause of one or more symptoms that, when considered in isolation, may be related to a plurality of possible underlying diseases or conditions. Such devices preferably contain a plurality of discrete, independently addressable locations, or "diagnostic zones," each of which is related to a particular marker of interest. Following reaction of a sample with the devices, a signal is generated from the diagnostic zone(s), which may then be correlated to the presence or amount of the markers of interest. Such markers may then be used to rule in or out one or more potential etiologies of the observed symptoms.

In a related aspect, the invention relates to devices to rule in or out systolic heart failure and/or diastolic heart failure, or to distinguish between these two causes of congestive heart failure. Such devices preferably contain a plurality of diagnostic zones, each of which is related to a particular marker of interest. Following reaction of a sample with the devices, a signal is generated from the diagnostic zone(s), which may then be correlated to the presence or amount of the markers of interest. Such markers may then be used to distinguish between systolic heart failure and diastolic heart failure.

DETAILED DESCRIPTION OF THE INVENTION

The present invention relates to methods and compositions for symptom-based differential diagnosis of diseases in subjects.

Patients presenting for medical treatment often exhibit one or a few primary observable changes in bodily characteristics or functions that are indicative of disease. Often, these "symptoms" are nonspecific, in that a number of potential diseases can present the same observable symptom or symptoms. A typical list of nonspecific symptoms might include one or more of the following: shortness of breath (or dyspnea), chest pain, fever, dizziness, and headache. These symptoms can be quite common, and the number of diseases that must be considered by the clinician can be astoundingly broad.

Taking shortness of breath (referred to clinically as "dyspnea") as an example, this symptom considered in isolation may be indicative of conditions as diverse as asthma, chronic obstructive pulmonary disease ("COPD"), tracheal stenosis, obstructive endobroncheal tumor, pulmonary fibrosis, pneumoconiosis, lymphangitic carcinomatosis, kyphoscoliosis, pleural effusion, amyotrophic lateral sclerosis, congestive heart failure, coronary artery disease, myocardial infarction, atrial fibrillation, cardiomyopathy, valvular dysfunction, left ventricle hypertrophy, pericarditis, arrhythmia, pulmonary embolism, metabolic acidosis, chronic bronchitis, pneumonia, anxiety, sepsis, aneurismic dissection, etc. See, e.g., *Kelley's Textbook of Internal Medicine*, 4th Ed., Lippincott Williams & Wilkins, Philadelphia, Pa., 2000, pp. 2349-2354, "Approach to the Patient With Dyspnea"; Mulrow et al., *J. Gen. Int. Med.* 8: 383-92 (1993).

Similarly, chest pain, when considered in isolation, may be indicative of stable. angina, unstable angina, myocardial ischemia, atrial fibrillation, myocardial infarction, musculoskeletal injury, cholecystitis, gastroesophageal reflux, pulmonary embolism, pericarditis, aortic dissection, pneumonia, anxiety, etc. Moreover, the classification of chest pain as stable or unstable angina (or even mild myocardial infarction) in cases other than definitive myocardial infarction is completely subjective. The diagnosis, and in this case the distinction, is made not by angiography, which may quantify the degree of arterial occlusion, but rather by a physician's interpretation of clinical symptoms.

Differential diagnosis refers to methods for diagnosing the particular disease(s) underlying the symptoms in a particular subject, based on a comparison of the characteristic features observable from the subject to the characteristic features of those potential diseases. Depending on the breadth of diseases that must be considered in the differential diagnosis, the types and number of tests that must be ordered by a clinician can be quite large. In the case of dyspnea for example, the clinician may order tests from a group that includes radiography, electrocardiogram, exercise treadmill testing, blood chemistry analysis, echocardiography, bronchoprovocation testing, spirometry, pulse oximetry, esophageal pH monitoring, laryngoscopy, computed tomography, histology, cytology, magnetic resonance imaging, etc. See, e.g., Morgan and Hodge, *Am. Fam. Physician* 57: 711-16 (1998). The clinician must then integrate information obtained from a battery of tests, leading to a clinical diagnosis that most closely represents the range of symptoms and/or diagnostic test results obtained for the subject.

The present invention describes methods and compositions that can assist in the differential diagnosis of one or more nonspecific symptoms by providing diagnostic markers that are designed to rule in or out one, and preferably a plurality, of possible etiologies for the observed symptoms. The concept of symptom-based differential diagnosis described herein can provide panels of diagnostic markers designed be considered in concert to distinguish between possible diseases that underlie a nonspecific symptom observed in a patient.

Definitions

The term "fever" refers to a body temperature greater than 100° C. orally or 100.8° C. rectally. In the case of fever, a plurality of markers are preferably selected to rule in or out a plurality of the following: sepsis; arteritis; sarcoidosis; and one or more infectious diseases, including infection by *Staphyloccus* species, *Nisseria* species, *Pneumococcal* species, *Listeria* species, *Anthrax, Nocardia* species, *Salmonella* species, *Shigella* species, *Haemophilus* species, *Brucella* species, *Vibrio* species including *V. cholerae, Franciscella tularensis, Yersinia pestis, Pseudomonas* species, *Clostridia* species including *C. tetani, C. perfringens, C. ramosum, C. botulinum*, and *C. septicum, Actinomyces*species, *Treponema pallidum, Borrelia* species including *B. burgdorferi, Leptospira* species, *Mycobacterium* species including *M. tuberculosis, M. bovis, M. leprae*, and *M. africanum, Histoplasma* species, *Escherichia coli, Coccidioides* species, *Blastomyces* species, *Paracoccidioides* species, *Sporothrix* species, *Cryptococcus* species, *Candida* species, and *Aspergillus* species; Rickettsial diseases including Rocky Mountain spotted fever, Q fever, typhus, trench fever, and cat-scratch fever; parasitic diseases including Malaria, Babesiosis, African sleeping sickness, Trypanosomiasis, Leishmaniasis, Toxoplasmosis, and Amebiasis; viral infection by influenza virus, parainfluenza virus, mumps virus, adenovirus, respiratory syncytial virus, rhinovirus, poliovirus, coxackievirus, echovirus, rubeola virus, rubella virus, parvovirus, hepatitis A, B, C, D, or E, cytomegalovirus, Epstein-Barr virus, Herpes simplex virus, Varicella-zoster virus, Alphavirus, Flaviviruses including yellow fever virus, dengue fever virus, Japanese encephalitis virus, and St. Louis encephalitis virus, West Nile virus, Colorado tick fever virus, Rabies virus, Arenavirus, Marburg agent, and Ebola virus.

The term "neurologic dysfunction" refers to a loss of one or more normal physiological or mental functions having a neurogenic etiology. The skilled artisan will understand that neurologic dysfunction is a common symptom in various systemic disorders (e.g., alcoholism, vascular disease, stroke, autoimmunity, metabolic disorders, aging, etc.). Specific neurologic dysfunctions include, but are not limited to, pain, headache, aphasia, apraxia, agnosia, amnesia, stupor, coma, delirium, dementia, seizure, migraine insomnia, hypersomnia, sleep apnea, tremor, dyskinesia, paralysis, etc.

The term "hypertension" refers to a systolic blood pressure of greater than or equal to 140 mm Hg and/or a diastolic blood pressure of greater than or equal to 90 mm Hg. Hypertension can include isolated systolic hypertension (i.e., no elevation in diastolic blood pressure). In the case of hypertension, the plurality of markers are preferably selected to rule in or out a plurality of the following: left ventricular failure, atherosclerosis, renal disease including chronic glomerulonephritis, and polycystic renal disease, coartation of the aorta, renal arteriall stenosis, and hyperparathyroidism.

The term "condition within the differential diagnosis of a symptom" as used herein refers to a pathologic state that is known to be causative of a particular perceptible change in one or more physical characteristics exhibited by a subject suffering from the pathologic state, as compared to a normal subject. The concept of differential diagnosis is well established to those of skill in the art. See, e.g., Beck, *Tutorials in Differential Diagnosis*, Churchill Livingstone, 2002; Zackon, *Pulmonary Differential Diagnosis*, Elsevier, 2000; Jamison, *Differential Diagnosis for Primary Practice*, Churchill Livingstone, 1999; Bouchier et al., *French's Index of Differential Diagnosis*, Oxford University Press, 1997.

The term "marker" as used herein refers to proteins, polypeptides, phospholipids, or small molecules to be used as targets for screening test samples obtained from subjects. "Proteins or polypeptides" used as markers in the present invention are contemplated to include any fragments thereof, in particular, immunologically detectable fragments. The term "related marker" as used herein refers to one or more fragments of a particular marker that may be detected as a surrogate for the marker itself. Preferably, the methods described hereinafter utilize one or more markers that are derived from the subject. The term "subject-derived marker" as used herein refers to protein, polypeptide, phospholipid, nucleic acid, prion, or small molecule markers that are expressed or produced by one or more cells of the subject. The presence, absence, or amount of one or more markers may indicate that a particular disease is present, or may indicate that a particular disease is absent. Additional markers may be used that are derived not from the subject, but rather that are expressed by pathogenic or infectious organisms that are correlated with a particular disease. Such markers are preferably protein, polypeptide, phospholipid, nucleic acid, prion, or small molecule markers that identify the infectious diseases described above.

The term "test sample" as used herein refers to a sample of bodily fluid obtained for the purpose of diagnosis, prognosis, or evaluation of a subject of interest, such as a patient. In certain embodiments, such a sample may be obtained for the purpose of determining the outcome of an ongoing condition or the effect of a treatment regimen on a condition. Preferred test samples include blood, serum, plasma, cerebrospinal fluid, urine, saliva, sputum, and pleural effusions. In addition, one of skill in the art would realize that some test samples would be more readily analyzed following a fractionation or purification procedure, for example, separation of whole blood into serum or plasma components.

As used herein, a "plurality" refers to at least two. Preferably, a plurality refers to at least 3, more preferably at least 5, even more preferably at least 10, even more preferably at least 15, and most preferably at least 20. In particularly preferred embodiments, a plurality is a large number, i.e., at least 100.

The term "subject" as used herein refers to a human or non-human organism. Thus, the methods and compositions described herein are applicable to both human and veterinary disease. Further, while a subject is preferably a living organism, the invention described herein may be used in postmortem analysis as well. Preferred subjects are "patients," i.e., living humans that are receiving medical care. This includes persons with no defined illness who are being investigated for signs of pathology.

The term "diagnosis" as used herein refers to methods by which the skilled artisan can estimate and/or determine whether or not a patient is suffering from a given disease or condition. The skilled artisan often makes a diagnosis on the basis of one or more diagnostic indicators, i.e., a marker, the presence, absence, or amount of which is indicative of the presence, severity, or absence of the condition.

Similarly, a prognosis is often determined by examining one or more "prognostic indicators." These are markers, the presence or amount of which in a patient (or a sample obtained from the patient) signal a probability that a given course or outcome will occur. For example, when one or more prognostic indicators reach a sufficiently high level in samples obtained from such patients, the level may signal that the patient is at an increased probability for experiencing a future stroke in comparison to a similar patient exhibiting a lower marker level. A level or a change in level of a prognostic indicator, which in turn is associated with an increased probability of morbidity or death, is referred to as being "associated with an increased predisposition to an adverse outcome" in a patient. Preferred prognostic markers can predict the onset of delayed neurologic deficits in a patient after stroke, or the chance of future stroke.

The term "correlating," as used herein in reference to the use of diagnostic and markers, refers to comparing the presence or amount of the marker(s) in a patient to its presence or amount in persons known to suffer from, or known to be at risk of, a given condition; or in persons known to be free of a given condition. As discussed above, a marker level in a patient sample can be compared to a level known to be associated with a specific diagnosis. The sample's marker level is said to have been correlated with a diagnosis; that is, the skilled artisan can use the marker level to determine whether the patient suffers from a specific type diagnosis, and respond accordingly. Alternatively, the sample's marker level can be compared to a marker level known to be associated with a good outcome (e.g., the absence of disease, etc.). In preferred embodiments, a profile of marker levels are correlated to a global probability or a particular outcome using ROC curves.

The phrase "determining the diagnosis" as used herein refers to methods by which the skilled artisan can determine the presence or absence of a particular disease in a patient. The term "diagnosis" does not refer to the ability to determine the presence or absence of a particular disease with 100% accuracy, or even that a given course or outcome is more likely to occur than not. Instead, the skilled artisan will understand that the term "diagnosis" refers to an increased probability that a certain disease is present in the subject. In preferred embodiments, a diagnosis indicates about a 5% increased chance that a disease is present, about a 10% chance, about a 15% chance, about a 20% chance, about a 25% chance, about a 30% chance, about a 40% chance, about a 50% chance, about a 60% chance, about a 75% chance, about a 90% chance, and about a 95% chance. The term "about" in this context refers to +/−2%.

The term "discrete" as used herein refers to areas of a surface that are non-contiguous. That is, two areas are discrete from one another if a border that is not part of either area completely surrounds each of the two areas.

The term "independently addressable" as used herein refers to discrete areas of a surface from which a specific signal may be obtained.

The term "antibody" as used herein refers to a peptide or polypeptide derived from, modeled after or substantially encoded by an immunoglobulin gene or immunoglobulin genes, or fragments thereof, capable of specifically binding an antigen or epitope. See, e.g. *Fundamental Immunology*, $3^{rd}$ Edition, W. E. Paul, ed., Raven Press, N.Y. (1993); Wilson (1994) *J. Immunol. Methods* 175:267-273; Yarmush (1992) *J. Biochem. Biophys. Methods* 25:85-97. The term antibody includes antigen-binding portions, i.e., "antigen binding sites," (e.g., fragments, subsequences, complementarity determining regions (CDRs)) that retain capacity to bind antigen, including (i) a Fab fragment, a monovalent fragment consisting of the VL, VH, CL and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) *Nature* 341:544-546), which consists of a VH domain; and (vi) an isolated complementarity determining region (CDR). Single chain antibodies are also included by reference in the term "antibody."

Identification of Marker Panels

In accordance with the present invention, there are provided methods and systems for the identification of a one or more markers for the differential diagnosis of one or more nonspecific symptoms exhibited by a subject. Suitable methods for identifying markers useful for the diagnosis of disease states are described in detail in U.S. Provisional Patent Application No. 60/436,392, entitled METHOD AND SYSTEM FOR DISEASE DETECTION USING MARKER COMBI- NATIONS, filed Dec. 24, 2002, and U.S. patent application Ser. No. 10/331,127, entitled METHOD AND SYSTEM FOR DISEASE DETECTION USING MARKER COMBINATIONS, filed Dec. 27, 2002, each of which is hereby incorporated by reference in its entirety, including all tables, figures, and claims.

One skilled in the art will also recognize that univariate analysis of markers can be performed and the data from the univariate analyses of multiple markers can be combined to form panels of markers to differentiate different disease conditions. In forming panels of markers to define the cause of dypsnea, for example, markers related to each cause of dypsnea should be considered.

In developing a panel of markers useful in differential diagnosis, data for a number of potential markers may be obtained from a group of subjects by testing for the presence or level of certain markers. The group of subjects is divided into two sets. The first set includes subjects who have been confirmed as having a disease or, more generally, being in a first condition state. For example, this first set of patients may be those that have recently had a stroke. The confirmation of this condition state may be made through a more rigorous and/or expensive testing. confirm the condition state. Hereinafter, subjects in this first set will be referred to as "diseased".

The second set of subjects are simply those who do not fall within the first set. Subjects in this second set will hereinafter be referred to as "non-diseased". Preferably, the first set and the second set each have an approximately equal number of subjects.

The data obtained from subjects in these sets includes levels of a plurality of markers. Preferably, data for the same set of markers is available for each patient. This set of markers may include all candidate markers which may be suspected as being relevant to the detection of a particular disease or condition. Actual known relevance is not required. Embodiments of the methods and systems described herein may be used to determine which of the candidate markers are most relevant to the diagnosis of the disease or condition. The levels of each marker in the two sets of subjects may be distributed across a broad range, e.g., as a Gaussian distribution. However, no distribution fit is required.

As noted above, a marker often is incapable of definitively identifying a patient as either diseased or non-diseased. For example, if a patient is measured as having a marker level that falls within the overlapping region, the results of the test will be useless in diagnosing the patient. An artificial cutoff may be used to distinguish between a positive and a negative test result for the detection of the disease or condition. Regardless of where the cutoff is selected, the effectiveness of the single marker as a diagnosis tool is unaffected. Changing the cutoff merely trades off between the number of false positives and the number of false negatives resulting from the use of the single marker. The effectiveness of a test having such an overlap is often expressed using a ROC (Receiver Operating Characteristic) curve. ROC curves are well known to those skilled in the art.

The horizontal axis of the ROC curve represents (1-specificity), which increases with the rate of false positives. The vertical axis of the curve represents sensitivity, which increases with the rate of true positives. Thus, for a particular cutoff selected, the value of (1-specificity) may be determined, and a corresponding sensitivity may be obtained. The area under the ROC curve is a measure of the probability that the measured marker level will allow correct identification of a disease or condition. Thus, the area under the ROC curve can be used to determine the effectiveness of the test.

As discussed above, the measurement of the level of a single marker may have limited usefulness. The measurement of additional markers provides additional information, but the difficulty lies in properly combining the levels of two potentially unrelated measurements. In the methods and systems according to embodiments of the present invention, data relating to levels of various markers for the sets of diseased and non-diseased patients may be used to develop a panel of markers to provide a useful panel response. The data may be provided in a database such as Microsoft Access, Oracle, other SQL databases or simply in a data file. The database or data file may contain, for example, a patient identifier such as a name or number, the levels of the various markers present, and whether the patient is diseased or non-diseased.

Next, an artificial cutoff region may be initially selected for each marker. The location of the cutoff region may initially be selected at any point, but the selection may affect the optimization process described below. In this regard, selection near a suspected optimal location may facilitate faster convergence of the optimizer. In a preferred method, the cutoff region is initially centered about the center of the overlap region of the two sets of patients. In one embodiment, the cutoff region may simply be a cutoff point. In other embodiments, the cutoff region may have a length of greater than zero. In this regard, the cutoff region may be defined by a center value and a magnitude of length. In practice, the initial selection of the limits of the cutoff region may be determined according to a pre-selected percentile of each set of subjects. For example, a point above which a pre-selected percentile of diseased patients are measured may be used as the right (upper) end of the cutoff range.

Each marker value for each patient may then be mapped to an indicator. The indicator is assigned one value below the cutoff region and another value above the cutoff region. For example, if a marker generally has a lower value for non-diseased patients and a higher value for diseased patients, a zero indicator will be assigned to a low value for a particular marker, indicating a potentially low likelihood of a positive diagnosis. In other embodiments, the indicator may be calculated based on a polynomial. The coefficients of the polynomial may be determined based on the distributions of the marker values among the diseased and non-diseased subjects.

The relative importance of the various markers may be indicated by a weighting factor. The weighting factor may initially be assigned as a coefficient for each marker. As with the cutoff region, the initial selection of the weighting factor may be selected at any acceptable value, but the selection may affect the optimization process. In this regard, selection near a suspected optimal location may facilitate faster convergence of the optimizer. In a preferred method, acceptable weighting coefficients may range between zero and one, and an initial weighting coefficient for each marker may be assigned as 0.5. In a preferred embodiment, the initial weighting coefficient for each marker may be associated with the effectiveness of that marker by itself. For example, a ROC curve may be generated for the single marker, and the area under the ROC curve may be used as the initial weighting coefficient for that marker.

Next, a panel response may be calculated for each subject in each of the two sets. The panel response is a function of the indicators to which each marker level is mapped and the weighting coefficients for each marker. In a preferred embodiment, the panel response (R) for a each subject (j) is expressed as:

$$R_j = \Sigma w_i I_{i,j},$$

where i is the marker index, j is the subject index, $w_i$ is the weighting coefficient for marker i, I is the indicator value to which the marker level for marker i is mapped for subject j, and $\Sigma$ is the summation over all candidate markers i.

One advantage of using an indicator value rather than the marker value is that an extraordinarily high or low marker levels do not change the probability of a diagnosis of diseased or non-diseased for that particular marker. Typically, a marker value above a certain level generally indicates a certain condition state. Marker values above that level indicate the condition state with the same certainty. Thus, an extraordinarily high marker value may not indicate an extraordinarily high probability of that condition state. The use of an indicator which is constant on one side of the cutoff region eliminates this concern.

The panel response may also be a general function of several parameters including the marker levels and other factors including, for example, race and gender of the patient. Other factors contributing to the panel response may include the slope of the value of a particular marker over time. For example, a patient may be measured when first arriving at the hospital for a particular marker. The same marker may be measured again an hour later, and the level of change may be reflected in the panel response. Further, additional markers may be derived from other markers and may contribute to the value of the panel response. For example, the ratio of values of two markers may be a factor in calculating the panel response.

Having obtained panel responses for each subject in each set of subjects, the distribution of the panel responses for each set may now be analyzed. An objective function may be defined to facilitate the selection of an effective panel. The objective function should generally be indicative of the effectiveness of the panel, as may be expressed by, for example, overlap of the panel responses of the diseased set of subjects and the panel responses of the non-diseased set of subjects. In this manner, the objective function may be optimized to maximize the effectiveness of the panel by, for example, minimizing the overlap.

In a preferred embodiment, the ROC curve representing the panel responses of the two sets of subjects may be used to define the objective function. For example, the objective function may reflect the area under the ROC curve. By maximizing the area under the curve, one may maximize the effectiveness of the panel of markers. In other embodiments, other features of the ROC curve may be used to define the objective function. For example, the point at which the slope of the ROC curve is equal to one may be a useful feature. In other embodiments, the point at which the product of sensitivity and specificity is a maximum, sometimes referred to as the "knee," may be used. In an embodiment, the sensitivity at the knee may be maximized. In further embodiments, the sensitivity at a predetermined specificity level may be used to define the objective function. Other embodiments may use the specificity at a predetermined sensitivity level may be used. In still other embodiments, combinations of two or more of these ROC-curve features may be used.

It is possible that one of the markers in the panel is specific to the disease or condition being diagnosed. When such markers are present at above or below a certain threshold, the panel response may be set to return a "positive" test result. When the threshold is not satisfied, however, the levels of the marker may nevertheless be used as possible contributors to the objective function.

An optimization algorithm may be used to maximize or minimize the objective function. Optimization algorithms are well-known to those skilled in the art and include several commonly available minimizing or maximizing functions including the Simplex method and other constrained optimization techniques. It is understood by those skilled in the art that some minimization functions are better than others at searching for global minimums, rather than local minimums. In the optimization process, the location and size of the cutoff region for each marker may be allowed to vary to provide at least two degrees of freedom per marker. Such variable parameters are referred to herein as independent variables. In a preferred embodiment, the weighting coefficient for each marker is also allowed to vary across iterations of the optimization algorithm. In various embodiments, any permutation of these parameters may be used as independent variables.

In addition to the above-described parameters, the sense of each marker may also be used as an independent variable. For example, in many cases, it may not be known whether a higher level for a certain marker is generally indicative of a diseased state or a non-diseased state. In such a case, it may be useful to allow the optimization process to search on both sides. In practice, this may be implemented in several ways. For example, in one embodiment, the sense may be a truly separate independent variable which may be flipped between positive and negative by the optimization process. Alternatively, the sense may be implemented by allowing the weighting coefficient to be negative.

The optimization algorithm may be provided with certain constraints as well. For example, the resulting ROC curve may be constrained to provide an area-under-curve of greater than a particular value. ROC curves having an area under the curve of 0.5 indicate complete randomness, while an area under the curve of 1.0 reflects perfect separation of the two sets. Thus, a minimum acceptable value, such as 0.75, may be used as a constraint, particularly if the objective function does not incorporate the area under the curve. Other constraints may include limitations on the weighting coefficients of particular markers. Additional constraints may limit the sum of all the weighting coefficients to a particular value, such as 1.0.

The iterations of the optimization algorithm generally vary the independent parameters to satisfy the constraints while minimizing or maximizing the objective function. The number of iterations may be limited in the optimization process. Further, the optimization process may be terminated when the difference in the objective function between two consecutive iterations is below a predetermined threshold, thereby indicating that the optimization algorithm has reached a region of a local minimum or a maximum.

Thus, the optimization process may provide a panel of markers including weighting coefficients for each marker and cutoff regions for the mapping of marker values to indicators. In order to develop lower-cost panels which require the measurement of fewer marker levels, certain markers may be eliminated from the panel. In this regard, the effective contribution of each marker in the panel may be determined to identify the relative importance of the markers. In one embodiment, the weighting coefficients resulting from the optimization process may be used to determine the relative importance of each marker. The markers with the lowest coefficients may be eliminated.

In certain cases, the lower weighting coefficients may not be indicative of a low importance. Similarly, a higher weighting coefficient may not be indicative of a high importance. For example, the optimization process may result in a high coefficient if the associated marker is irrelevant to the diagnosis. In this instance, there may not be any advantage that will drive the coefficient lower. Varying this coefficient may not affect the value of the objective function.

Exemplary Marker Panels

The present invention is described hereinafter generally in terms of the differential diagnosis of diseases related to dyspnea. The skilled artisan will understand, however, that the concepts of symptom-based differential diagnosis described herein are generally applicable to any physical characteristics that are indicative of a plurality of possible etiologies such as fever, neurologic dysfunction, chest pain ("angina"), dizzyness, headache, etc.

A first step in the identification of suitable markers for symptom-bases differential diagnosis requires a consideration of the possible diagnoses that may be causative of the non-specific symptom observed. In the case of dyspnea, the potential causes are myriad. In a preferred embodiment, the following discussion considers three potential diagnoses: congestive heart failure, pulmonary embolism, and myocardial infarction; and three potential markers for inclusion in a differential diagnosis panel for these potential diagnoses: BNP, D-dimer, and cardiac troponin, respecitively. In another preferred embodiement, markers for three potential diagnoses, congestive heart failure, pulmonary embolism, and myocardial infarction include three potential markers in a differential diagnosis panel, BNP related peptides, D-dimer, and cardiac troponin, respecitively. In a preferred embodiment, three potential diagnoses in the case of dyspnea include congestive heart failure, pulmonary embolism, and myocaridal infarction. In a second preferred embodiment, four potential diagnoses in the case of dyspnea include congestive heart failure, pulmonary embolism, and myocaridal infarction, and atrial fibrillation. Potential markers for inclusion in a differential diagnosis panel include one or more of the following: BNP (heart failure), BNP related peptides (heart failure), D-dimer (pulmonary embolism), cardiac troponin (myocardial infarction), ANP (atrial fibrillation), and ANP related peptides (atrial fibrillation).

BNP

B-type natriuretic peptide (BNP), also called brain-type natriuretic peptide is a 32 amino acid, 4 kDa peptide that is involved in the natriuresis system to regulate blood pressure and fluid balance. Bonow, R. O., Circulation 93:1946-1950 (1996). The precursor to BNP is synthesized as a 108-amino acid molecule, referred to as "pre pro BNP," that is proteolytically processed into a 76-amino acid N-terminal peptide (amino acids 1-76), referred to as "NT pro BNP" and the 32-amino acid mature hormone, referred to as BNP or BNP 32 (amino acids 77-108). It has been suggested that each of these species—NT pro-BNP, BNP-32, and the pre pro BNP—can circulate in human plasma. Tateyama et al., Biochem. Biophys. Res. Commun. 185: 760-7 (1992); Hunt et al., Biochem. Biophys. Res. Commun. 214: 1175-83 (1995). The 2 forms, pre pro BNP and NT pro BNP, and peptides which are derived from BNP, pre pro BNP and NT pro BNP and which are present in the blood as a result of proteolyses of BNP, NT pro BNP and pre pro BNP, are collectively described as markers related to or associated with BNP.

The term "BNP" as used herein refers to the mature 32-amino acid BNP molecule itself. As the skilled artisan will recognize, however, because of its relationship to BNP, the concentration of NT pro-BNP molecule can also provide diagnostic or prognostic information in patients. The phrases "marker related to BNP" or "BNP related peptide" refers to any polypeptide that originates from the pre pro-BNP molecule, other than the 32-amino acid BNP molecule itself. Proteolytic degradation of BNP and of peptides related to BNP have also been described in the literature and these proteolytic fragments are also encompassed it the term "BNP related peptides."

BNP and BNP-related peptides are predominantly found in the secretory granules of the cardiac ventricles, and are released from the heart in response to both ventricular volume expansion and pressure overload. Wilkins, M. et al., Lancet 349: 1307-10 (1997). Elevations of BNP are associated with raised atrial and pulmonary wedge pressures, reduced ventricular systolic and diastolic function, left ventricular hypertrophy, and myocardial infarction. Sagnella, G. A., Clinical Science 95: 519-29 (1998). Furthermore, there are numerous reports of elevated BNP concentration associated with congestive heart failure and renal failure. Thus, BNP levels in a patient may be indicative of several possible underlying causes of dyspnea.

D-dimer

D-dimer is a crosslinked fibrin degradation product with an approximate molecular mass of 200 kDa. The normal plasma concentration of D-dimer is <150 ng/ml (750 pM). The plasma concentration of D-dimer is elevated in patients with acute myocardial infarction and unstable angina, but not stable angina. Hoffmeister, H. M. et al., Circulation 91: 2520-27 (1995); Bayes-Genis, A. et al., Thromb. Haemost. 81: 865-68 (1999); Gurfinkel, E. et al, Br. Heart J. 71: 151-55 (1994); Kruskal, J. B. et al., N. Engl. J. Med. 317: 1361-65 (1987); Tanaka, M. and Suzuki, A., Thromb. Res. 76: 289-98 (1994).

The plasma concentration of D-dimer also will be elevated during any condition associated with coagulation and fibrinolysis activation, including stroke, surgery, atherosclerosis, trauma, and thrombotic thrombocytopenic purpura. D-dimer is released into the bloodstream immediately following proteolytic clot dissolution by plasmin. The plasma concentration of D-dimer can exceed 2 µg/ml in patients with unstable angina. Gurfinkel, E. et al., Br. Heart J. 71: 151-55 (1994). Plasma D-dimer is a specific marker of fibrinolysis and indicates the presence of a prothrombotic state associated with acute myocardial infarction and unstable angina. The plasma concentration of D-dimer is also nearly always elevated in patients with acute pulmonary embolism; thus, normal levels of D-dimer may allow the exclusion of pulmonary embolism. Egermayer et al., Thorax 53: 830-34 (1998).

Cardiac Troponin

Troponin I (TnI) is a 25 kDa inhibitory element of the troponin complex, found in muscle tissue. TnI binds to actin in the absence of $Ca^{2+}$, inhibiting the ATPase activity of actomyosin. A TnI isoform that is found in cardiac tissue (cTnI) is 40% divergent from skeletal muscle TnI, allowing both isoforms to be immunologically distinguished. The normal plasma concentration of cTnI is <0.1 ng/ml (4 pM). cTnI is released into the bloodstream following cardiac cell death; thus, the plasma cTnI concentration is elevated in patients with acute myocardial infarction. Investigations into changes in the plasma cTnI concentration in patients with unstable angina have yielded mixed results, but cTnI is not elevated in the plasma of individuals with stable angina. Benamer, H. et al., Am. J. Cardiol. 82: 845-50 (1998); Bertinchant, J. P. et al., Clin. Biochem. 29: 587-94 (1996); Tanasijevic, M. J. et al., Clin. Cardiol. 22: 13-16 (1999); Musso, P. et al., J. Ital. Cardiol. 26: 1013-23 (1996); Holvoet, P. et al., JAMA 281: 1718-21 (1999); Holvoet, P. et al., Circulation 98: 1487-94 (1998).

The plasma concentration of cTnI in patients with acute myocardial infarction is significantly elevated 4-6 hours after onset, peaks between 12-16 hours, and can remain elevated for one week. The release kinetics of cTnI associated with unstable angina may be similar. The measurement of specific forms of cardiac troponin, including free cardiac troponin I and complexes of cardiac troponin I with troponin C and/or T may provide the user with the ability to identify various stages of ACS. Free and complexed cardiac-troponin T may be used in a manner analogous to that described for cardiac troponin I. Cardiac troponin T complex may be useful either alone or when expressed as a ratio with total cardiac troponin I to provide information related to the presence of progressing myocardial damage. Ongoing ischemia may result in the release of the cardiac troponin TIC complex, indicating that higher ratios of cardiac troponin TIC:total cardiac troponin I may be indicative of continual damage caused by unresolved ischemia. See, U.S. Pat. Nos. 6,147,688, 6,156,521, 5,947,124, and 5,795,725, which are hereby incorporated by reference in their entirety, including all tables, figures, and claims. One skilled in the art recognizes that in measuring cardiac troponin, one can measure the different isoforms of troponin I and troponin T.

One skilled in the art recognizes that in measuring cardiac troponin, one can measure the different isoforms of troponin I and troponin T. Thus, one may preferably measure free cardiac troponin I, free cardiac troponin T, cardiac troponin I in a complex comprising one or both of troponin T and troponin C, cardiac troponin T in a complex comprising one or both of troponin I and troponin C, total cardiac troponin I (meaning free and complexed cardiac troponin I), and/or total cardiac troponin T, The term "at least one cardiac troponin form" as used herein refers to any one of these foregoing forms.

ANP

A-type natriuretic peptide (ANP) (also referred to as atrial natriuretic peptide or cardiodilatin Forssmann et al *Histochem Cell Biol* 110: 335-357 (1998)) is a 28 amino acid peptide that is synthesized, stored, and released atrial myocytes in response to atrial distension, angiotensin II stimulation, endothelin, and sympathetic stimulation (beta-adrenoceptor mediated). ANP is synthesized as a precursor molecule (pro-ANP) that is converted to an active form, ANP, by proteolytic cleavage and also forming N-terminal ANP (1-98). N-terminal ANP and ANP-have been reported to increase in patients exhibiting atrial fibrillation and heart failure (Rossi et al. *Journal of the American College of Cardiology* 35: 1256-62 (2000). In addition to atrial natriuretic peptide (ANP99-126) itself, linear peptide fragments from its N-terminal prohormone segment have also been reported to have biological activity. As the skilled artisan will recognize, however, because of its relationship to ANP, the concentration of N-terminal ANP molecule can also provide diagnostic or prognostic information in patients. The phrase "marker related to ANP or ANP related peptide" refers to any polypeptide that originates from the pro-ANP molecule (1-126), other than the 28-amino acid ANP molecule itself. Proteolytic degradation of ANP and of peptides related to ANP have also been described in the literature and these proteolytic fragments are also encompassed it the term "ANP related peptides."

Elevated levels of ANP are found during hypervolemia, atrial fibrillation and congestive heart failure. ANP is involved in the long-term regulation of sodium and water balance, blood volume and arterial pressure. This hormone decreases aldosterone release by the adrenal cortex, increases glomerular filtration rate (GFR), produces natriuresis and diuresis (potassium sparing), and decreases renin release thereby decreasing angiotensin II. These actions contribute to reductions in blood volume and therefore central venous pressure (CVP), cardiac output, and arterial blood pressure. Several isoforms of ANP have been identified, and their relationship to stroke incidence studied. See, e.g., Rubatu et al., *Circulation* 100:1722-6, 1999; Estrada et al., *Am. J. Hypertens.* 7:1085-9, 1994.

Chronic elevations of ANP appear to decrease arterial blood pressure primarily by decreasing systemic vascular resistance. The mechanism of systemic vasodilation may involve ANP receptor-mediated elevations in vascular smooth muscle cGMP as well as by attenuating sympathetic vascular tone. This latter mechanism may involve ANP acting upon sites within the central nervous system as well as through inhibition of norepinephrine release by sympathetic nerve terminals. ANP may be viewed as a counter-regulatory system for the renin-angiotensin system. A new class of drugs that are neutral endopeptidase (NEP) inhibitors have demonstrated efficacy in heart failure. These drugs inhibit neutral endopeptidase, the enzyme responsible for the degradation of ANP, and thereby elevate plasma levels of ANP. NEP inhibition is particularly effective in heart failure when the drug has a combination of both NEP and ACE inhibitor properties.

Based on the foregoing discussion, the skilled artisan will recognize that, for example, increased BNP is indicative of congestive heart failure, but may also be indicative of other cardiac-related conditions such as myocardial infarction. Thus, the inclusion of a marker related to myocardial injury such as cardiac troponin I and/or cardiac troponin T can permit further discrimination of the disease underlying the observed dyspnea and the increased BNP level. In this case, an increased level of cardiac troponin may be used to rule in myocardial infarction.

Similarly, BNP may also be indicative of pulmonary embolism. The inclusion of a marker related to coagulation and hemostasis such as D-dimer can permit further discrimination of the disease underlying the observed dyspnea and the increased BNP level. In this case, a normal level of D-dimer may be used to rule out pulmonary embolism.

A detailed analysis of this exemplary marker panel is provided in the following examples. The skilled artisan will readily acknowledge that other markers may be substituted in or added to this marker panel to further discriminate the causes of dyspnea in accordance with the methods for identification and use of diagnostic markers described herein. Additional suitable markers are described in the following sections.

As discussed in detail herein, the foregoing principles of marker panel design may be applied broadly to symptom-based differential diagnosis. For example, in the case of abdominal pain, the plurality of markers are preferably selected to rule in or out a plurality of the following: aortic dissection, mesenteric embolism, pancreatitis, appendicitis, angina, myocardial infarction, one or more infectious diseases described above, influenza, esophageal carcinoma, gastric adenocarcinoma, colorectal adenocarcinoma, pancreatic tumors including ductal adenocarcinoma, cystadenocarcinoma, and insulinoma. In a preferred embodiment, the potential diagnoses for abdominal pain include aortic aneurysm, mesenteric embolism, pancreatitis, appendicitis, angina and myocardial infarction.

The foregoing principles may also be applied to subdivide differential diagnosis to a given level of detail required by the clinical artisan. For example, the differential diagnosis of various symptoms may require discrimination between heart failure and atrial fibrillation. An exemplary marker panel for performing such discrimination preferably includes BNP or BNP related peptides, and ANP or ANP related peptides, respectively. Additional markers may be defined to distinguish between systolic and diastolic dysfunction and atrial fibrillation. Preferred markers in this case include BNP, calcitonin gene related peptide, calcitonin and urotensin 1 for differentiation of systolic and diastolic dysfunction and ANP or ANP related peptides for the detection of atrial fibrillation.

Likewise, markers may be defined to distinguish between systolic and diastolic dysfunction, atrial fibrillation, myocardial ischemia and cardiac necrosis. Preferred markers in this case include BNP, calcitonin gene related peptide, calcitonin and urotensin 1 for differentiation of systolic and diastolic dysfunction and ANP or ANP related peptides for the detection of atrial fibrillation and BNP and cardiac troponins for the detection of myocardial ischemia and necrosis.

In the case of chest pain, the present invention can provide markers able to distinguish between aortic dissection, myocardial ischemia, and cardiac necrosis; markers able to distinguish between aortic dissection, myocardial ischemia, and myocardial infarction; markers able to distinguish between aortic dissection, myocardial ischemia, cardiac necrosis and heart failure; markers able to distinguish between aortic dissection, myocardial ischemia, cardiac necrosis and myocardial infarction; markers able to distinguish between aortic dissection, myocardial ischemia, cardiac necrosis and atrial fibrillation; and/or markers able to distinguish between aortic dissection, myocardial ischemia and cardiac necrosis, myocardial infarction and atrial fibrillation. In accordance with the foregoing, a particularly preferred marker for aortic dissection is smooth muscle myosin, and most preferably smooth muscle myosin heavy chain, and a particularly preferred marker for atrial fibrillation is ANP or an ANP-related marker.

Preferred marker sets are those comprising smooth muscle myosin heavy chain and ANP or an ANP-related marker to distinguish aortic dissection and atrial fibrillation, respectively; smooth muscle myosin heavy chain, ANP or an ANP-related marker, and BNP or a BNP-related marker to distinguish aortic dissection, atrial fibrillation and myocardial ischemia, respectively; smooth muscle myosin heavy chain, BNP or a BNP-related marker, and a cardiac troponin form to distinguish aortic dissection, myocardial ischemia, and myocardial infarction, respectively; and smooth muscle myosin heavy chain, BNP or a BNP-related marker, creatine kinase MB, myoglobin, and a cardiac troponin form to distinguish aortic dissection, myocardial ischemia, cardiac necrosis, and myocardial infarction.

Similarly, in the case of disturbanes of metabolic state, the plurality of markers are preferably selected to rule in or out a plurality of the following: diabetes mellitus, diabetic ketoacidosis, alcoholic ketoacidosis, respiratory acidosis, respiratory alkalosis, nonketogenic hyperglycemia, hypoglycemia, renal failure, interstitial renal disease, COPD, pneumonia, pulmonary edema and asthma.

In the case of neurologic dysfunction, the plurality of markers are preferably selected to rule in or out a plurality of the following: stroke, brain tumor, cerebral hypoxia, hypoglycemia, migraine, atrial fibrillation, myocardial infarction, cardiac ischemia, peripheral vascular disease and seizure. Preferred markers in this case include specific markers of cerebral injury such as adenylate kinase, brain-derived neurotrophic factor, calbindin-D, creatine kinase-BB, glial fibrillary acidic protein, lactate dehydrogenase, myelin basic protein, neural cell adhesion molecule, neuron-specific enolase, neurotrophin-3, proteolipid protein, S-100β, thrombomodulin, protein kinase C gamma; and/or one or more non-specific markers of cerebral injury such as β-thromboglobulin, D-dimer, fibrinopeptide A, plasmin-α-2-antiplasmin complex, platelet factor 4, prothrombin fragment 1+2, thrombin-antithrombin III complex, tissue factor, von Willebrand factor, adrenomedullin, cardiac troponin I (for myocardial ischemia and necrosis), head activator, hemoglobin α2 chain, caspase-3, vascular endothelial growth factor (VEGF), one or more endothelins (e.g., endothelin-1, endothelin-2, and endothelin-3), interleukin-8, Atrial natriuretic peptide, B-type natriuretic peptide (for myocardial ischemia and necrosis), and C-type natriuretic peptide; and/or one or more acute phase reactants such as C-reactive protein, ceruloplasmin, fibrinogen, α1-acid glycoprotein, α1-antitrypsin, haptoglobin, insulin-like growth factor-1, interleukin-1β, interleukin-1 receptor antagonist, interleukin-6, transforming growth factor β, tumor necrosis factor α, E-selectin, intercellular adhesion molecule-1, matrix metalloproteinases (e.g., matrix metalloproteinase 9 (MMP-9)), monocyte chemotactic protein-1, and vascular cell adhesion molecule.

Methods and marker sets for differential diagnosis of stroke and other cerebral injuries are described in U.S. patent Ser. No. 10/225,082, filed Aug. 20, 2002, which is hereby incorporated in its entirety, including all tables figures and claims. As described therein, preferred marker panels diagnose and/or differentiate between stroke, subarachnoid hemorrhage, intracerebral hemorrhage, and/or hemorrhagic stroke; and/or can distinguish between ischemic and hemorrhagic stroke. Particularly preferred are markers that differentiate between thrombotic, embolic, lacunar, hypoperfusion, intracerebral hemorrhage, and subarachnoid hemorrhage types of strokes. Particularly preferred marker sets include BNP, IL-6, S-100β, MMP-9, TAT complex, and vWF A1-integrin; BNP, S-100β, MMP-9, and vWF-A1-integrin; vWF-A1, VEGF, and MMP-9; caspase-3, MMP-9, and GFAP; caspase-3, MMP-9, vWF-A1, and BNP; NCAM, BDNF, Caspase-3, MMP-9, vWF-A1, and VEGF; NCAM, BDNF, Caspase-3, MMP-9, vWF-A1, and S-100β; VEGF; NCAM, BDNF, Caspase-3, MMP-9, vWF-A1, and MCP-1; VEGF; NCAM, BDNF, Caspase-3, MMP-9, VEGF, and vWF A1-integrin; BDNF, MMP-9, S-100β, vWF A1-integrin, MCP-1, and GFAP; BDNF, caspase-3, MMP-9, vWF-A1, S-100β, and GFAP; NCAM, BDNF, MMP-9, vWF-A1, S-100β, and GFAP; NCAM, BDNF, caspase-3, MMP-9, S-100β, and GFAP; caspase-3, NCAM, MCP-1, S100β, MMP-9, vWF A1-integrin, and BNP; caspase-3, NCAM, MCP-1, S100β, MMP-9, vWF A1, BNP, and GFAP; CRP, NT-3, vWF, MMP-9, VEGF, and CKBB; CRP, MMP-9, VEGF, CKBB, and MCP-1; CRP, NT-3, MMP-9, VEGF, CKBB, and MCP-1; and CRP, MMP-9, VEGF, CKBB, MCP-1. Calbindin, vWF VP1, vWF A3, vWF A1-A3, TAT complex, proteolipid protein, IL-6, IL-8, myelin basic protein, S-100β, tissue factor, GFAP, vWF A1-integrin, CNP, and NCAM.

A panel consisting of the markers referenced herein may be constructed to provide relevant information related to the differential diagnosis of interest. Such a panel may be constructed using 1, 2, 3, 4, 5, 6, 7, 8, 9, 10, 11, 12, 13, 14, 15, 16, 17, 18, 19 or 20 individual markers. The analysis of a single marker or subsets of markers comprising a larger panel of markers could be carried out by one skilled in the art to optimize clinical sensitivity or specificity in various clinical settings. These include, but are not limited to ambulatory, urgent care, critical care, intensive care, monitoring unit, inpatient, outpatient, physician office, medical clinic, and health screening settings. Furthermore, one skilled in the art can use a single marker or a subset of markers comprising a larger panel of markers in combination with an adjustment of the diagnostic threshold in each of the aforementioned settings to optimize clinical sensitivity and specificity. The clinical sensitivity of an assay is defined as the percentage of those with the disease that the assay correctly predicts, and the specificity of an assay is defined as the percentage of those without the disease that the assay corrects predicts (Tietz Textbook of Clinical Chemistry, $2^{nd}$ edition, Carl Burtis and Edward Ashwood eds., W. B. Saunders and Company, p.

496). The following provides a brief discussion of additional exemplary markers for use in identifying suitable marker panels by the methods described herein.

(i) Exemplary Markers Related to Myocardial Injury

Annexin V, also called lipocortin V, endonexin II, calphobindin I, calcium binding protein 33, placental anticoagulant protein I, thromboplastin inhibitor, vascular anticoagulant-α, and anchorin CII, is a 33 kDa calcium-binding protein that is an indirect inhibitor and regulator of tissue factor. Annexin V is composed of four homologous repeats with a consensus sequence common to all annexin family members, binds calcium and phosphatidyl serine, and is expressed in a wide variety of tissues, including heart, skeletal muscle, liver, and endothelial cells (Giambanco, I. et al., *J. Histochem. Cytochem*. 39:P1189-1198, 1991; Doubell, A. F. et al., *Cardiovasc. Res*. 27:1359-1367, 1993). The normal plasma concentration of annexin V is <2 ng/ml (Kaneko, N. et al., *Clin. Chim. Acta* 251:65-80, 1996). The plasma concentration of annexin V is elevated in individuals with acute myocardial infarction (Kaneko, N. et al., *Clin. Chim. Acta* 251:65-80, 1996). Due to its wide tissue distribution, elevation of the plasma concentration of annexin V may be associated with any condition involving non-cardiac tissue injury. However, one study has found that plasma annexin V concentrations were not significantly elevated in patients with old myocardial infarction, chest pain syndrome, valvular heart disease, lung disease, and kidney disease (Kaneko, N. et al., *Clin. Chim. Acta* 251:65-80, 1996). Annexin V is released into the bloodstream soon after acute myocardial infarction onset. The annexin V concentration in the plasma of acute myocardial infarction patients decreased from initial (admission) values, suggesting that it is rapidly cleared from the bloodstream (Kaneko, N. et al., *Clin. Chim. Acta* 251:65-80, 1996).

Enolase is a 78 kDa homo- or heterodimeric cytosolic protein produced from α, β, and γ subunits. Enolase catalyzes the interconversion of 2-phosphoglycerate and phosphoenolpyruvate in the glycolytic pathway. Enolase is present as αα, αβ, ββ, αγ, and γγ isoforms. The a subunit is found in most tissues, the β subunit is found in cardiac and skeletal muscle, and the γ subunit is found primarily in neuronal and neuroendocrine tissues. β-enolase is composed of αβ and ββ enolase, and is specific for muscle. The normal plasma concentration of β-enolase is <10 ng/ml (120 pM). β-enolase is elevated in the serum of individuals with acute myocardial infarction, but not in individuals with angina (Nomura, M. et al., *Br. Heart J*. 58:29-33, 1987; Herraez-Dominguez, M. V. et al., *Clin. Chim. Acta* 64:307-315, 1975). Further investigations into possible changes in plasma β-enolase concentration associated with unstable and stable angina need to be performed. The plasma concentration of β-enolase is elevated during heart surgery, muscular dystrophy, and skeletal muscle injury (Usui, A. et al., *Cardiovasc. Res*. 23:737-740, 1989; Kato, K. et al., Clin. Chim. Acta 131:75-85, 1983; Matsuda, H. et al., *Forensic Sci. Int*. 99:197-208, 1999). β-enolase is released into the bloodstream immediately following cardiac or skeletal muscle injury. The plasma β-enolase concentration was elevated to more than 150 ng/ml in the perioperative stage of cardiac surgery, and remained elevated for 1 week. Serum β-enolase concentrations peaked approximately 12-14 hours after the onset of chest pain and acute myocardial infarction and approached baseline after 1 week had elapsed from onset, with maximum levels approaching 1 μg/ml (Kato, K. et al., *Clin. Chim. Acta* 131:75-85, 1983; Nomura, M. et al., *Br. Heart J*. 58:29-33, 1987).

Creatine kinase (CK) is a 85 kDa cytosolic enzyme that catalyzes the reversible formation ADP and phosphocreatine from ATP and creatine. CK is a homo- or heterodimer composed of M and B chains. CK-MB is the isoform that is most specific for cardiac tissue, but it is also present in skeletal muscle and other tissues. The normal plasma concentration of CK-MB is <5 ng/ml. The plasma CK-MB concentration is significantly elevated in patients with acute myocardial infarction. Plasma CK-MB is not elevated in patients with stable angina, and investigation into plasma CK-MB concentration elevations in patients with unstable angina have yielded mixed results (Thygesen, K. et al., *Eur. J. Clin. Invest*. 16:1-4, 1986; Koukkunen, H. et al., *Ann. Med*. 30:488-496, 1998; Bertinchant, J. P. et al., *Clin. Biochem*. 29:587-594, 1996; Benamer, H. et al., *Am. J. Cardiol*. 82:845-850, 1998; Norregaard-Hansen, K. et al., *Eur. Heart J*. 13:188-193, 1992). The mixed results associated with unstable angina suggest that CK-MB may be useful in determining the severity of unstable angina because the extent of myocardial ischemia is directly proportional to unstable angina severity. Elevations of the plasma CK-MB concentration are associated with skeletal muscle injury and renal disease. CK-MB is released into the bloodstream following cardiac cell death. The plasma concentration of CK-MB in patients with acute myocardial infarction is significantly elevated 4-6 hours after onset, peaks between 12-24 hours, and returns to baseline after 3 days. The release kinetics of CK-MB associated with unstable angina may be similar.

Glycogen phosphorylase (GP) is a 188 kDa intracellular allosteric enzyme that catalyzes the removal of glucose (liberated as glucose-1-phosphate) from the nonreducing ends of glycogen in the presence of inorganic phosphate during glycogenolysis. GP is present as a homodimer, which associates with another homodimer to form a tetrameric enzymatically active phosphorylase A. There are three isoforms of GP that can be immunologically distinguished. The BB isoform is found in brain and cardiac tissue, the MM isoform is found in skeletal muscle and cardiac tissue, and the LL isoform is predominantly found in liver (Mair, J. et al., *Br. Heart J*. 72:125-127, 1994). GP-BB is normally associated with the sarcoplasmic reticulum glycogenolysis complex, and this association is dependent upon the metabolic state of the myocardium (Mair, J., *Clin. Chim. Acta* 272:79-86, 1998). At the onset of hypoxia, glycogen is broken down, and GP-BB is converted from a bound form to a free cytoplasmic form (Krause, E. G. et al., *Mol. Cell Biochem*. 160-161:289-295, 1996). The normal plasma GP-BB concentration is <7 ng/ml (36 pM). The plasma GP-BB concentration is significantly elevated in patients with acute myocardial infarction and unstable angina with transient ST-T elevations, but not stable angina (Mair, J. et al., *Br. Heart J*. 72:125-127, 1994; Mair, J., *Clin. Chim. Acta* 272:79-86, 1998; Rabitzsch, G. et al., *Clin. Chem*. 41:966-978, 1995; Rabitzsch, G. et al., *Lancet* 341: 1032-1033, 1993). Furthermore, GP-BB also can be used to detect perioperative acute myocardial infarction and myocardial ischemia in patients undergoing coronary artery bypass surgery (Rabitzsch, G. et al., *Biomed. Biochim. Acta* 46:S584-S588, 1987; Mair, P. et al., *Eur. J. Clin. Chem. Clin. Biochem*. 32:543-547, 1994). GP-BB has been demonstrated to be a more sensitive marker of unstable angina and acute myocardial infarction early after onset than CK-MB, cardiac tropopnin T, and myoglobin (Rabitzsch, G. et al., *Clin. Chem*. 41:966-978, 1995). Because it is also found in the brain, the plasma GP-BB concentration also may be elevated during ischemic cerebral injury. GP-BB is released into the bloodstream under ischemic conditions that also involve an increase in the permeability of the cell membrane, usually a result of cellular necrosis. GP-BB is significantly elevated within 4 hours of chest pain onset in individuals with unstable angina and transient ST-T ECG alterations, and is significantly elevated while myoglobin, CK-MB, and cardiac troponin T are still within normal levels (Mair, J. et al., *Br. Heart J.* 72:125-127, 1994). Furthermore, GP-BB can be significantly elevated 1-2 hours after chest pain onset in patients with acute myocardial infarction (Rabitzsch, G. et al., *Lancet* 341:1032-1033, 1993). The plasma GP-BB concentration in patients with unstable angina and acute myocardial infarction can exceed 50 ng/ml (250 pM) (Mair, J. et al., *Br. Heart J.* 72:125-127, 1994; Mair, J., *Clin. Chim. Acta* 272:79-86, 1998; Krause, E.G. et al., *Mol. Cell Biochem.* 160-161:289-295, 1996; Rabitzsch, G. et al., *Clin. Chem.* 41:966-978, 1995; Rabitzsch, G. et al., *Lancet* 341:1032-1033, 1993). GP-BB appears to be a very sensitive marker of myocardial ischemia, with specificity similar to that of CK-BB. GP-BB plasma concentrations are elevated within the first 4 hours after acute myocardial infarction onset, which suggests that it may be a very useful early marker of myocardial damage. Furthermore, GP-BB is not only a more specific marker of cardiac tissue damage, but also ischemia, since it is released to an unbound form during myocardial ischemia and would not normally be released upon traumatic injury. This is best illustrated by the usefulness of GP-BB in detecting myocardial ischemia during cardiac surgery. GP-BB may be a very useful marker of early myocardial ischemia during acute myocardial infarction and severe unstable angina.

Heart-type fatty acid binding protein (H-FABP) is a cytosolic 15 kDa lipid-binding protein involved in lipid metabolism. Heart-type FABP antigen is found not only in heart tissue, but also in kidney, skeletal muscle, aorta, adrenals, placenta, and brain (Veerkamp, J. H. and Maatman, R. G., *Prog. Lipid Res.* 34:17-52, 1995; Yoshimoto, K. et al., *Heart Vessels* 10:304-309, 1995). Furthermore, heart-type FABP mRNA can be found in testes, ovary, lung, mammary gland, and stomach (Veerkamp, J. H. and Maatman, R. G., *Prog. Lipid Res.* 34:17-52, 1995). The normal plasma concentration of FABP is <6 ng/ml (400 pM). The plasma H-FABP concentration is elevated in patients with acute myocardial infarction and unstable angina (Ishii, J. et al., *Clin. Chem.* 43:1372-1378, 1997; Tsuji, R. et al., *Int. J. Cardiol.* 41:209-217, 1993). Furthermore, H-FABP may be useful in estimating infarct size in patients with acute myocardial infarction (Glatz, J. F. et al., *Br. Heart J.* 71:135-140, 1994). Myocardial tissue as a source of H-FABP can be confirmed by determining the ratio of myoglobin/FABP (grams/grams). A ratio of approximately 5 indicates that FABP is of myocardial origin, while a higher ratio indicates skeletal muscle sources (Van Nieuwenhoven, F. A. et al., *Circulation* 92:2848-2854, 1995). Because of the presence of H-FABP in skeletal muscle, kidney and brain, elevations in the plasma H-FABP concentration may be associated with skeletal muscle injury, renal disease, or stroke. H-FABP is released into the bloodstream following cardiac tissue necrosis. The plasma H-FABP concentration can be significantly elevated 1-2 hours after the onset of chest pain, earlier than CK-MB and myoglobin (Tsuji, R. et al., *Int. J. Cardiol.* 41:209-217, 1993; Van Nieuwenhoven, F. A. et al., *Circulation* 92:2848-2854, 1995; Tanaka, T. et al., *Clin. Biochem.* 24:195-201, 1991). Additionally, H-FABP is rapidly cleared from the bloodstream, and plasma concentrations return to baseline after 24 hours after acute myocardial infarction onset (Glatz, J. F. et al., *Br. Heart J.* 71:135-140, 1994; Tanaka, T. et al. *Clin. Biochem.* 24:195-201, 1991).

Phosphoglyceric acid mutase (PGAM) is a 57 kDa homo- or heterodimeric intracellular glycolytic enzyme composed of 29 kDa M or B subunits that catalyzes the interconversion of 3-phosphoglycerate to 2-phosphoglycerate in the presence of magnesium. Cardiac tissue contains isozymes MM, MB, and BB, skeletal muscle contains primarily PGAM-MM, and most other tissues contain PGAM-BB (Durany, N. and Carreras, J., *Comp. Biochem. Physiol. B. Biochem. Mol. Biol.* 114:217-223, 1996). Thus, PGAM-MB is the most specific isozyme for cardiac tissue. PGAM is elevated in the plasma of patients with acute myocardial infarction, but further studies need to be performed to determine changes in the plasma PGAM concentration associated with acute myocardial infarction, unstable angina and stable angina (Mair, J., *Crit. Rev. Clin. Lab. Sci.* 34:1-66, 1997). Plasma PGAM-MB concentration elevations may be associated with unrelated myocardial or possibly skeletal tissue damage. PGAM-MB is most likely released into the circulation following cellular necrosis. PGAM has a half-life of less than 2 hours in the bloodstream of rats (Grisolia, S. et al., *Physiol. Chem. Phys.* 8:37-52, 1976).

S-100 is a 21 kDa homo- or heterodimeric cytosolic $Ca^{2+}$-binding protein produced from $\alpha$ and $\beta$ subunits. It is thought to participate in the activation of cellular processes along the $Ca^{2+}$-dependent signal transduction pathway (Bonfrer, J. M. et al., *Br. J. Cancer* 77:2210-2214, 1998). S-100ao ($\alpha\alpha$ isoform) is found in striated muscles, heart and kidney, S-100a ($\alpha\beta$ isoform) is found in glial cells, but not in Schwann cells, and S-100b ($\beta\beta$ isoform) is found in high concentrations in glial cells and Schwann cells, where it is a major cytosolic component (Kato, K. and Kimura, S., *Biochim. Biophys. Acta* 842:146-150, 1985; Hasegawa, S. et al., *Eur. Urol.* 24:393-396, 1993). The normal serum concentration of S-100ao is <0.25 ng/ml (12 pM), and its concentration may be influenced by age and sex, with higher concentrations in males and older individuals (Kikuchi, T. et al., *Hinyokika Kiyo* 36:1117-1123, 1990; Morita, T. et al., *Nippon Hinyokika Gakkai Zasshi* 81:1162-1167, 1990; Usui, A. et al., *Clin. Chem.* 36:639-641, 1990). The serum concentration of S-100ao is elevated in patients with acute myocardial infarction, but not in patients with angina pectoris with suspected acute myocardial infarction (Usui, A. et al., *Clin. Chem.* 36:639-641, 1990). Further investigation is needed to determine changes in the plasma concentration of S-100ao associated with unstable and stable angina. Serum S-100ao is elevated in the serum of patients with renal cell carcinoma, bladder tumor, renal failure, and prostate cancer, as well as in patients undergoing open heart surgery (Hasegawa, S. et al., *Eur. Urol.* 24:393-396, 1993; Kikuchi, T. et al., *Hinyokika Kiyo* 36:1117-1123, 1990; Morita, T. et al., *Nippon Hinyokika Gakkai Zasshi* 81:1162-1167, 1990; Usui, A. et al., *Clin. Chem.* 35:1942-1944, 1989). S-100ao is a cytosolic protein that will be released into the extracellular space following cell death. The serum concentration of S-100ao is significantly elevated on admission in patients with acute myocardial infarction, increases to peak levels 8 hours after admission, decreases and returns to baseline one week later (Usui, A. et al., *Clin. Chem.* 36:639-641, 1990). Furthermore, S-100ao appears to be significantly elevated earlier after acute myocardial infarction onset than CK-MB (Usui, A. et al., *Clin. Chem.* 36:639-641, 1990). The maximum serum S-100ao concentration can exceed 100 ng/ml. S-100ao may be rapidly cleared from the bloodstream by the kidney, as suggested by the rapid decrease of the serum S-100ao concentration of heart surgery patients following reperfusion and its increased urine concentration. S-100ao is found in high concentration in cardiac tissue and appears to be a sensitive marker of cardiac injury. Major sources of non-specificity of this marker include skeletal muscle and renal tissue injury. S-100ao may be significantly elevated soon after acute myocardial infarction onset, and it may allow for the discrimination of acute myocardial infarction from unstable angina. Patients with angina pectoris and suspected acute myocardial infarction, indicating that they were suffering chest pain associated with an ischemic episode, did not have a significantly elevated S-100ao concentration.

(ii) Exemplary Markers Related to Coagulation and Hemostasis

Plasmin is a 78 kDa serine proteinase that proteolytically digests crosslinked fibrin, resulting in clot dissolution. The 70 kDa serine proteinase inhibitor α2-antiplasmin (α2AP) regulates plasmin activity by forming a covalent 1:1 stoichiometric complex with plasmin. The resulting ~150 kDa plasmin-α2AP complex (PAP), also called plasmin inhibitory complex (PIC) is formed immediately after α2AP comes in contact with plasmin that is activated during fibrinolysis. The normal serum concentration of PAP is <1 µg/ml (6.9 nM). Elevations in the serum concentration of PAP can be attributed to the activation of fibrinolysis. Elevations in the serum concentration of PAP may be associated with clot presence, or any condition that causes or is a result of fibrinolysis activation. These conditions can include atherosclerosis, disseminated intravascular coagulation, acute myocardial infarction, surgery, trauma, unstable angina, stroke, and thrombotic thrombocytopenic purpura. PAP is formed immediately following proteolytic activation of plasmin. PAP is a specific marker for fibrinolysis activation and the presence of a recent or continual hypercoagulable state.

β-thromboglobulin (βTG) is a 36 kDa platelet α granule component that is released upon platelet activation. The normal plasma concentration of βTG is <40 ng/ml (1.1 nM). Plasma levels of β-TG appear to be elevated in patients with unstable angina and acute myocardial infarction, but not stable angina (De Caterina, R. et al., *Eur. Heart J.* 9:913-922, 1988; Bazzan, M. et al., *Cardiologia* 34, 217-220, 1989). Plasma β-TG elevations also seem to be correlated with episodes of ischemia in patients with unstable angina (Sobel, M. et al., *Circulation* 63:300-306, 1981). Elevations in the plasma concentration of βTG maybe associated with clot presence, or any condition that causes platelet activation. These conditions can include atherosclerosis, disseminated intravascular coagulation, surgery, trauma, and thrombotic thrombocytopenic purpura, and stroke (Landi, G. et al., *Neurology* 37:1667-1671, 1987). βTG is released into the circulation immediately after platelet activation and aggregation. It has a biphasic half-life of 10 minutes, followed by an extended 1 hour half-life in plasma (Switalska, H. I. et al., *J. Lab. Clin. Med.* 106:690-700, 1985). Plasma βTG concentration is reportedly elevated dring unstable angina and acute myocardial infarction. Special precautions must be taken to avoid platelet activation during the blood sampling process. Platelet activation is common during regular blood sampling, and could lead to artificial elevations of plasma βTG concentration. In addition, the amount of βTG released into the bloodstream is dependent on the platelet count of the individual, which can be quite variable. Plasma concentrations of βTG associated with ACS can approach 70 ng/ml (2 nM), but this value may be influenced by platelet activation during the sampling procedure.

Platelet factor 4 (PF4) is a 40 kDa platelet α granule component that is released upon platelet activation. PF4 is a marker of platelet activation and has the ability to bind and neutralize heparin. The normal plasma concentration of PF4 is <7 ng/ml (175 pM). The plasma concentration of PF4 appears to be elevated in patients with acute myocardial infarction and unstable angina, but not stable angina (Gallino, A. et al., *Am. Heart J.* 112:285-290, 1986; Sakata, K. et al., *Jpn. Circ. J.* 60:277-284, 1996; Bazzan, M. et al., *Cardiologia* 34:217-220, 1989). Plasma PF4 elevations also seem to be correlated with episodes of ischemia in patients with unstable angina (Sobel, M. et al., *Circulation* 63:300-306, 1981). Elevations in the plasma concentration of PF4 may be associated with clot presence, or any condition that causes platelet activation. These conditions can include atherosclerosis, disseminated intravascular coagulation, surgery, trauma, thrombotic thrombocytopenic purpura, and acute stroke (Carter, A. M. et al., *Arterioscler. Thromb. Vasc. Biol.* 18:1124-1131, 1998). PF4 is released into the circulation immediately after platelet activation and aggregation. It has a biphasic half-life of 1 minute, followed by an extended 20 minute half-life in plasma. The half-life of PF4 in plasma can be extended to 20-40 minutes by the presence of heparin (Rucinski, B. et al., *Am. J. Physiol.* 251:H800-H807, 1986). Plasma PF4 concentration is reportedly elevated during unstable angina and acute myocardial infarction, but these studies may not be completely reliable. Special precautions must be taken to avoid platelet activation during the blood sampling process. Platelet activation is common during regular blood sampling, and could lead to artificial elevations of plasma PF4 concentration. In addition, the amount of PF4 released into the bloodstream is dependent on the platelet count of the individual, which can be quite variable. Plasma concentrations of PF4 associated with disease can exceed 100 ng/ml (2.5 nM), but it is likely that this value may be influenced by platelet activation during the sampling procedure.

Fibrinopeptide A (FPA) is a 16 amino acid, 1.5 kDa peptide that is liberated from amino terminus of fibrinogen by the action of thrombin. Fibrinogen is synthesized and secreted by the liver. The normal-plasma concentration of FPA is <5 ng/ml (3.3 nM). The plasma FPA concentration is elevated in patients with acute myocardial infarction, unstable angina, and variant angina, but not stable angina (Gensini, G. F. et al., *Thromb. Res.* 50:517-525, 1988; Gallino, A. et al., *Am. Heart J.* 112:285-290, 1986; Sakata, K. et al., *Jpn. Circ. J.* 60:277-284, 1996; Theroux, P. et al., *Circulation* 75:156-162, 1987; Merlini, P. A. et al., *Circulation* 90:61-68, 1994; Manten, A. et al., *Cardiovasc. Res.* 40:389-395, 1998). Furthermore, plasma FPA may indicate the severity of angina (Gensini, G. F. et al., *Thromb. Res.* 50:517-525, 1988). Elevations in the plasma concentration of FPA are associated with any condition that involves activation of the coagulation pathway, including stroke, surgery, cancer, disseminated intravascular coagulation, nephrosis, and thrombotic thrombocytopenic purpura. FPA is released into the circulation following thrombin activation and cleavage of fibrinogen. Because FPA is a small polypeptide, it is likely cleared from the bloodstream rapidly. FPA has been demonstrated to be elevated for more than one month following clot formation, and maximum plasma FPA concentrations can exceed 40 ng/ml in active angina (Gensini, G. F. et al., *Thromb. Res.* 50:517-525, 1988; Tohgi, H. et al., *Stroke* 21:1663-1667, 1990).

Platelet-derived growth factor (PDGF) is a 28 kDa secreted homo- or heterodimeric protein composed of the homologous subunits A and/or B (Mahadevan, D. et al., *J. Biol. Chem.* 270:27595-27600, 1995). PDGF is a potent mitogen for mesenchymal cells, and has been implicated in the pathogenesis of atherosclerosis. PDGF is released by aggregating platelets and monocytes near sites of vascular injury. The normal plasma concentration of PDGF is <0.4 ng/ml (15 pM). Plasma PDGF concentrations are higher in individuals with acute myocardial infarction and unstable angina than in healthy controls or individuals with stable angina (Ogawa, H. et al., *Am. J. Cardiol.* 69:453-456, 1992; Wallace, J. M. et al., *Ann. Clin. Biochem.* 35:236-241, 1998; Ogawa, H. et al., *Coron. Artery Dis.* 4:437-442, 1993). Changes in the plasma PDGF concentration in these individuals is most likely due to increased platelet and monocyte activation. Plasma PDGF is elevated in individuals with brain tumors, breast cancer, and hypertension (Kurimoto, M. et al., *Acta Neurochir.* (Wien) 137:182-187, 1995; Seymour, L. et al., *Breast Cancer Res. Treat.* 26:247-252, 1993; Rossi, E. et al., *Am. J. Hypertens.* 11:1239-1243, 1998). Plasma PDGF may also be elevated in any pro-inflammatory condition or any condition that causes platelet activation including surgery, trauma, disseminated intravascular coagulation, and thrombotic thrombocytopenic purpura. PDGF is released from the secretory granules of platelets and monocytes upon activation. PDGF has a biphasic half-life of approximately 5 minutes and 1 hour in animals (Cohen, A. M. et al., *J. Surg. Res.* 49:447-452, 1990; Bowen-Pope, D. F. et al., *Blood* 64:458-469, 1984). The plasma PDGF concentration in ACS can exceed 0.6 ng/ml (22 pM) (Ogawa, H. et al., *Am. J. Cardiol.* 69:453-456, 1992). PDGF may be a sensitive and specific marker of platelet activation. In addition, it may be a sensitive marker of vascular injury, and the accompanying monocyte and platelet activation.

Prothrombin fragment 1+2 is a 32 kDa polypeptide that is liberated from the amino terminus of thrombin during thrombin activation. The normal plasma concentration of F1+2 is <32 ng/ml (1 nM). The plasma concentration of F1+2 is reportedly elevated in patients with acute myocardial infarction and unstable angina, but not stable angina, but the changes were not robust (Merlini, P. A. et al., *Circulation* 90:61-68, 1994). Other reports have indicated that there is no significant change in the plasma F1+2 concentration in cardiovascular disease (Biasucci, L. M. et al., *Circulation* 93:2121-2127, 1996; Manten, A. et al., *Cardiovasc. Res.* 40:389-395, 1998). The concentration of F1+2 in plasma can be elevated during any condition associated with coagulation activation, including stroke, surgery, trauma, thrombotic thrombocytopenic purpura, and disseminated intravascular coagulation. F1+2 is released into the bloodstream immediately upon thrombin activation. F1+2 has a half-life of approximately 90 minutes in plasma, and it has been suggested that this long half-life may mask bursts of thrombin formation (Biasucci, L. M. et al., *Circulation* 93:2121-2127, 1996).

P-selectin, also called granule membrane protein-140, GMP-140, PADGEM, and CD-62P, is a ~140 kDa adhesion molecule expressed in platelets and endothelial cells. P-selectin is stored in the alpha granules of platelets and in the Weibel-Palade bodies of endothelial cells. Upon activation, P-selectin is rapidly translocated to the surface of endothelial cells and platelets to facilitate the "rolling" cell surface interaction with neutrophils and monocytes. Membrane-bound and soluble forms of P-selectin have been identified. Soluble P-selectin may be produced by shedding of membrane-bound P-selectin, either by proteolysis of the extracellular P-selectin molecule, or by proteolysis of components of the intracellular cytoskeleton in close proximity to the surface-bound P-selectin molecule (Fox, J. E., *Blood Coagul. Fibrinolysis* 5:291-304, 1994). Additionally, soluble P-selectin may be translated from mRNA that does not encode the N-terminal transmembrane domain (Dunlop, L. C. et al., *J. Exp. Med.* 175:1147-1150, 1992; Johnston, G. I. et al., *J. Biol. Chem.* 265:21381-21385, 1990). Activated platelets can shed membrane-bound P-selectin and remain in the circulation, and the shedding of P-selectin can elevate the plasma P-selectin concentration by approximately 70 ng/ml (Michelson, A. D. et al., *Proc. Natl. Acad. Sci. U.S.A.* 93:11877-11882, 1996). Soluble P-selectin may also adopt a different conformation than membrane-bound P-selectin. Soluble P-selectin has a monomeric rod-like structure with a globular domain at one end, and the membrane-bound molecule forms rosette structures with the globular domain facing outward (Ushiyama, S. et al., *J. Biol. Chem.* 268:15229-15237, 1993). Soluble P-selectin may play an important role in regulating inflammation and thrombosis by blocking interactions between leukocytes and activated platelets and endothelial cells (Gamble, J. R. et al., *Science* 249:414-417, 1990). The normal plasma concentration of soluble P-selectin is <200 ng/ml. Blood is normally collected using citrate as an anticoagulant, but some studies have used EDTA plasma with additives such as prostaglandin E to prevent platelet activation. EDTA may be a suitable anticoagulant that will yield results comparable to those obtained using citrate. Furthermore, the plasma concentration of soluble P-selectin may not be affected by potential platelet activation during the sampling procedure. The plasma soluble P-selectin concentration was significantly elevated in patients with acute myocardial infarction and unstable angina, but not stable angina, even following an exercise stress test (Ikeda, H. et al., *Circulation* 92:1693-1696, 1995; Tomoda, H. and Aoki, N., *Angiology* 49:807-813, 1998; Hollander, J. E. et al., *J. Am. Coll. Cardiol.* 34:95-105, 1999; Kaikita, K. et al., *Circulation* 92:1726-1730, 1995; Ikeda, H. et al., *Coron. Artery Dis.* 5:515-518, 1994). The sensitivity and specificity of membrane-bound P-selectin versus soluble P-selectin for acute myocardial infarction is 71% versus 76% and 32% versus 45% (Hollander, J. E. et al., *J. Am. Coll. Cardiol.* 34:95-105, 1999). The sensitivity and specificity of membrane-bound P-selectin versus soluble P-selectin for unstable angina+ acute myocardial infarction is 71% versus 79% and 30% versus 35% (Hollander, J. E. et al., *J. Am. Coll. Cardiol.* 34:95-105, 1999). P-selectin expression is greater in coronary atherectomy specimens from individuals with unstable angina than stable angina (Tenaglia, A. N. et al., *Am. J. Cardiol.* 79:742-747, 1997). Furthermore, plasma soluble P-selectin may be elevated to a greater degree in patients with acute myocardial infarction than in patients with unstable angina. Plasma soluble and membrane-bound P-selectin also is elevated in individuals with non-insulin dependent diabetes mellitus and congestive heart failure (Nomura, S. et al., *Thromb. Haemost.* 80:388-392, 1998; O'Connor, C. M. et al., *Am. J. Cardiol.* 83:1345-1349, 1999). Soluble P-selectin concentration is elevated in the plasma of individuals with idiopathic thrombocytopenic purpura, rheumatoid arthritis, hypercholesterolemia, acute stroke, atherosclerosis, hypertension, acute lung injury, connective tissue disease, thrombotic thrombocytopenic purpura, hemolytic uremic syndrome, disseminated intravascular coagulation, and chronic renal failure (Katayama, M. et al., *Br. J. Haematol.* 84:702-710, 1993; Haznedaroglu, I. C. et al., *Acta Haematol.* 101:16-20, 1999; Ertenli, I. et al., *J. Rheumatol.* 25:1054-1058, 1998; Davi, G. et al., *Circulation* 97:953-957, 1998; Frijns, C. J. et al, *Stroke* 28:2214-2218, 1997; Blann, A. D. et al., *Thromb. Haemost.* 77:1077-1080, 1997; Blann, A. D. et al., *J. Hum. Hypertens.* 11:607-609, 1997; Sakamaki, F. et al., *A. J. Respir. Crit. Care Med.* 151:1821-1826, 1995; Takeda, I. et al., *Int. Arch. Allergy Immunol.* 105:128-134, 1994; Chong, B. H. et al., *Blood* 83:1535-1541, 1994; Bonomini, M. et al., *Nephron* 79:399-407, 1998). Additionally, any condition that involves platelet activation can potentially be a source of plasma elevations in P-selectin. P-selectin is rapidly presented on the cell surface following platelet of endothelial cell activation. Soluble P-selectin that has been translated from an alternative mRNA lacking a transmembrane domain is also released into the extracellular space following this activation. Soluble P-selectin can also be formed by proteolysis involving membrane-bound P-selectin, either directly or indirectly. Plasma soluble P-selectin is elevated on admission in patients with acute myocardial infarction treated with tPA or coronary angioplasty, with a peak elevation occurring 4 hours after onset (Shimomura, H. et al., *Am. J. Cardiol.* 81:397-400, 1998). Plasma soluble P-selectin was elevated less than one hour following an anginal attack in patients with unstable angina, and the concentration decreased with time, approaching baseline more than 5 hours after attack onset (Ikeda, H. et al., *Circulation* 92:1693-1696, 1995). The plasma concentration of soluble P-selectin can approach 1 µg/ml in ACS (Ikeda, H. et al., *Coron. Artery Dis.* 5:515-518, 1994). Further investigation into the release of soluble P-selectin into and its removal from the bloodstream need to be conducted. P-selectin may be a sensitive and specific marker of platelet and endothelial cell activation, conditions that support thrombus formation and inflammation. It is not, however, a specific marker of ACS. When used with another marker that is specific for cardiac tissue injury, P-selectin may be useful in the discrimination of unstable angina and acute myocardial infarction from stable angina. Furthermore, soluble P-selectin may be elevated to a greater degree in acute myocardial infarction than in unstable angina. P-selectin normally exists in two forms, membrane-bound and soluble. Published investigations note that a soluble form of P-selectin is produced by platelets and endothelial cells, and by shedding of membrane-bound P-selectin, potentially through a proteolytic mechanism. Soluble P-selectin may prove to be the most useful currently identified marker of platelet activation, since its plasma concentration may not be as influenced by the blood sampling procedure as other markers of platelet activation, such as PF4 and β-TG.

Thrombin is a 37 kDa serine proteinase that proteolytically cleaves fibrinogen to form fibrin, which is ultimately integrated into a crosslinked network during clot formation. Antithrombin III (ATIII) is a 65 kDa serine proteinase inhibitor that is a physiological regulator of thrombin, factor XIa, factor XIIa, and factor IXa proteolytic activity. The inhibitory activity of ATIII is dependent upon the binding of heparin. Heparin enhances the inhibitory activity of ATIII by 2-3 orders of magnitude, resulting in almost instantaneous inactivation of proteinases inhibited by ATIII. ATIII inhibits its target proteinases through the formation of a covalent 1:1 stoichiometric complex. The normal plasma concentration of the approximately 100 kDa thrombin-ATIII complex (TAT) is <5 ng/ml (50 pM). TAT concentration is elevated in patients with acute myocardial infarction and unstable angina, especially during spontaneous ischemic episodes (Biasucci, L. M. et al., *Am. J. Cardiol.* 77:85-87, 1996; Kienast, J. et al., *Thromb. Haemost.* 70:550-553, 1993). Furthermore, TAT may be elevated in the plasma of individuals with stable angina (Manten, A. et al, *Cardiovasc. Res.* 40:389-395, 1998). Other published reports have found no significant differences in the concentration of TAT in the plasma of patients with ACS (Manten, A. et al., *Cardiovasc. Res.* 40:389-395, 1998; Hoffmeister, H. M. et al., *Atherosclerosis* 144:151-157, 1999). Further investigation is needed to determine plasma TAT concentration changes associated with ACS. Elevation of the plasma TAT concentration is associated with any condition associated with coagulation activation, including stroke, surgery, trauma, disseminated intravascular coagulation, and thrombotic thrombocytopenic purpura. TAT is formed immediately following thrombin activation in the presence of heparin, which is the limiting factor in this interaction. TAT has a half-life of approximately 5 minutes in the bloodstream (Biasucci, L. M. et al., *Am. J. Cardiol.* 77:85-87, 1996). TAT concentration is elevated in, exhibits a sharp drop after 15 minutes, and returns to baseline less than 1 hour following coagulation activation. The plasma concentration of TAT can approach 50 ng/ml in ACS (Biasucci, L. M. et al., *Circulation* 93:2121-2127, 1996). TAT is a specific marker of coagulation activation, specifically, thrombin activation.

von Willebrand factor (vWF) is a plasma protein produced by platelets, megakaryocytes, and endothelial cells composed of 220 kDa monomers that associate to form a series of high molecular weight multimers. These multimers normally range in molecular weight from 600-20,000 kDa. vWF participates in the coagulation process by stabilizing circulating coagulation factor VIII and by mediating platelet adhesion to exposed subendothelium, as well as to other platelets. The A1 domain of vWF binds to the platelet glycoprotein Ib-IX-V complex and non-fibrillar collagen type VI, and the A3 domain binds fibrillar collagen types I and III (Emsley, J. et al., *J. Biol. Chem.* 273:10396-10401, 1998). Other domains present in the vWF molecule include the integrin binding domain, which mediates platelet-platelet interactions, the the protease cleavage domain, which appears to be relevant to the pathogenesis of type 11A von Willebrand disease. The interaction of vWF with platelets is tightly regulated to avoid interactions between vWF and platelets in normal physiologic conditions. vWF normally exists in a globular state, and it undergoes a conformation transition to an extended chain structure under conditions of high sheer stress, commonly found at sites of vascular injury. This conformational change exposes intramolecular domains of the molecule and allows vWF to interact with platelets. Furthermore, shear stress may cause vWF release from endothelial cells, making a larger number of vWF molecules available for interactions with platelets. The conformational change in vWF can be induced in vitro by the addition of non-physiological modulators like ristocetin and botrocetin (Miyata, S. et al., *J. Biol. Chem.* 271:9046-9053, 1996). At sites of vascular injury, vWF rapidly associates with collagen in the subendothelial matrix, and virtually irreversibly binds platelets, effectively forming a bridge between platelets and the vascular subendothelium at the site of injury. Evidence also suggests that a conformational change in vWF may not be required for its interaction with the subendothelial matrix (Sixma, J. J. and de Groot, P. G., *Mayo Clin. Proc.* 66:628-633, 1991). This suggests that vWF may bind to the exposed subendothelial matrix at sites of vascular injury, undergo a conformational change because of the high localized shear stress, and rapidly bind circulating platelets, which will be integrated into the newly formed thrombus. Measurement of the total amount of vWF would allow one who is skilled in the art to identify changes in total vWF concentration associated with stroke or cardiovascular disease. This measurement could be performed through the measurement of various forms of the vWF molecule. Measurement of the A1 domain would allow the measurement of active vWF in the circulation, indicating that a pro-coagulant state exists because the A1 domain is accessible for platelet binding. In this regard, an assay that specifically measures vWF molecules with both the exposed A1 domain and either the integrin binding domain or the A3 domain would also allow for the identification of active vWF that would be available for mediating platelet-platelet interactions or mediate crosslinking of platelets to vascular subendothelium, respectively. Measurement of any of these vWF forms, when used in an assay that employs antibodies specific for the protease cleavage domain may allow assays to be used to determine the circulating concentration of various vWF forms in any individual, regardless of the presence of von Willebrand disease. The normal plasma concentration of vWF is 5-10 µg/ml, or 60-110% activity, as measured by platelet aggregation. The measurement of specific forms of vWF may be of importance in any type of vascular disease, including stroke and cardiovascular disease. The plasma vWF concentration is reportedly elevated in individuals with acute myocardial infarction and unstable angina, but not stable angina (Goto, S. et al., *Circulation* 99:608-613, 1999; Tousoulis, D. et al., *Int. J. Cardiol*. 56:259-262, 1996; Yazdani, S. et al., *J Am Coll Cardiol* 30:1284-1287, 1997; Montalescot, G. et al., *Circulation* 98:294-299). Furthermore, elevations of the plasma vWF concentration may be a predictor of adverse clinical outcome in patients with unstable angina (Montalescot, G. et al., *Circulation* 98:294-299). vWF concentrations also have been demonstrated to be elevated in patients with stroke and subarachnoid hemorrhage, and also appear to be useful in assessing risk of mortality following stroke (Blann, A. et al., *Blood Coagul. Fibrinolysis* 10:277-284, 1999; Hirashima, Y. et al.. *Neurochem Res*. 22:1249-1255, 1997; Catto, A. J. et al., *Thromb. Hemost*. 77:1104-1108, 1997). The plasma concentration of vWF may be elevated in conjunction with any event that is associated with endothelial cell damage or platelet activation. vWF is present at high concentration in the bloodstream, and it is released from platelets and endothelial cells upon activation. vWF would likely have the greatest utility as a marker of platelet activation or, specifically, conditions that favor platelet activation and adhesion to sites of vascular injury. The conformation of VWF is also known to be altered by high shear stress, as would be associated with a partially stenosed blood vessel. As the blood flows past a stenosed vessel, it is subjected to shear stress considerably higher than is encountered in the circulation of an undiseased individual.

Tissue factor (TF) is a 45 kDa cell surface protein expressed in brain, kidney, and heart, and in a transcriptionally regulated manner on perivascular cells and monocytes. TF forms a complex with factor VIIa in the presence of $Ca^{2+}$ ions, and it is physiologically active when it is membrane bound. This complex proteolytically cleaves factor X to form factor Xa. It is normally sequestered from the bloodstream. Tissue factor can be detected in the bloodstream in a soluble form, bound to factor VIIa, or in a complex with factor VIIa, and tissue factor pathway inhibitor that can also include factor Xa. TF also is expressed on the surface of macrophages, which are commonly found in atherosclerotic plaques. The normal serum concentration of TF is <0.2 ng/ml (4.5 pM). The plasma TF concentration is elevated in patients with ischemic heart disease (Falciani, M. et al., *Thromb. Hemost*. 79:495-499, 1998). TF is elevated in patients with unstable angina and acute myocardial infarction, but not in patients with stable angina (Falciani, M. et al., *Thromb. Hemost*. 79:495-499, 1998; Suefuji, H. et al., *Am. Heart J*. 134:253-259, 1997; Misumi, K. et al., *Am. J. Cardiol*. 81:22-26, 1998). Furthermore, TF expression on macrophages and TF activity in atherosclerotic plaques is more common in unstable angina than stable angina (Soejima, H. et al., *Circulation* 99:2908-2913, 1999; Kaikita, K. et al., *Arterioscler. Thromb. Vasc. Biol*. 17:2232-2237, 1997; Ardissino, D. et al., *Lancet* 349:769-771, 1997). The differences in plasma TF concentration in stable versus unstable angina may not be of statistical significance. Elevations in the serum concentration of TF are associated with any condition that causes or is a result of coagulation activation through the extrinsic pathway. These conditions can include subarachnoid hemorrhage, disseminated intravascular coagulation, renal failure, vasculitis, and sickle cell disease (Hirashima, Y. et al., *Stroke* 28:1666-1670, 1997; Takahashi, H. et al., *Am. J. Hematol*. 46:333-337, 1994; Koyama, T. et al., *Br. J. Haematol*. 87:343-347, 1994). TF is released immediately when vascular injury is coupled with extravascular cell injury. TF levels in ischemic heart disease patients can exceed 800 pg/ml within 2 days of onset (Falciani, M. et al., *Thromb. Hemost*. 79:495-499, 1998. TF levels were decreased in the chronic phase of acute myocardial infarction, as compared with the chronic phase (Suefuji, H. et al., *Am. Heart J*. 134:253-259, 1997). TF is a specific marker for activation of the extrinsic coagulation pathway and the presence of a general hypercoagulable state. It may be a sensitive marker of vascular injury resulting from plaque rupture The coagulation cascade can be activated through either the extrinsic or intrinsic pathways. These enzymatic pathways share one final common pathway. The first step of the common pathway involves the proteolytic cleavage of prothrombin by the factor Xa/factor Va prothrombinase complex to yield active thrombin. Thrombin is a serine proteinase that proteolytically cleaves fibrinogen. Thrombin first removes fibrinopeptide A from fibrinogen, yielding desAA fibrin monomer, which can form complexes with all other fibrinogen-derived proteins, including fibrin degradation products, fibrinogen degradation products, desAA fibrin, and fibrinogen. The desAA fibrin monomer is generically referred to as soluble fibrin, as it is the first product of fibrinogen cleavage, but it is not yet crosslinked via factor XIIIa into an insoluble fibrin clot. DesAA fibrin monomer also can undergo further proteolytic cleavage by thrombin to remove fibrinopeptide B, yielding desAABB fibrin monomer. This monomer can polymerize with other desAABB fibrin monomers to form soluble desAABB fibrin polymer, also referred to as soluble fibrin or thrombus precursor protein (TpP™). TpP™ is the immediate precursor to insoluble fibrin, which forms a "mesh-like" structure to provide structural rigidity to the newly formed thrombus. In this regard, measurement of TpP™ in plasma is a direct measurement of active clot formation. The normal plasma concentration of TpP™ is <6 ng/ml (Laurino, J. P. et al., *Ann. Clin. Lab. Sci*. 27:338-345, 1997). American Biogenetic Sciences has developed an assay for TpP™ (U.S. Pat. Nos. 5,453,359 and 5,843,690) and states that its TpP™ assay can assist in the early diagnosis of acute myocardial infarction, the ruling out of acute myocardial infarction in chest pain patients, and the identification of patients with unstable angina that will progress to acute myocardial infarction. Other studies have confirmed that TpP™ is elevated in patients with acute myocardial infarction, most often within 6 hours of onset (Laurino, J. P. et al., *Ann. Clin. Lab. Sci*. 27:338-345, 1997; Carville, D. G. et al., *Clin. Chem*. 42:1537-1541, 1996). The plasma concentration of TpP™ is also elevated in patients with unstable angina, but these elevations may be indicative of the severity of angina and the eventual progression to acute myocardial infarction (Laurino, J. P. et al., *Ann. Clin. Lab. Sci*. 27:338-345, 1997). The concentration of TpP™ in plasma will theoretically be elevated during any condition that causes or is a result of coagulation activation, including disseminated intravascular coagulation, deep venous thrombosis, congestive heart failure, surgery, cancer, gastroenteritis, and cocaine overdose (Laurino, J. P. et al., *Ann. Clin. Lab. Sci*. 27:338-345, 1997). TpP™ is released into the bloodstream immediately following thrombin activation. TpP™ likely has a short half-life in the bloodstream because it will be rapidly converted to insoluble fibrin at the site of clot formation. Plasma TpP™ concentrations peak within 3 hours of acute myocardial infarction onset, returning to normal after 12 hours from onset. The plasma concentration of TpP™ can exceed 30 ng/ml in CVD (Laurino, J. P. et al., *Ann. Clin. Lab. Sci*. 27:338-345, 1997). TpP™ is a sensitive and specific marker of coagulation activation. It has been demonstrated that TpP™ is useful in the diagnosis of acute myocardial infarction, but only when it is used in conjunction with a specific marker of cardiac tissue injury.

(iii) Exemplary Markers Related to Atherosclerotic Plaque Rupture

The appearance of markers related to atherosclerotic plaque rupture may preceed specific markers of myocardial injury. Potential markers of atherosclerotic plaque rupture include human neutrophil elastase, inducible nitric oxide synthase, lysophosphatidic acid, malondialdehyde-modified low density lipoprotein, and various members of the matrix metalloproteinase (MMP) family, including MMP-1, -2, -3, and -9.

Human neutrophil elastase (HNE) is a 30 kDa serine proteinase that is normally contained within the azurophilic granules of neutrophils. HNE is released upon neutrophil activation, and its activity is regulated by circulating $\alpha_1$-proteinase inhibitor. Activated neutrophils are commonly found in atherosclerotic plaques, and rupture of these plaques may result in the release of HNE. The plasma HNE concentration is usually measured by detecting HNE-$\alpha_1$-PI complexes. The normal concentration of these complexes is 50 ng/ml, which indicates a normal concentration of approximately 25 ng/ml (0.8 nM) for HNE. HNE release also can be measured through the specific detection of fibrinopeptide $B\beta_{30-43}$, a specific HNE-derived fibrinopeptide, in plasma. Plasma HNE is elevated in patients with coronary stenosis, and its elevation is greater in patients with complex plaques than those with simple plaques (Kosar, F. et al., *Angiology* 49:193-201, 1998; Amaro, A. et al., *Eur. Heart J.* 16:615-622, 1995). Plasma HNE is not significantly elevated in patients with stable angina, but is elevated inpatients with unstable angina and acute myocardial infarction, as determined by measuring fibrinopeptide $B\beta_{30-43}$, with concentrations in unstable angina being 2.5-fold higher than those associated with acute myocardial infarction (Dinerman, J. L. et al., *J. Am. Coll. Cardiol.* 15:1559-1563, 1990; Mehta, J. et al., *Circulation* 79:549-556, 1989). Serum HNE is elevated in cardiac surgery, exercise-induced muscle damage, giant cell arteritis, acute respiratory distress syndrome, appendicitis, pancreatitis, sepsis, smoking-associated emphysema, and cystic fibrosis (Genereau, T. et al., *J. Rheumatol.* 25:710-713, 1998; Mooser, V. et al., *Arterioscler. Thromb. Vase. Biol.* 19:1060-1065, 1999; Gleeson, M. et al.. *Eur. J. Appl. Physiol*. 77:543-546, 1998; Gando, S. et al., *J Trauma* 42:1068-1072, 1997; Eriksson, S. et al., *Eur. J. Surg.* 161:901-905, 1995; Liras, G. et al., *Rev. Esp. Enferm. Dig.* 87:641-652, 1995; Endo, S. et al., *J. Inflamm.* 45:136-142, 1995; Janoff, A., *Annu Rev Med* 36:207-216, 1985). HNE may also be released during blood coagulation (Plow, E. F. and Plescia, J., *Thromb. Hemost.* 59:360-363, 1988; Plow, E. F., *J. Clin. Invest.* 69:564-572, 1982). Serum elevations of HNE could also be associated with any non-specific infection or inflammatory state that involves neutrophil recruitment and activation. It is most likely released upon plaque rupture, since activated neutrophils are present in atherosclerotic plaques. HNE is presumably cleared by the liver after it has formed a complex with $\alpha_1$-PI.

Inducible nitric oxide synthase (iNOS) is a 130 kDa cytosolic protein in epithelial cells macrophages whose expression is regulated by cytokines, including interferon-γ, interleukin-1β, interleukin-6, and tumor necrosis factor a, and lipopolysaccharide. iNOS catalyzes the synthesis of nitric oxide (NO) from L-arginine, and its induction results in a sustained high-output production of NO, which has antimicrobial activity and is a mediator of a variety of physiological and inflammatory events. NO production by iNOS is approximately 100 fold more than the amount produced by constitutively-expressed NOS (Depre, C. et al., *Cardiovasc. Res.* 41:465-472, 1999). There are no published investigations of plasma iNOS concentration changes associated with ACS. iNOS is expressed in coronary atherosclerotic plaque, and it may interfere with plaque stability through the production of peroxynitrate, which is a product of NO and superoxide and enhances platelet adhesion and aggregation (Depre, C. et al., *Cardiovasc. Res*. 41:465-472, 1999). iNOS expression during myocardial ischemia may not be elevated, suggesting that iNOS may be useful in the differentiation of angina from acute myocardial infarction (Hammerman, S. I. et al., *Am. J. Physiol*. 277:H1579-H1592, 1999; Kaye, D. M. et al., *Life Sci* 62:883-887, 1998). Elevations in the plasma iNOS concentration may be associated with cirrhosis, iron-deficiency anemia, or any other condition that results in macrophage activation, including bacterial infection (Jimenez, W. et al., *Hepatology* 30:670-676, 1999; Ni, Z. et al., *Kidney Int*. 52:195-201, 1997). iNOS maybe released into the bloodstream as a result of atherosclerotic plaque rupture, and the presence of increased amounts of iNOS in the bloodstream may not only indicate that plaque rupture has occurred, but also that an ideal environment has been created to promote platelet adhesion. However, iNOS is not specific for atherosclerotic plaque rupture, and its expression can be induced during non-specific inflammatory conditions.

Lysophosphatidic acid (LPA) is a lysophospholipid intermediate formed in the synthesis of phosphoglycerides and triacylglycerols. It is formed by the acylation of glycerol-3 phosphate by acyl-coenzyme A and during mild oxidation of low-density lipoprotein (LDL). LPA is a lipid second messanger with vasoactive properties, and it can function as a platelet activator. LPA is a component of atherosclerotic lesions, particularly in the core, which is most prone to rupture (Siess, W., *Proc. Natl. Acad. Sci. U.S.A*. 96, 6931-6936, 1999). The normal plasma LPA concentration is 540 nM. Serum LPA is elevated in renal failure and in ovarian cancer and other gynecologic cancers (Sasagawa, T. et al., *J. Nutr. Sci. Vitaminol*. (Tokyo) 44:809-818, 1998; Xu, Y. et al., *JAMA* 280:719-723, 1998). In the context of unstable angina, LPA is most likely released as a direct result of plaque rupture. The plasma LPA concentration can exceed 60 μM in patients with gynecologic cancers (Xu, Y. et al., *JAMA* 280:719-723, 1998). Serum LPA may be a useful marker of atherosclerotic plaque rupture.

Malondialdehyde-modified low-density lipoprotein (MDA-modified LDL) is formed during the oxidation of the apoB-100 moiety of LDL as a result of phospholipase activity, prostaglandin synthesis, or platelet activation. MDA-modified LDL can be distinguished from oxidized LDL because MDA modifications of LDL occur in the absence of lipid peroxidation (Holvoet, P., *Acta Cardiol*. 53:253-260, 1998). The normal plasma concentration of MDA-modified LDL is less than 4 μg/ml (~10 μM). Plasma concentrations of oxidized LDL are elevated in stable angina, unstable angina, and acute myocardial infarction, indicating that it may be a marker of atherosclerosis (Holvoet, P., *Acta Cardiol*. 53:253-260, 1998; Holvoet, P. et al., *Circulation* 98:1487-1494, 1998). Plasma MDA-modified LDL is not elevated in stable angina, but is significantly elevated in unstable angina and acute myocardial infarction (Holvoet, P., *Acta Cardiol*. 53:253-260, 1998; Holvoet, P. et al., *Circulation* 98:1487-1494, 1998; Holvoet, P. et al., *JAMA* 281:1718-1721, 1999). Plasma MDA-modified LDL is elevated in individuals with beta-thallasemia and in renal transplant patients (Livrea, M. A. et al., *Blood* 92:3936-3942, 1998; Ghanem, H. et al., *Kidney Int*. 49:488-493, 1996; van den Dorpel, M. A. et al., *Transpl. Int. 9 Suppl*. 1:S54-S57, 1996). Furthermore, serum MDA-modified LDL may be elevated during hypoxia (Balagopalakrishna, C. et al., *Adv. Exp. Med. Biol*. 411:337-345, 1997). The plasma concentration of MDA-modified LDL is elevated within 6-8 hours from the onset of chest pain. Plasma concentrations of MDA-modified LDL can approach 20 μg/ml (~50 μM) in patients with acute myocardial infarction, and 15 μg/ml (~40 μM) in patients with unstable angina (Holvoet, P. et al., *Circulation* 98:1487-1494, 1998). Plasma MDA-modified LDL has a half-life of less than 5 minutes in mice (Ling, W. et al, *J. Clin. Invest.* 100:244-252, 1997). MDA-modified LDL appears to be a specific marker of atherosclerotic plaque rupture in acute coronary symptoms. It is unclear, however, if elevations in the plasma concentration of MDA-modified LDL are a result of plaque rupture or platelet activation. The most reasonable explanation is that the presence of increased amounts of MDA-modified LDL is an indication of both events. MDA-modified LDL may be useful in discriminating unstable angina and acute myocardial infarction from stable angina.

Matrix metalloproteinase-1 (MMP-1), also called collagenase-1, is a 41/44 kDa zinc- and calcium-binding proteinase that cleaves primarily type I collagen, but can also cleave collagen types II, III, VII and X. The active 41/44 kDa enzyme can undergo autolysis to the still active 22/27 kDa form. MMP-1 is synthesized by a variety of cells, including smooth muscle cells, mast cells, macrophage-derived foam cells, T lymphocytes, and endothelial cells (Johnson, J. L. et al., *Arterioscler. Thromb. Vasc. Biol.* 18:1707-1715, 1998). MMP-1, like other MMPs, is involved in extracellular matrix remodeling, which can occur following injury or during intervascular cell migration. MMP-1 can be found in the bloodstream either in a free form or in complex with TIMP-1, its natural inhibitor. MMP-1 is normally found at a concentration of <25 ng/ml in plasma. MMP-1 is found in the shoulder region of atherosclerotic plaques, which is the region most prone to rupture, and may be involved in atherosclerotic plaque destabilization (Johnson, J. L. et al., *Arterioscler. Thromb. Vasc. Biol.* 18:1707-1715, 1998). Furthermore, MMP-1 has been implicated in the pathogenesis of myocardial reperfusion injury (Shibata, M. et al., *Angiology* 50:573-582, 1999). Serum MMP-1 may be elevated inflammatory conditions that induce mast cell degranulation. Serum MMP-1 concentrations are elevated in patients with arthritis and systemic lupus erythematosus (Keyszer, G. et al., *Z Rheumatol* 57:392-398, 1998; Keyszer, G. *J. Rheumatol.* 26:251-258, 1999). Serum MMP-1 also is elevated in patients with prostate cancer, and the degree of elevation corresponds to the metastatic potential of the tumor (Baker, T. et al., *Br. J. Cancer* 70:506-512, 1994). The serum concentration of MMP-1 may also be elevated in patients with other types of cancer. Serum MMP-1 is decreased in patients with hemochromatosis and also in patients with chronic viral hepatitis, where the concentration is inversely related to the severity (George, D. K. et al., *Gut* 42:715-720, 1998; Murawaki, Y. et al., *J. Gastroenterol. Hepatol.* 14:138-145, 1999). Serum MMP-1 was decreased in the first four days following acute myocardial infarction, and increased thereafter, reaching peak levels 2 weeks after the onset of acute myocardial infarction (George, D. K. et al., *Gut* 42:715-720, 1998).

Matrix metalloproteinase-2 (MMP-2), also called gelatinase A, is a 66 kDa zinc- and calcium-binding proteinase that is synthesized as an inactive 72 kDa precursor. Mature MMP-3 cleaves type I gelatin and collagen of types IV, V, VII, and X. MMP-2 is synthesized by a variety of cells, including vascular smooth muscle cells, mast cells, macrophage-derived foam cells, T lymphocytes, and endothelial cells (Johnson, J. L. et al., *Arterioscler. Thromb. Vasc. Biol.* 18:1707-1715, 1998). MMP-2 is usually found in plasma in complex with TIMP-2, its physiological regulator (Murawaki, Y. et al., *J. Hepatol.* 30:1090-1098, 1999). The normal plasma concentration of MMP-2 is <~550 ng/ml (8 nM). MMP-2 expression is elevated in vascular smooth muscle cells within atherosclerotic lesions, and it may be released into the bloodstream in cases of plaque instability (Kai, H. et al., *J. Am. Coll. Cardiol.* 32:368-372, 1998). Furthermore, MMP-2 has been implicated as a contributor to plaque instability and rupture (Shah, P. K. et al., *Circulation* 92:1565-1569, 1995). Serum MMP-2 concentrations were elevated in patients with stable angina, unstable angina, and acute myocardial infarction, with elevations being significantly greater in unstable angina and acute myocardial infarction than in stable angina (Kai, H. et al., *J. Am. Coll. Cardiol.* 32:368-372, 1998). There was no change in the serum MMP-2 concentration in individuals with stable angina following a treadmill exercise test (Kai, H. et al., *J. Am. Coll. Cardiol.* 32:368-372, 1998). Serum and plasma MMP-2 is elevated in patients with gastric cancer, hepatocellular carcinoma, liver cirrhosis, urothelial carcinoma, rheumatoid arthritis, and lung cancer (Murawaki, Y. et al., *J. Hepatol.* 30:1090-1098, 1999; Endo, K. et al., *Anticancer Res.* 17:2253-2258, 1997; Gohji, K. et al., *Cancer* 78:2379-2387, 1996; Gruber, B. L. et al., *Clin. Immunol. Immunopathol.* 78:161-171, 1996; Garbisa, S. et al., *Cancer Res.* 52:4548-4549, 1992). Furthermore, MMP-2 may also be translocated from the platelet cytosol to the extracellular space during platelet aggregation (Sawicki, G. et al., *Thromb. Haemost.* 80:836-839, 1998). MMP-2 was elevated on admission in the serum of individuals with unstable angina and acute myocardial infarction, with maximum levels approaching 1.5 μg/ml (25 nM) (Kai, H. et al., *J. Am. Coll. Cardiol.* 32:368-372, 1998). The serum MMP-2 concentration peaked 1-3 days after onset in both unstable angina and acute myocardial infarction, and started to return to normal after 1 week (Kai, H. et al., *J. Am. Coll. Cardiol.* 32:368-372, 1998).

Matrix metalloproteinase-3 (MMP-3), also called stromelysin-1, is a 45 kDa zinc- and calcium-binding proteinase that is synthesized as an inactive 60 kDa precursor. Mature MMP-3 cleaves proteoglycan, fibrinectin, laminin, and type IV collagen, but not type I collagen. MMP-3 is synthesized by a variety of cells, including smooth muscle cells, mast cells, macrophage-derived foam cells, T lymphocytes, and endothelial cells (Johnson, J. L. et al., *Arterioscler. Thromb. Vasc. Biol.* 18:1707-1715, 1998). MMP-3, like other MMPs, is involved in extracellular matrix remodeling, which can occur following injury or during intervascular cell migration. MMP-3 is normally found at a concentration of <125 ng/ml in plasma. The serum MMP-3 concentration also has been shown to increase with age, and the concentration in males is approximately 2 times higher in males than in females (Manicourt, D. H. et al., *Arthritis Rheum.* 37:1774-1783, 1994). MMP-3 is found in the shoulder region of atherosclerotic plaques, which is the region most prone to rupture, and may be involved in atherosclerotic plaque destabilization (Johnson, J. L. et al., *Arterioscler. Thromb. Vasc. Biol.* 18:1707-1715, 1998). Therefore, MMP-3 concentration may be elevated as a result of atherosclerotic plaque rupture in unstable angina. Serum MMP-3 may be elevated inflammatory conditions that induce mast cell degranulation. Serum MMP-3 concentrations are elevated in patients with arthritis and systemic lupus erythematosus (Zucker, S. et al. *J. Rheumatol.* 26:78-80, 1999; Keyszer, G. et al., *Z Rheumatol.* 57:392-398, 1998; Keyszer, G. et al. *J. Rheumatol.* 26:251-258, 1999). Serum MMP-3 also is elevated in patients with prostate and urothelial cancer, and also glomerulonephritis (Lein, M. et al., *Urologe A* 37:377-381, 1998; Gohji, K. et al., *Cancer* 78:2379-2387, 1996; Akiyama, K. et al., *Res. Com-* mun. Mol. Pathol. Pharmacol. 95:115-128, 1997). The serum concentration of MMP-3 may also be elevated in patients with other types of cancer. Serum MMP-3 is decreased in patients with hemochromatosis (George, D. K. et al., *Gut* 42:715-720, 1998).

Matrix metalloproteinase-9 (MMP-9) also called gelatinase B, is an 84 kDa zinc- and calcium-binding proteinase that is synthesized as an inactive 92 kDa precursor. Mature MMP-9 cleaves gelatin types I and V, and collagen types IV and V. MMP-9 exists as a monomer, a homodimer, and a heterodimer with a 25 kDa $a_2$-microglobulin-related protein (Triebel, S. et al., *FEBS Lett.* 314:386-388, 1992). MMP-9 is synthesized by a variety of cell types, most notably by neutrophils. The normal plasma concentration of MMP-9 is <35 ng/ml (400 pM). MMP-9 expression is elevated in vascular smooth muscle cells within atherosclerotic lesions, and it may be released into the bloodstream in cases of plaque instability (Kai, H. et al., *J. Am. Coll. Cardiol.* 32:368-372, 1998). Furthermore, MMP-9 may have a pathogenic role in the development of ACS (Brown, D. L. et al., *Circulation* 91:2125-2131, 1995). Plasma MMP-9 concentrations are significantly elevated in patients with unstable angina and acute myocardial infarction, but not stable angina (Kai, H. et al., *J. Am. Coll. Cardiol.* 32:368-372, 1998). The elevations in patients with acute myocardial infarction may also indicate that those individuals were suffering from unstable angina. Elevations in the plasma concentration of MMP-9 may also be greater in unstable angina than in acute myocardial infarction. There was no significant change in plasma MMP-9 levels after a treadmill exercise test in patients with stable angina (Kai, H. et al., *J. Am. Coll. Cardiol.* 32:368-372, 1998). Plasma MMP-9 is elevated in individuals with rheumatoid arthritis, septic shock, giant cell arteritis and various carcinomas (Gruber, B. L. et al., *Clin. Immunol. Immunopathol.* 78:161-171, 1996; Nakamura, T. et al., *Am. J. Med. Sci.* 316:355-360, 1998; Blankaert, D. et al., *J. Acquir. Immune Defic. Syndr. Hum. Retrovirol.* 18:203-209, 1998; Endo, K. et al., *Anticancer Res.* 17:2253-2258, 1997; Hayasaka, A. et al., *Hepatology* 24:1058-1062, 1996; Moore, D. H. et al., *Gynecol. Oncol.* 65:78-82, 1997; Sorbi, D. et al., *Arthritis Rheum.* 39:1747-1753, 1996; Iizasa, T. et al., *Clin., Cancer Res.*, 5:149-153, 1999). Furthermore, the plasma MMP-9 concentration may be elevated in stroke and cerebral hemorrhage (Mun-Bryce, S. and Rosenberg, G. A., *J. Cereb. Blood Flow Metab.* 18:1163-1172, 1998; Romanic, A. M. et al., *Stroke* 29:1020-1030, 1998; Rosenberg, G. A., *J. Neurotrauma* 12:833-842, 1995). MMP-9 was elevated on admission in the serum of individuals with unstable angina and acute myocardial infarction, with maximum levels approaching 150 ng/ml (1.7 nM) (Kai, H. et al., *J. Am. Coll. Cardiol.* 32:368-372, 1998). The serum MMP-9 concentration was highest on admission in patients unstable angina, and the concentration decreased gradually after treatment, approaching baseline more than 1 week after onset (Kai, H. et al., *J. Am. Coll. Cardiol.* 32:368-372, 1998).

The balance between matrix metalloproteinases and their inhibitors is a critical factor which affects tumor invasion and metastasis. The TIMP family represents a class of small (21-28 kDa) related proteins that inhibit the metalloproteinases. Tissue inhibitor of metalloproteinase 1 (TIMP1) is reportedly involved in the regulation of bone modeling and remodeling in normal developing human bone, involved in the invasive phenotype of acute myelogenous leukemia, demonstrating polymorphic. X-chromosome inactivation. TIMP1 is known to act on mmp-1, mmp-2, mmp-3, mmp-7, mmp-8, mmp-9, mmp-10, mmp-11, mmp-12, mmp-13 and mmp-16. Tissue inhibitor of metalloproteinase 2 (TIMP2) complexes with metalloproteinases (such as collagenases) and irreversibly inactivates them. TIMP 2 is known to act on mmp-1, mmp-2, mmp-3, mmp-7, mmp-8, mmp-9, mmp-10, mmp-13, mmp-14, mmp-15, mmp-16 and mmp-19. Two alternatively spliced forms may be associated with SYN4, and involved in the invasive phenotype of acute myelogenous leukemia. Unlike the inducible expression of some other TIMP gene family members, the expression of this gene is largely constitutive. Tissue inhibitor of metalloproteinase 3 (TIMP3) antagonizes matrix metalloproteinase activity and can suppress tumor growth, angiogenesis, invasion, and metastasis. Loss of TIMP-3 has been related to the acquisition of tumorigenesis.

(iv) Exemplary Markers Related to Tissue Injury and Inflammation

Pulmonary surfactant protein D (SP-D) is a 43 kDa protein synthesized and secreted into the airspaces of the lung by the respiratory epithelium. At the alveolar level, SP-D is constitutively synthesized and secreted by alveolar type II cells. SP-D, a collagenous calcium-dependent lectin (or collectin), binds to surface glycoconjugates expressed by a wide variety of microorganisms, and to oligosaccharides associated with the surface of various complex organic antigens. SP-D also specifically interacts with glycoconjugates and other molecules expressed on the surface of macrophages, neutrophils, and lymphocytes. In addition, SP-D binds to specific surfactant-associated lipids and can influence the organization of lipid mixtures containing phosphatidylinositol in vitro. Consistent with these diverse in vitro activities is the observation that SP-D-deficient transgenic mice show abnormal accumulations of surfactant lipids, and respond abnormally to challenge with respiratory viruses and bacterial lipopolysaccharides. The phenotype of macrophages isolated from the lungs of SP-D-deficient mice is altered, and there is circumstantial evidence that abnormal oxidant metabolism and/or increased metalloproteinase expression contributes to the development of emphysema. The expression of SP-D is increased in response to many forms of lung injury, and deficient accumulation of appropriately oligomerized SP-D might contribute to the pathogenesis of a variety of human lung diseases. See, e.g., Crouch, Respir. Res. 1: 93-108 (2000).

C-reactive protein is a (CRP) is a homopentameric $Ca^{2+}$-binding acute phase protein with 21 kDa subunits that is involved in host defense. CRP preferentially binds to phosphorylcholine, a common constituent of microbial membranes. Phosphorylcholine is also found in mammalian cell membranes, but it is not present in a form that is reactive with CRP. The interaction of CRP with phosphorylcholine promotes agglutination and opsonization of bacteria, as well as activation of the complement cascade, all of which are involved in bacterial clearance. Furthermore, CRP can interact with DNA and histones, and it has been suggested that CRP is a scavenger of nuclear material released from damaged cells into the circulation (Robey, F. A. et al., *J. Biol. Chem.* 259:7311-7316, 1984). CRP synthesis is induced by 11-6, and indirectly by IL-1, since IL-1 can trigger the synthesis of IL-6 by Kupffer cells in the hepatic sinusoids. The normal plasma concentration of CRP is <3 µg/ml (30 nM) in 90% of the healthy population, and <10 µg/ml (100 nM) in 99% of healthy individuals. Plasma CRP concentrations can be measured by rate nephelometry or ELISA. The plasma concentration of CRP is significantly elevated in patients with acute myocardial infarction and unstable angina, but not stable angina (Biasucci, L. M. et al, *Circulation* 94:874-877, 1996; Biasucci, L. M. et al., *Am. J. Cardiol.* 77:85-87, 1996; Benamer, H. et al., *Am. J. Cardiol.* 82:845-850, 1998; Caligiuri, G. et al., *J. Am. Coll. Cardiol.* 32:1295-1304, 1998; Curzen, N. P. et al., *Heart* 80:23-27, 1998; Dangas, G. et al.,

*Am. J. Cardiol.* 83:583-5, A7, 1999). CRP may also be elevated in the plasma of individuals with variant or resolving unstable angina, but mixed results have been reported (Benamer, H. et al., *Am. J. Cardiol.* 82:845-850, 1998; Caligiuri, G. et al., *J. Am. Coll. Cardiol.* 32:1295-1304, 1998). The concentration of CRP will be elevated in the plasma from individuals with any condition that may elicit an acute phase response, such as infection, surgery, trauma, and stroke. CRP is a secreted protein that is released into the bloodstream soon after synthesis. CRP synthesis is upregulated by IL-6, and the plasma CRP concentration is significantly elevated within 6 hours of stimulation (Biasucci, L. M. et al., *Am. J. Cardiol.* 77:85-87, 1996). The plasma CRP concentration peaks approximately 50 hours after stimulation, and begins to decrease with a half-life of approximately 19 hours in the bloodstream (Biasucci, L. M. et al., *Am. J. Cardiol.* 77:85-87, 1996). Other investigations have confirmed that the plasma CRP concentration in individuals with unstable angina (Biasucci, L. M. et al., *Circulation* 94:874-877, 1996). The plasma concentration of CRP can approach 100 µg/ml (1 µM) in individuals with ACS (Biasucci, L. M. et al., *Circulation* 94:874-877, 1996; Liuzzo, G. et al., *Circulation* 94:2373-2380, 1996). CRP is a specific marker of the acute phase response. Elevations of CRP have been identified in the plasma of individuals with acute myocardial infarction and unstable angina, most likely as a result of activation of the acute phase response associated with atherosclerotic plaque rupture or cardiac tissue injury.

Interleukin-1β (IL-1β) is a 17 kDa secreted proinflammatory cytokine that is involved in the acute phase response and is a pathogenic mediator of many diseases. IL-1β is normally produced by macrophages and epithelial cells. IL-1β is also released from cells undergoing apoptosis. The normal serum concentration of IL-1β is <30 pg/ml (1.8 pM). In theory, IL-1β would be elevated earlier than other acute phase proteins such as CRP in unstable angina and acute myocardial infarction, since IL-1β is an early participant in the acute phase response. Furthermore, IL-1β is released from cells undergoing apoptosis, which may be activated in the early stages of ischemia. In this regard, elevation of the plasma IL-1β concentration associated with ACS requires further investigation using a high-sensitivity assay. Elevations of the plasma IL-1β concentration are associated with activation of the acute phase response in proinflammatory conditions such as trauma and infection. IL-1β has a biphasic physiological half-life of 5 minutes followed by 4 hours (Kudo, S. et al., *Cancer Res.* 50:5751-5755, 1990). IL-1β is released into the extracellular milieu upon activation of the inflammatory response or apoptosis.

Interleukin-1 receptor antagonist (IL-1ra) is a 17 kDa member of the IL-1 family predominantly expressed in hepatocytes, epithelial cells, monocytes, macrophages, and neutrophils. IL-1ra has both intracellular and extracellular forms produced through alternative splicing. IL-1ra is thought to participate in the regulation of physiological IL-1 activity. IL-1ra has no IL-1-like physiological activity, but is able to bind the IL-1 receptor on T-cells and fibroblasts with an affinity similar to that of IL-1β, blocking the binding of IL-1α and IL-1β and inhibiting their bioactivity (Stockman, B. J. et al., *Biochemistry* 31:5237-5245, 1992; Eisenberg, S. P. et al., *Proc. Natl. Acad. Sci. U.S.A.* 88:5232-5236, 1991; Carter, D. B. et al., *Nature* 344:633-638, 1990). IL-1ra is normally present in higher concentrations than IL-1 in plasma, and it has been suggested that IL-1ra levels are a better correlate of disease severity than IL-1 (Biasucci, L. M. et al., *Circulation* 99:2079-2084, 1999). Furthermore, there is evidence that IL-1ra is an acute phase protein (Gabay, C. et al., *J. Clin. Invest.* 99:2930-2940, 1997). The normal plasma concentration of IL-1ra is <200 pg/ml (12 pM). The plasma concentration of IL-1ra is elevated in patients with acute myocardial infarction and unstable angina that proceeded to acute myocardial infarction, death, or refractory angina (Biasucci, L. M. et al., *Circulation* 99:2079-2084, 1999; Latini, R. et al., *J. Cardiovasc. Pharmacol.* 23:1-6, 1994). Furthermore, IL-1ra was significantly elevated in severe acute myocardial infarction as compared to uncomplicated acute myocardial infarction (Latini, R. et al., *J. Cardiovasc. Pharmacol.* 23:1-6, 1994). Elevations in the plasma concentration of IL-1ra are associated with any condition that involves activation of the inflammatory or acute phase response, including infection, trauma, and arthritis. IL-1ra is released into the bloodstream in pro-inflammatory conditions, and it may also be released as a participant in the acute phase response. The major sources of clearance of IL-1ra from the bloodstream appear to be kidney and liver (Kim, D. C. et al., *J. Pharm. Sci.* 84:575-580, 1995). IL-1ra concentrations were elevated in the plasma of individuals with unstable angina within 24 hours of onset, and these elevations may even be evident within 2 hours of onset (Biasucci, L. M. et al., *Circulation* 99:2079-2084, 1999). In patients with severe progression of unstable angina, the plasma concentration of IL-1ra was higher 48 hours after onset than levels at admission, while the concentration decreased in patients with uneventful progression (Biasucci, L. M. et al., *Circulation* 99:2079-2084, 1999). In addition, the plasma concentration of IL-1ra associated with unstable angina can approach 1.4 ng/ml (80 pM). Changes in the plasma concentration of IL-1ra appear to be related to disease severity. Furthermore, it is likely released in conjunction with or soon after IL-1 release in pro-inflammatory conditions, and it is found at higher concentrations than IL-1. This indicates that IL-1ra may be a useful indirect marker of IL-1 activity, which elicits the production of IL-6.

Interleukin-6 (IL-6) is a 20 kDa secreted protein that is a hematopoietin family proinflammatory cytokine. IL-6 is an acute-phase reactant and stimulates the synthesis of a variety of proteins, including adhesion molecules. Its major function is to mediate the acute phase production of hepatic proteins, and its synthesis is induced by the cytokine IL-1. IL-6 is normally produced by macrophages and T lymphocytes. The normal serum concentration of IL-6 is <3 pg/ml (0.15 pM). The plasma concentration of IL-6 is elevated in patients with acute myocardial infarction and unstable angina, to a greater degree in acute myocardial infarction (Biasucci, L. M. et al., *Circulation* 94:874-877, 1996; Manten, A. et al., *Cardiovasc. Res.* 40:389-395, 1998; Biasucci, L. M. et al., *Circulation* 99:2079-2084, 1999). IL-6 is not significantly elevated in the plasma of patients with stable angina (Biasucci, L. M. et al., *Circulation* 94:874-877, 1996; Manten, A. et al., *Cardiovasc. Res.* 40:389-395, 1998). Furthermore, IL-6 concentrations increase over 48 hours from onset in the plasma of patients with unstable angina with severe progression, but decrease in those with uneventful progression (Biasucci, L. M. et al., *Circulation* 99:2079-2084, 1999). This indicates that IL-6 may be a useful indicator of disease progression. Plasma elevations of IL-6 are associated with any nonspecific proinflammatory condition such as trauma, infection, or other diseases that elicit an acute phase response. IL-6 has a half-life of 4.2 hours in the bloodstream and is elevated following acute myocardial infarction and unstable angina (Manten, A. et al., *Cardiovasc. Res.* 40:389-395, 1998). The plasma concentration of IL-6 is elevated within 8-12 hours of acute myocardial infarction onset, and can approach 100 pg/ml. The plasma concentration of IL-6 in patients with unstable angina was elevated at peak levels 72 hours after onset, possibly due to the severity of insult (Biasucci, L. M. et al., *Circulation* 94:874-877, 1996).

Tumor necrosis factor α (TNFα) is a 17 kDa secreted proinflammatory cytokine that is involved in the acute phase response and is a pathogenic mediator of many diseases. TNFα is normally produced by macrophages and natural killer cells. TNF-alpha is a protein of 185 amino acids glycosylated at positions 73 and 172. It is synthesized as a precursor protein of 212 amino acids. Monocytes express at least five different molecular forms of TNF-alpha with molecular masses of 21.5-28 kDa. They mainly differ by post-translational alterations such as glycosylation and phosphorylation. The normal serum concentration of TNFα is <40 pg/ml (2 pM). The plasma concentration of TNFα is elevated in patients with acute myocardial infarction, and is marginally elevated in patients with unstable angina (Li, D. et al., *Am. Heart J.* 137:1145-1152, 1999; Squadrito, F. et al., *Inflamm. Res.* 45:14-19, 1996; Latini, R. et al., *J. Cardiovasc. Pharmacol.* 23:1-6, 1994; Carlstedt, F. et al., *J. Intern. Med.* 242: 361-365, 1997). Elevations in the plasma concentration of TNFα are associated with any proinflammatory condition, including trauma, stroke, and infection. TNFα has a half-life of approximately 1 hour in the bloodstream, indicating that it may be removed from the circulation soon after symptom onset. In patients with acute myocardial infarction, TNFα was elevated 4 hours after the onset of chest pain, and gradually declined to normal levels within 48 hours of onset (Li, D. et al., *Am. Heart J.* 137:1145-1152, 1999). The concentration of TNFα in the plasma of acute myocardial infarction patients exceeded 300 pg/ml (15 pM) (Squadrito, F. et al., *Inflamm. Res.* 45:14-19, 1996). Release of TNFα by monocytes has also been related to the progression of pneumoconiosis in caol workers. Schins and Borm, Occup. Environ. Med. 52: 441-50 (1995).

Soluble intercellular adhesion molecule (sICAM-1), also called CD54, is a 85-110 kDa cell surface-bound immunoglobulin-like integrin ligand that facilitates binding of leukocytes to antigen-presenting cells and endothelial cells during leukocyte recruitment and migration. sICAM-1 is normally produced by vascular endothelium, hematopoietic stem cells and non-hematopoietic stem cells, which can be found in intestine and epidermis. sICAM-1 can be released from the cell surface during cell death or as a result of proteolytic activity. The normal plasma concentration of sICAM-1 is approximately 250 ng/ml (2.9 nM). The plasma concentration of sICAM-1 is significantly elevated in patients with acute myocardial infarction and unstable angina, but not stable angina (Pellegatta, F. et al., *J. Cardiovasc. Pharmacol.* 30:455-460, 1997; Miwa, K. et al., *Cardiovasc. Res.* 36:37-44, 1997; Ghaisas, N. K. et al., *Am. J. Cardiol.* 80:617-619, 1997; Ogawa, H. et al., *Am. J. Cardiol.* 83:38-42, 1999). Furthermore, ICAM-1 is expressed in atherosclerotic lesions and in areas predisposed to lesion formation, so it may be released into the bloodstream upon plaque rupture (Iiyama, K. et al., *Circ. Res.* 85:199-207, 1999; Tenaglia, A. N. et al., *Am. J. Cardiol.* 79:742-747, 1997). Elevations of the plasma concentration of sICAM-1 are associated with ischemic stroke, head trauma, atherosclerosis, cancer, preeclampsia, multiple sclerosis, cystic fibrosis, and other nonspecific inflammatory states (Kim, J. S., *J. Neurol. Sci.* 137:69-78, 1996; Laskowitz, D. T. et al., *J. Stroke Cerebrovasc. Dis.* 7:234-241, 1998). The plasma concentration of sICAM-1 is elevated during the acute stage of acute myocardial infarction and unstable angina. The elevation of plasma sICAM-1 reaches its peak within 9-12 hours of acute myocardial infarction onset, and returns to normal levels within 24 hours (Pellegatta, F. et al., *J. Cardiovasc. Pharmacol.* 30:455-460, 1997). The plasma concentration of sICAM can approach 700 ng/ml (8 nM) in patients with acute myocardial infarction (Pellegatta, F. et al., *J. Cardiovasc. Pharmacol.* 30:455-460, 1997). sICAM-1 is elevated in the plasma of individuals with acute myocardial infarction and unstable angina, but it is not specific for these diseases. It may, however, be useful marker in the differentiation of acute myocardial infarction and unstable angina from stable angina since plasma elevations are not associated with stable angina. Interestingly, ICAM-1 is present in atherosclerotic plaques, and may be released into the bloodstream upon plaque rupture.

Vascular cell adhesion molecule (VCAM), also called CD106, is a 100-110 kDa cell surface-bound immunoglobulin-like integrin ligand that facilitates binding of B lymphocytes and developing T lymphocytes to antigen-presenting cells during lymphocyte recruitment. VCAM is normally produced by endothelial cells, which line blood and lymph vessels, the heart, and other body cavities. VCAM-1 can be released from the cell surface during cell death or as a result of proteolytic activity. The normal serum concentration of sVCAM is approximately 650 ng/ml (6.5 nM). The plasma concentration of sVCAM-1 is marginally elevated in patients with acute myocardial infarction, unstable angina, and stable angina (Mulvihill, N. et al., *Am. J. Cardiol.* 83:1265-7, A9, 1999; Ghaisas, N. K. et al., *Am. J. Cardiol.* 80:617-619, 1997). However, sVCAM-1 is expressed in atherosclerotic lesions and its plasma concentration may correlate with the extent of atherosclerosis (Iiyama, K. et al., *Circ. Res.* 85:199-207, 1999; Peter, K. et al., *Arterioscler. Thromb. Vasc. Biol.* 17:505-512, 1997). Elevations in the plasma concentration of sVCAM-1 are associated with ischemic stroke, cancer, diabetes, preeclampsia, vascular injury, and other nonspecific inflammatory states (Bitsch, A. et al., *Stroke* 29:2129-2135, 1998; Otsuki, M. et al., *Diabetes* 46:2096-2101, 1997; Banks, R. E. et al., *Br. J. Cancer* 68:122-124, 1993; Steiner, M. et al., *Thromb. Hemost.* 72:979-984, 1994; Austgulen, R. et al., *Eur. J. Obstet. Gynecol. Reprod. Biol.* 71:53-58, 1997).

Monocyte chemotactic protein-1 (MCP-1) is a 10 kDa chemotactic factor that attracts monocytes and basophils, but not neutrophils or eosiniphils. MCP-1 is normally found in equilibrium between a monomeric and homodimeric form, and it is normally produced in and secreted by monocytes and vascular endothelial cells (Yoshimura, T. et al., *FEBS Lett.* 244:487-493, 1989; Li, Y. S. et al., *Mol. Cell. Biochem.* 126: 61-68, 1993). MCP-1 has been implicated in the pathogenesis of a variety of diseases that involve monocyte infiltration, including psoriasis, rheumatoid arthritis, and atherosclerosis. The normal concentration of MCP-1 in plasma is <0.1 ng/ml. The plasma concentration of MCP-1 is elevated in patients with acute myocardial infarction, and may be elevated in the plasma of patients with unstable angina, but no elevations are associated with stable angina (Soejima, H. et al., *J. Am. Coll. Cardiol.* 34:983-988, 1999; Nishiyama, K. et al., *Jpn. Circ. J.* 62:710-712, 1998; Matsumori, A. et al., *J. Mol. Cell. Cardiol.* 29:419-423, 1997). Interestingly, MCP-1 also may be involved in the recruitment of monocytes into the arterial wall during atherosclerosis. Elevations of the serum concentration of MCP-1 are associated with various conditions associated with inflammation, including alcoholic liver disease, interstitial lung disease, sepsis, and systemic lupus erythematosus (Fisher, N. C. et al., *Gut* 45:416-420, 1999; Suga, M. et al., *Eur. Respir. J.* 14:376-382, 1999; Bossink, A. W. et al., *Blood* 86:3841-3847, 1995; Kaneko, H. et al. *J. Rheumatol.* 26:568-573, 1999). MCP-1 is released into the bloodstream upon activation of monocytes and endothelial cells. The concentration of MCP-1 in plasma form patients with acute myocardial infarction has been reported to approach 1 ng/ml (100 pM), and can remain elevated for one month (Soejima, H. et al., *J. Am. Coll. Cardiol.* 34:983-988, 1999). MCP-1 is a specific marker of the presence of a pro-inflammatory condition that involves monocyte migration.

Caspase-3, also called CPP-32, YAMA, and apopain, is an interleukin-1β converting enzyme (ICE)-like intracellular cysteine proteinase that is activated during cellular apoptosis. Caspase-3 is present as an inactive 32 kDa precursor that is proteolytically activated during apoptosis induction into a heterodimer of 20 kDa and 11 kDa subunits (Femandes-Alnemri, T. et al., *J. Biol. Chem.* 269:30761-30764, 1994). Its cellular substrates include poly(ADP-ribose) polymerase (PARP) and sterol regulatory element binding proteins (SREBPs) (Liu, X. et al., *J. Biol. Chem.* 271:13371-13376, 1996). The normal plasma concentration of caspase-3 is unknown. There are no published investigations into changes in the plasma concentration of caspase-3 associated with ACS. There are increasing amounts of evidence supporting the hypothesis of apoptosis induction in cardiac myocytes associated with ischemia and hypoxia (Saraste, A., *Herz* 24:189-195, 1999; Ohtsuka, T. et al., *Coron. Artery Dis.* 10:221-225, 1999; James, T. N., *Coron. Artery Dis.* 9:291-307, 1998; Bialik, S. et al., *J. Clin. Invest.* 100:1363-1372, 1997; Long, X. et al., *J. Clin. Invest.* 99:2635-2643, 1997). Elevations in the plasma caspase-3 concentration may be associated with any physiological event that involves apoptosis. There is evidence that suggests apoptosis is induced in skeletal muscle during and following exercise and in cerebral ischemia (Carraro, U. and Franceschi, C., *Aging (Milano)* 9:19-34, 1997; MacManus, J. P. et al., *J. Cereb. Blood Flow Metab.* 19:502-510, 1999).

Hemoglobin (Hb) is an oxygen-carrying iron-containing globular protein found in erythrocytes. It is a heterodimer of two globin subunits. $\alpha_1\gamma_2$ is referred to as fetal Hb, $\alpha_2\beta_2$ is called adult HbA, and $\alpha_2\beta_2$ is called adult $HbA_2$. 90-95% of hemoglobin is HbA, and the $\alpha_2$ globin chain is found in all Hb types, even sickle cell hemoglobin. Hb is responsible for carrying oxygen to cells throughout the body. $Hb\alpha_2$ is not normally detected in serum.

Human lipocalin-type prostaglandin D synthase (hPDGS), also called β-trace, is a 30 kDa glycoprotein that catalyzes the formation of prostaglandin D2 from prostaglandin H. The upper limit of hPDGS concentrations in apparently healthy individuals is reported to be approximately 420 ng/ml (Patent No. EP0999447A1). Elevations of hPDGS have been identified in blood from patients with unstable angina and cerebral infarction (Patent No. EP0999447A1). Furthermore, hPDGS appears to be a useful marker of ischemic episodes, and concentrations of hPDGS were found to decrease over time in a patient with angina pectoris following percutaneous transluminal coronary angioplasty (PTCA), suggesting that the hPGDS concentration decreases as ischemia is resolved (Patent No. EP0999447A1).

Mast cell tryptase, also known as alpha tryptase, is a 275 amino acid (30.7 kDa) protein that is the major neutral protease present in mast cells. Mast cell tryptase is a specific marker for mast cell activation, and is a marker of allergic airway inflammation in asthma and in allergic reactions to a diverse set of allergens. See, e.g., Taira et al., *J. Asthma* 39: 315-22 (2002); Schwartz et al., *N. Engl. J. Med.* 316: 1622-26 (1987). Elevated serum tryptase levels (>1 ng/mL) between 1 and 6 hours after an event provides a specific indication of mast cell degranulation.

Eosinophil cationic protein (ECP) is a heterogeneous protein with molecular weight variants from 16-24 kDa and a pI of pH 10.8. ECP is highly cytotoxic and is released by activated eosinophils. Venge, *Clinical and experimental allergy*, 23 (suppl. 2): 3-7 (1993). Concentrations of ECP in the bronchoalveolar lavage fluid (BALF) of asthma patients vary with the severity of their disease, and ECP concentrations in sputum have also been shown to reflect the pathophysiology of the disease. Bousquet et al., *New Engl. J Med.* 323: 1033-9 (1990). Virchow et al., *Am. Rev. Respir. Dis.* 146: 604-6 (1992). Assessment of serum ECP may be assumed to reflect pulmonary inflammation in bronchial asthma. Koller et al., *Arch. Dis. Childhood* 73: 413-7 (1995); see also, Sorkness et al., *Clin. Exp. Allergy* 32: 1355-59 (2002); Badr-elDin et al., East Mediterr. Health J. 5: 664-75 (1999).

KL-6 (also referred to as MUC1) is a high molecular weight (>300 kDa) mucinous glycoprotein expressed on pneumonocytes. Serum levels of KL-6 are reportedly elevated in interstitial lung diseases, which are characterized by exertional dyspnea. KL-6 has been shown to be a marker of various interstitial lung diseases, including pulmonary fibrosis, interstitial pneumonia, sarcoidosis, and interstitial pneumonitis. See, e.g., Kobayashi and Kitamura, *Chest* 108: 311-15 (1995); Kohno, *J. Med. Invest.* 46: 151-58 (1999); Bandoh et al., *Ann. Rheum. Dis.* 59: 257-62 (2000); and Yamane et al., *J. Rheumatol.* 27: 930-4 (2000).

Procalcitonin is a 116 amino acid (14.5 kDa) protein encoded by the Calc-1 gene located on chromosome 11p 15.4. The Calc-1 gene produces two transcripts that are the result of alternative splicing events. Pre-procalcitonin contains a 25 amino acid signal peptide which is processed by C-cells in the thyrois to a 57 amino acid N-terminal fragment, a 32 amino acid calcitonin fragment, and a 21 amino acid katacalcin fragment. Procalcitonin is secreted intact as a glycosylated product by other body cells. Whicher et al., Ann. Clin. Biochem. 38: 483-93 (2001). Plasma procalcitonin has been identified as a marker of sepsis and its severity (Yukioka et al., Ann. Acad. Med. Singapore 30: 528-31 (2001)), with day 2 procalcitonin levels predictive of mortality (Pettila et al., Intensive Care Med. 28: 1220-25 (2002).

Interleukin 10 ("IL-10") is a 160 amino acid (18.5 kDa predicted mass) cytokine that is a member of the four α-helix bundle family of cytokines. In solution, IL-10 forms a homodimer having an apparent molecular weight of 39 kDa. The human IL-10 gene is located on chromosome 1. Viera et al., *Proc. Natl. Acad Sci. USA* 88: 1172-76 (1991); Kim et al., *J. Immunol.* 148: 3618-23 (1992). Overproduction of IL-10 has been identified as a marker in sepsis, and is predictive of severity and mortality. Gogos et al., *J. Infect. Dis.* 181: 176-80 (2000).

(v) Exemplary Specific Markers for Cerebral Injury

Adenylate kinase (AK) is a ubiquitous 22 kDa cytosolic enzyme that catalyzes the interconversion of ATP and AMP to ADP. Four isoforms of adenylate kinase have been identified in mammalian tissues (Yoneda, T. et al., *Brain Res Mol Brain Res* 62:187-195, 1998). The AK1 isoform is found in brain, skeletal muscle, heart, and aorta. The normal serum mass concentration of AK1 is currently unknown, because a functional assay is typically used to measure total AK concentration. The normal serum AK concentration is <5 units/liter and AK elevations have been performed using CSF (Bollensen, E. et al., *Acta Neurol Scand* 79:53-582, 1989). Serum AK1 appears to have the greatest specificity of the AK isoforms as a marker of cerebral injury. AK may be best suited as a cerebrospinal fluid marker of cerebral ischemia, where its dominant source would be neural tissue.

Neurotrophins are a family of growth factors expressed in the mammalian nervous system. Some examples include nerve growth factor (NGF), brain-derived neurotrophic factor (BDNF), neurotrophin-3 (NT-3) and neurotrophin-4/5 (NT- 4/5). Neurotrophins exert their effects primarily as target-derived paracrine or autocrine neurotrophic factors. The role of the neurotrophins in survival, differentiation and maintenance of neurons is well known. They exhibit partially overlapping but distinct patterns of expression and cellular targets. In addition to the effects in the central nervous system, neurotrophins also affect peripheral afferent and efferent neurons.

BDNF is a potent neurotrophic factor which supports the growth and survivability of nerve and/or glial cells. BDNF is expressed as a 32 kDa precursor "pro-BDNF" molecule that is cleaved to a mature BDNF form. Mowla et al., J. Biol. Chem. 276: 12660-6 (2001). The most abundant active form of human BDNF is a 27 kDa homodimer, formed by two identical 119 amino acid subunits, which is held together by strong hydrophobic interactions; however, pro-BDNF is also released extracellularly and is biologically active. BDNF is widely distributed throughout the CNS and displays in vitro trophic effects on a wide range of neuronal cells, including hippocampal, cerebellar, and cortical neurons. In vivo, BDNF has been found to rescue neural cells from traumatic and toxic brain injury. For example, studies have shown that after transient middle cerebral artery occlusion, BDNF mRNA is upregulated in cortical neurons (Schabiltz et al., J. Cereb. Blood Flow Metab. 14:500-506, 1997). In experimentally induced focal, unilateral thrombotic stroke, BDNF mRNA was increased from 2 to 18 h following the stroke. Such results suggest that BDNF potentially plays a neuroprotective role in focal cerebral ischemia.

NT-3 is also a 27 kDa homodimer consisting of two 119-amino acid subunits. The addition of NT-3 to primary cortical cell cultures has been shown to exacerbate neuronal death caused by oxygen-glucose deprivation, possible via oxygen free radical mechanisms (Bates et al., Neurobiol. Dis. 9:24-37, 2002). NT-3 is expressed as an inactive pro-NT-3 molecule, which is cleaved to the mature biologically active form.

Calbindin-D is a 28 kDa cytosolic vitamin D-dependent $Ca^{2+}$-binding protein that may serve a cellular protective function by stabilizing intracellular calcium levels. Calbindin-D is found in the central nervous system, mainly in glial cells, and in cells of the distal renal tubule (Hasegawa, S. et al., J. Urol. 149:1414-1418, 1993). The normal serum concentration of calbindin-D is <20 pg/ml (0.7 pM). Serum calbindin-D concentration is reportedly elevated following cardiac arrest, and this elevation is thought to be a result of CNS damage due to cerebral ischemia-(Usui, A. et al., J. Neurol. Sci. 123:134-139, 1994). Elevations of serum calbindin-D are elevated and plateau soon after reperfusion following ischemia. Maximum serum calbindin-D concentrations can be as much as 700 pg/ml (25 pM).

Creatine kinase (CK) is a cytosolic enzyme that catalyzes the reversible formation of ADP and phosphocreatine from ATP and creatine. The brain-specific CK isoform (CK-BB) is an 85 kDa cytosolic protein that accounts for approximately 95% of the total brain CK activity. It is also present in significant quantities in cardiac tissue, intestine, prostate, rectum, stomach, smooth muscle, thyroid uterus, urinary bladder, and veins (Johnsson, P. J., Cardiothorac. Vasc. Anesth. 10:120-126, 1996). The normal serum concentration of CK-BB is <10 ng/ml (120 pM). Serum CK-BB is elevated after hypoxic and ischemic brain injury, but a further investigation is needed to identify serum elevations in specific stroke types (Laskowitz, D. T. et al., J. Stroke Cerebrovasc. Dis. 7:234-241, 1998). Elevations of CK-BB in serum can be attributed to cerebral injury due to ischemia, coupled with increased permeability of the blood brain barrier. No correlation of the serum concentration of CK-BB with the extent of damage (infarct volume) or neurological outcome has been established. CK-BB has a half-life of 1-5 hours in serum and is normally detected in serum at a concentration of <10 ng/ml (120 pM). In severe stroke, serum concentrations CK-BB are elevated and peak soon after the onset of stroke (within 24 hours), gradually returning to normal after 3-7 days (4). CK-BB concentrations in the serum of individuals with head injury peak soon after injury and return to normal between 3.5-12 hours after injury, depending on the injury severity (Skogseid, I. M. et al., Acta Neurochir. (Wien.) 115:106-111, 1992). Maximum serum CK-BB concentrations can exceed 250 ng/ml (3 nM). CK-BB may be best suited as a CSF marker of cerebral ischemia, where its dominant source would be neural tissue. CKBB might be more suitable as a serum marker of CNS damage after head injury because it is elevated for a short time in these individuals, with its removal apparently dependent upon the severity of damage.

Glial fibrillary acidic protein (GFAP) is a 55 kDa cytosolic protein that is a major structural component of astroglial filaments and is the major intermediate filament protein in astrocytes. GFAP is specific to astrocytes, which are interstitial cells located in the CNS and can be found near the blood-brain barrier. GFAP is not normally detected in serum. Serum GFAP is elevated following ischemic stroke (Niebroj-Dobosz, I., et al., Folia Neuropathol. 32:129-137, 1994). Current reports investigating serum GFAP elevations associated with stroke are severely limited, and much further investigation is needed to establish GFAP as a serum marker for all stroke types. Most studies investigating GFAP as a stroke marker have been performed using cerebrospinal fluid. Elevations of GFAP in serum can be attributed to cerebral injury due to ischemia, coupled with increased permeability of the blood brain barrier. No correlation of the serum concentration of GFAP with the extent of damage (infarct volume) or neurological outcome has been established. GFAP is elevated in cerebrospinal fluid of individuals with various neuropathies affecting the CNS, but there are no reports currently available describing the release of GFAP into the serum of individuals with diseases other than stroke (Albrechtsen, M. and Bock, E. J., Neuroimmunol. 8:301-309, 1985). Serum concentrations GFAP appear to be elevated soon after the onset of stroke, continuously increase and persist for an amount of time (weeks) that may correlate with the severity of damage. GFAP appears to a very specific marker for severe CNS injury, specifically, injury to astrocytes due to cell death caused by ischemia or physical damage.

Lactate dehydrogenase (LDH) is a ubiquitous 135 kDa cytosolic enzyme. It is a tetramer of A and B chains that catalyzes the reduction of pyruvate by NADH to lactate. Five isoforms of LDH have been identified in mammalian tissues, and the tissue-specific isoforms are made of different combinations of A and B chains. The normal serum mass concentration of LDH is currently unknown, because a functional assay is typically used to measure total LDH concentration. The normal serum LDH concentration is <600 units/liter (Ray, P. et al., Cancer Detect. Prev. 22:293-304, 1998). A great majority of investigations into LDH elevations in the context of stroke have been performed using cerebrospinal fluid, and elevations correlate with the severity of injury. Elevations in serum LDH activity are reported following both ischemic and hemorrhagic stroke, but further studies are needed in serum to confirm this observation and to determine a correlation with the severity of injury and neurological outcome (Aggarwal, S. P. et al., J. Indian Med. Assoc. 93:331-332, 1995; Maiuri, F. et al., Neurol. Res. 11:6-8, 1989). LDH may be best suited as a cerebrospinal fluid marker of cerebral ischemia, where its dominant source would be neural tissue.

Myelin basic protein (MBP) is actually a 14-21 kDa family of cytosolic proteins generated by alternative splicing of a single MBP gene that is likely involved in myelin compaction around axons during the myelination process. MBP is specific to oligodendrocytes in the CNS and in Schwann cells of the peripheral nervous system (PNS). It accounts for approximately 30% of the total myelin protein in the CNS and approximately 10% of the total myelin protein in the PNS. The normal serum concentration of MBP is <7 ng/ml (400 pM). Serum MBP is elevated after all types of severe stroke, specifically thrombotic stroke, embolic stroke, intracerebral hemorrhage, and subarachnoid hemorrhage, while elevations in MBP concentration are not reported in the serum of individuals with strokes of minor to moderate severity, which would include lacunar infarcts or transient ischemic attacks (Palfreyman, J. W. et al., *Clin. Chim. Acta* 92:403-409, 1979). Elevations of MBP in serum can be attributed to cerebral injury due to physical damage or ischemia caused by infarction or cerebral hemorrhage, coupled with increased permeability of the blood brain barrier. The serum concentration of MBP has been reported to correlate with the extent of damage (infarct volume), and it may also correlate with neurological outcome. The amount of available information regarding serum MBP elevations associated with stroke is limited, because most investigations have been performed using cerebrospinal fluid. MBP is normally detected in serum at an upper limit of 7 ng/ml (400 pM), is elevated after severe stroke and cerebral injury. Serum MBP is thought to be elevated within hours after stroke onset, with concentrations increasing to a maximum level within 2-5 days after onset. After the serum concentration reaches its maximum, which can exceed 120 ng/ml (6.9 nM), it can take over one week to gradually decrease to normal concentrations. Because the severity of damage has a direct effect on the release of MBP, it will affect the release kinetics by influencing the length of time that MBP is elevated in the serum. MBP will be present in the serum for a longer period of time as the severity of injury increases. The release of MBP into the serum of patients with head injury is thought to follow similar kinetics as those described for stroke, except that serum MBP concentrations reportedly correlate with the neurological outcome of individuals with head injury (Thomas, D. G. et al., *Acta Neurochir. Suppl.* (*Wien*) 28:93-95, 1979). The release of MBP into the serum of patients with intracranial tumors is thought to be persistent, but still needs investigation. Finally, serum MBP concentrations can sometimes be elevated in individuals with demyelinating diseases, but no conclusive investigations have been reported. As reported in individuals with multiple sclerosis, MBP is frequently elevated in the cerebrospinal fluid, but matched elevations in serum are often not present (Jacque, C. et al., *Arch. Neurol.* 39:557-560, 1982). This could indicate that cerebral damage has to be accompanied by an increase in the permeability of the blood-brain barrier to result in elevation of serum MBP concentrations. However, MBP can also be elevated in the population of individuals having intracranial tumors. The presence of these individuals in the larger population of individuals that would be candidates for an assay using this marker for stroke is rare. These individuals, in combination with individuals undergoing neurosurgical procedures or with demyelinating diseases, would nonetheless have an impact on determining the specificity of MBP for cerebral injury. Additionally, serum MBP may be useful as a marker of severe stroke, potentially identifying individuals that would not benefit from stroke therapies and treatments, such as tPA administration.

Neural cell adhesion molecule (NCAM), also called CD56, is a 170 kDa cell surface-bound immunoglobulin-like integrin ligand that is involved in the maintenance of neuronal and glial cell interactions in the nervous system, where it is expressed on the surface of astrocytes, oligodendrocytes, Schwann cells, neurons, and axons. NCAM is also localized to developing skeletal muscle myotubes, and its expression is upregulated in skeletal muscle during development, denervation and renervation. The normal serum mass concentration of NCAM has not been reported. NCAM is commonly measured by a functional enzyme immunoassay and is reported to have a normal serum concentration of <20 units/ml. Changes in serum NCAM concentrations specifically related to stroke have not been reported. NCAM may be best suited as a CSF marker of cerebral ischemia, where its dominant source would be neural tissue.

Enolase is a 78 kDa homo- or heterodimeric cytosolic protein produced from $\alpha$, $\beta$, and $\gamma$ subunits. It catalyzes the interconversion of 2-phosphoglycerate and phosphoenolpyruvate in the glycolytic pathway. Enolase can be present as $\alpha\alpha$, $\beta\beta$, $\alpha\gamma$, and $\gamma\gamma$ isoforms. The $\alpha$ subunit is found in glial cells and most other tissues, the $\beta$ subunit is found in muscle tissue, and the $\gamma$ subunit if found mainly in neuronal and neuroendocrine cells (Quinn, G. B. et al., *Clin. Chem.* 40:790-795, 1994). The $\gamma\gamma$ enolase isoform is most specific for neurons, and is referred to as neuron-specific enolase (NSE). NSE, found predominantly in neurons and neuroendocrine cells, is also present in platelets and erythrocytes. The normal serum concentration of NSE is <12.5 ng/ml (160 pM). NSE is made up of two subunits; thus, the most feasible immunological assay used to detect NSE concentrations would be one that is directed against one of the subunits. In this case, the $\gamma$ subunit would be the ideal choice. However, the $\gamma$ subunit alone is not as specific for cerebral tissue as the $\gamma\gamma$ isoform, since a measurement of the $\gamma$ subunit alone would detect both the $\gamma\gamma$ and $\gamma\gamma$ isoforms. In this regard, the best immunoassay for NSE would be a two-site assay that could specifically detect the $\gamma\gamma$ isoform. Serum NSE is reportedly elevated after all stroke types, including TIAs, which are cerebral in origin and are thought to predispose an individual to having a more severe stroke at a later date (Isgro, F. et al., *Eur. J. Cardiothorac. Surg.* 11:640-644, 1997). Elevations of NSE in serum can be attributed to cerebral injury due to physical damage or ischemia caused by infarction or cerebral hemorrhage, coupled with increased permeability of the blood brain barrier, and the serum concentration of NSE has been reported to correlate with the extent of damage (infarct volume) and neurological outcome (Martens, P. et al., *Stroke* 29:2363-2366, 1998). Additionally, a secondary elevation of serum NSE concentration may be an indicator of delayed neuronal injury resulting from cerebral vasospasm (Laskowitz, D. T. et al., *J. Stroke Cerebrovasc. Dis.* 7, 234-241, 1998). NSE, which has a biological half-life of 48 hours and is normally detected in serum at an upper limit of 12.5 ng/ml (160 pM), is elevated after stroke and cerebral injury. Serum NSE is elevated after 4 hours from stroke onset, with concentrations reaching a maximum 1-3 days after onset (Missler, U. et al., *Stroke* 28:1956-1960, 1997). After the serum concentration reaches its maximum, which can exceed 300 ng/ml (3.9 nM), it gradually decreases to normal concentrations over approximately one week. Because the severity of damage has a direct effect on the release of NSE, it will affect the release kinetics by influencing the length of time that NSE is elevated in the serum. NSE will be present in the serum for a longer period of time as the severity of injury increases. The release of NSE into the serum of patients with head injury follows different kinetics as seen with stroke, with the maximum serum concentration being reached within 1-6 hours after injury, often returning to baseline within 24 hours (Skogseid, I. M. et al., *Acta Neurochir. (Wien.)* 115:106-111, 1992). NSE is a specific marker for cerebral injury, specifically, injury to neuronal cells due to cell death caused by ischemia or physical damage. Neurons are about 10-fold less abundant in the brain than glial cells, so any cerebral injury coupled with increased permeability of the blood-brain barrier will have to occur in a region that has a significant regional population of neurons to significantly increase the serum NSE concentration. In addition, elevated serum concentrations of NSE can also indicate complications related to cerebral injury after AMI and cardiac surgery. Elevations in the serum concentration of NSE correlate with the severity of damage and the neurological outcome of the individual. NSE can be used as a marker of all stroke types, including TIAs. However, NSE cannot be used to differentiate ischemic and hemorrhagic stroke, and it is elevated in the population of individuals having tumors with neuroendocrine features.

Proteolipid protein (PLP) is a 30 kDa integral membrane protein that is a major structural component of CNS myelin. PLP is specific to oligodendrocytes in the CNS and accounts for approximately 50% of the total CNS myelin protein in the central sheath, although extremely low levels of PLP have been found (<1%) in peripheral nervous system (PNS) myelin. The normal serum concentration of PLP is <9 ng/ml (300 pM). Serum PLP is elevated after cerebral infarction, but not after transient ischemic attack (Trotter, J. L. et al., *Ann. Neurol.* 14:554-558, 1983). Current reports investigating serum PLP elevations associated with stroke are severely limited. Elevations of PLP in serum can be attributed to cerebral injury due to physical damage or ischemia caused by infarction or cerebral hemorrhage, coupled with increased permeability of the blood brain barrier. Correlation of the serum concentration of PLP with the extent of damage (infarct volume) or neurological outcome has not been established. No investigations examining the release kinetics of PLP into serum and its subsequent removal have been reported, but maximum concentrations approaching 60 ng/ml (2 nM) have been reported in encephalitis patients, which nearly doubles the concentrations found following stroke. PLP appears to a very specific marker for severe CNS injury, specifically, injury to oligodendrocytes. The available information relating PLP serum elevations and stroke is severely limited. PLP is also elevated in the serum of individuals with various neuropathies affecting the CNS. The undiagnosed presence of these individuals in the larger population of individuals that would be candidates for an assay using this marker for stroke is rare.

S-100 is a 21 kDa homo- or heterodimeric cytosolic $Ca^{2+}$-binding protein produced from α and β subunits. It is thought to participate in the activation of cellular processes along the Ca2+-dependent signal transduction pathway (Bonfrer, J. M. et al, *Br. J. Cancer* 77:2210-2214, 1998). S-100ao (αα isoform) is found in striated muscles, heart and kidney, S-100a (αβ isoform) is found in glial cells, but not in Schwann cells, and S-100b (ββ isoform) is found in high concentrations in glial cells and Schwann cells, where it is a major cytosolic component. The β subunit is specific to the nervous system, predominantly the CNS, under normal physiological conditions and, in fact, accounts for approximately 96% of the total S-100 protein found in the brain (Jensen, R. et al, *J. Neurochem.* 45:700-705, 1985). In addition, S-100β can be found in tumors of neuroendocrine origin, such as gliomas, melanomas, Schwannomas, neurofibromas, and highly differentiated neuroblastomas, like ganglioneuroblastoma and ganglioneuroma (Persson, L. et al., *Stroke* 18:911-918, 1987). The normal serum concentration of S-100β is <0.2 ng/ml (19 pM), which is the detection limit of the immunological detection assays used. Serum S-100β is elevated after all stroke types, including TIAs. Elevations of S-100β, in serum can be attributed to cerebral injury due to physical damage or ischemia caused by infarction or cerebral hemorrhage, coupled with increased permeability of the blood-brain barrier, and the serum concentration of S-100β has been shown to correlate with the extent of damage (infarct volume) and neurological outcome (Martens, P. et al., *Stroke* 29:2363-2366, 1998; Missler, U. et al., *Stroke* 28:1956-1960, 1997). S-100β has a biological half-life of 2 hours and is not normally detected in serum, but is elevated after stroke and cerebral injury. Serum S-100β is elevated after 4 hours from stroke onset, with concentrations reaching a maximum 2-3 days after onset. After the serum concentration reaches its maximum, which can approach 20 ng/ml (1.9 mM), it gradually decreases to normal over approximately one week. Because the severity of damage has a direct effect on the release of S-100β, it will affect the release kinetics by influencing the length of time that S-100β is elevated in the serum. S-100β will be present in the serum for a longer period of time as the severity of injury increases. The release of S-100β into the serum of patients with head injury seems to follow somewhat similar kinetics as reported with stroke, with the only exception being that serum S-100β can be detected within 2.5 hours of onset and the maximum serum concentration is reached approximately 1 day after onset (Woertgen, C. et al., *Acta Neurochir. (Wien)* 139:1161-1164, 1997). S-100β is a specific marker for cerebral injury, specifically, injury to glial cells due to cell death caused by ischemia or physical damage. Glial cells are about 10 times more abundant in the brain than neurons, so any cerebral injury coupled with increased permeability of the blood-brain barrier will likely produce elevations of serum S-100β. Furthermore, elevated serum concentrations of S-100β can indicate complications related to cerebral injury after AMI and cardiac surgery. S-100β has been virtually undetectable in normal individuals, and elevations in its serum concentration correlate with the seventy of damage and the neurological outcome of the individual. S-100β can be used as a marker of all stroke types, including TIAs. However, S-100β cannot be used to differentiate ischemic and hemorrhagic stroke, and it is elevated in the population of individuals having neuroendocrine tumors, usually in advanced stages.

Thrombomodulin (TM) is a 70 kDa single chain integral membrane glycoprotein found on the surface of vascular endothelial cells. TM demonstrates anticoagulant activity by changing the substrate specificity of thrombin. The formation of a 1:1 stoichiometric complex between thrombin and TM changes thrombin function from procoagulant to anticoagulant. This change is facilitated by a change in thrombin substrate specificity that causes thrombin to activate protein C (an inactivator of factor Va and factor VIIIa), but not cleave fibrinogen or activate other coagulation factors (Davie, E. W. et al., *Biochem.* 30:10363-10370, 1991). The normal serum concentration of TM is 25-60 ng/ml (350-850 pM). Current reports describing serum TM concentration alterations following ischemic stroke are mixed, reporting no changes or significant increases (Seki, Y. et al., *Blood Coagul. Fibrinolysis* 8:391-396, 1997). Serum elevations of TM concentration reflect endothelial cell injury and would not indicate coagulation or fibrinolysis activation.

The gamma isoform of protein kinase C (PKCg) is specific for CNS tissue and is not normally found in the circulation. PKCg is activated during cerebral ischemia and is present in the ischemic penumbra at levels 2-24-fold higher than in contralateral tissue, but is not elevated in infarcted tissue (Krupinski, J. et al., *Acta Neurobiol. Exp. (Warz)* 58:13-21, 1998). In addition, animal models have identified increased levels of PKCg in the peripheral circulation of rats following middle cerebral artery occlusion (Cornell-Bell, A. et al., Patent No. WO 01/16599 A1). Additional isoforms of PKC, beta I and beta II were found in increased levels in the infarcted core of brain tissue from patients with cerebral ischemia (Krupinski, J. et al., *Acta Neurobiol. Exp. (Warz)* 58:13-21, 1998). Furthermore, the alpha and delta isoforms of PKC (PKCa and PKCd, respectively) have been implicated in the development of vasospasm following subarachnoid hemorrhage using a canine model of hemorrhage. PKCd expression was significantly elevated in the basilar artery during the early stages of vasospasm, and PKCa was significantly elevated as vasospasm progressed (Nishizawa, S. et al., *Eur. J. Pharmacol.* 398:113-119, 2000). Therefore, it may be of benefit to measure various isoforms of PKC, either individually or in various combinations thereof, for the identification of cerebral damage, the presence of the ischemic penumbra, as well as the development and progression of cerebral vasospasm following subarachnoid hemorrhage. Ratios of PKC isoforms such as PKCg and either PKCbI, PKCbII, or both also may be of benefit in identifying a progressing stroke, where the ischemic penumbra is converted to irreversibly damaged infarcted tissue. In this regard, PKCg may be used to identify the presence and volume of the ischemic penumbra, and either PKCbI, PKCbII, or both may be used to identify the presence and volume of the infarcted core of irreversibly damaged tissue during stroke. PKCd, PKCa, and ratios of PKCd and PKCa may be useful in identifying the presence and progression of cerebral vasospasm following subarachnoid hemorrhage.

(vi) Exemplary Non-specific Markers for Cerebral Injury Related to Coagulation

Plasmin is a 78 kDa serine proteinase that proteolytically digests crosslinked fibrin, resulting in clot dissolution. The 70 kDa serine proteinase inhibitor α2-antiplasmin (α2AP) regulates plasmin activity by forming a covalent 1:1 stoichiometric complex with plasmin. The resulting ~150 kDa plasmin-α2AP complex (PAP), also called plasmin inhibitory complex (PIC) is formed immediately after α2AP comes in contact with plasmin that is activated during fibrinolysis. The normal serum concentration of PAP is <1 μg/ml (6.9 nM). Serum PAP concentration is significantly elevated following embolic and hemorrhagic stroke, but not thrombotic or lacunar stroke, and the magnitude of elevation correlates with the severity of injury and neurological outcome (Seki, Y. et al., *Am. J. Hematol.* 50:155-160, 1995; Yamazaki, M. et al., *Blood Coagul. Fibrinolysis* 4:707-712, 1993; Uchiyama, S. et al., *Semin. Thromb. Hemost.* 23:535-541, 1997; Fujii, Y. et al., *Neurosurgery* 37:226-234, 1995). There are no reports that identify elevations in serum PAP concentration following cerebral transient ischemic attacks. Elevations in the serum concentration of PAP can be attributed to the activation of fibrinolysis. Elevations in the serum concentration of PAP may be associated with clot presence, or any condition that causes or is a result of fibrinolysis activation. These conditions can include atherosclerosis, disseminated intravascular coagulation, AMI, surgery, trauma, unstable angina, and thrombotic thrombocytopenic purpura. PAP is formed immediately following proteolytic activation of plasmin. Serum PAP is increased in embolic and hemorrhagic stroke. Serum concentrations are elevated soon after stroke onset and may persist for over 2 weeks (Fujii, Y. et al., *J. Neurosurg.* 86:594-602, 1997). In addition, serum PAP concentration may be higher in hemorrhagic stroke than in ischemic stroke. This could reflect the increased magnitude of coagulation activation associated with hemorrhage. Serum concentrations of PAP associated with stroke can approach 6 μg/ml (41 nM). PAP is a specific marker for fibrinolysis activation and the presence of a recent or continual hypercoagulable state. It is not specific for stroke or cerebral injury and can be elevated in many other disease states. However, it may be possible to use PAP to differentiate hemorrhagic stroke from ischemic stroke, which would be beneficial in ruling out patients for thrombolytic therapy, and to identify embolic vs. non-embolic ischemic strokes.

β-thromboglobulin (βTG) is a 36 kDa platelet α granule component that is released upon platelet activation. The normal serum concentration of βTG is <40 ng/ml (1.1 nM). Serum βTG concentration is elevated following ischemic and hemorrhagic stroke (Landi, G. et al., *Neurol.* 37:1667-1671, 1987). Serum elevations were not found to correlate with injury severity or neurological- outcome. Investigations regarding βTG serum elevations in stroke are severely limited. Elevations in the serum βTG concentration can be attributed to platelet activation, which could indirectly indicate the presence of vascular injury. Elevations in the serum concentration of βTG may be associated with clot presence, or any condition that causes platelet activation. These conditions can include atherosclerosis, disseminated intravascular coagulation, AMI, surgery, trauma, unstable angina, and thrombotic thrombocytopenic purpura. βTG is released into the circulation immediately after platelet activation and aggregation. It has a biphasic half-life of 10 minutes, followed by an extended 1 hour half-life in serum (Switaiska, H. I. et al., *J. Lab. Clin. Med.* 106:690-700, 1985). Serum βTG concentration is reported to be elevated in various stroke types, but these studies may not be completely reliable. Special precautions must be taken to avoid platelet activation during the blood sampling process. Platelet activation is common during regular blood sampling, and could lead to artificial elevations of serum βTG concentration. In addition, the amount of βTG released into the bloodstream is dependent on the platelet count of the individual, which can be quite variable. Serum concentrations of βTG associated with stroke can approach 70 ng/ml (2 nM). βTG is a specific marker of platelet activation, but it is not specific for stroke or cerebral injury and can be elevated in many other disease states.

Platelet factor 4 (PF4) is a 40 kDa platelet α granule component that is released upon platelet activation. PF4 is a marker of platelet activation and has the ability to bind and neutralize heparin. The normal serum concentration of PF4 is <7 ng/ml (175 pM). Serum PF4 concentration is marginally elevated following intracerebral infarction, but not in individuals with intracerebral hemorrhage (Carter, A. M. et al., *Arterioscler. Thromb. Vasc. Biol.* 18:1124-1131, 1998). Additionally, serum PF4 concentrations are increased 5-9 days following subarachnoid hemorrhage, which may be related to the onset of cerebral vasospasm (Hirashima, Y. et al., *Neurochem. Res.* 22:1249-1255, 1997). Investigations regarding PF4 serum elevations in stroke are severely limited. Elevations in the serum PF4 concentration can be attributed to platelet activation, which could indirectly indicate the presence of vascular injury. Elevations in the serum concentration of PF4 may be associated with clot presence, or any condition that causes platelet activation. These conditions can include atherosclerosis, disseminated intravascular coagulation, AMI, surgery, trauma, unstable angina, and thrombotic thrombocytopenic purpura. PF4 is released into the circulation immediately after platelet activation and aggregation. It has a biphasic half-life of 1 minute, followed by an extended 20 minute half-life in serum. The half-life of PF4 in serum can be extended to 20-40 minutes by the presence of heparin (Rucinski, B. et al., *Am. J. Physiol.* 251:H800-H807, 1986).

Special precautions must be taken to avoid platelet activation during the blood sampling process. Serum concentrations of PF4 associated with stroke can exceed 200 ng/ml (5 nM), but it is likely that this value may be influenced by platelet activation during the sampling procedure. Furthermore, the serum PF4 concentration would be dependent on platelet count, requiring a second variable to be determined along with the concentration estimates. Finally, patients taking aspirin or other platelet activation inhibitors would compromise the clinical usefulness of PF4 as a marker of platelet activation.

Fibrinopeptide A (FPA) is a 16 amino acid, 1.5 kDa peptide that is liberated from amino terminus of fibrinogen by the action of thrombin. Fibrinogen is synthesized and secreted by the liver. The normal serum concentration of FPA is <4 ng/ml (2.7 nM). Serum FPA is elevated after all stroke types, including cerebral transient ischemic attacks (TIAs) (Fon, E. A. et al, *Stroke* 25:282-286, 1994; Tohgi, H. et al., *Stroke* 21:1663-1667, 1990; Landi, G. et al., *Neurol.* 37:1667-1671, 1987). Elevations of FPA in serum can be attributed to coagulation activation, and the serum concentration of FPA has been reported to correlate with the neurological outcome, but not the severity or extent of damage (infarct volume) (Feinberg, W. M. et al., *Stroke* 27:1296-1300, 1996). Elevations in the serum concentration of FPA are associated with any condition that causes or is a result of coagulation activation. These conditions can include AMI, surgery, cancer, disseminated intravascular coagulation, nephrosis, thrombotic thrombocytopenic purpura, and unstable angina. FPA is released into the bloodstream immediately upon clot formation and it can remain elevated for more than 1 month. Maximum serum FPA concentrations following stroke can exceed 50 ng/ml (34 nM).

(vi) Other Non-Specific Markers for cellular Injury

Human vascular endothelial growth factor (VEGF) is a dimeric protein, the reported activities of which include stimulation of endothelial cell growth, angiogenesis, and capillary permeability. VEGF is secreted by a variety of vascularized tissues. In an oxygen-deficient environment, vascular endothelial cells may be damaged and may not ultimately survive. However, such endothelial damage stimulates VEGF production by vascular smooth muscle cells. Vascular endothelial cells may exhibit increased survival in the presence of VEGF, an effect that is believed to be mediated by expression of Bc1-2. VEGF can exist as a variety of splice variants known as VEGF(189), VEGF(165), VEGF(164), VEGFB (155), VEGF(148), VEGF(145), and VEGF(121).

Insulin-like growth factor-1 (IGF-1) is a ubiquitous 7.5 kDa secreted protein that mediates the anabolic and somatogenic effects of growth hormone during development (1, 2). In the circulation, IGF-1 is normally bound to an IGF-binding protein that regulates IGF activity. The normal serum concentration of IGF-1 is approximately 160 ng/ml (21.3 nM). Serum IGF-1 concentrations are reported to be significantly decreased in individuals with ischemic stroke, and the magnitude of reduction appears to correlate with the severity of injury (Schwab, S. et al., *Stroke* 28:1744-1748, 1997). Decreased IGF-1 serum concentrations have been reported in individuals with trauma and massive activation of the immune system. Due to its ubiquitous expression, serum IGF-1 concentrations could also be decreased in cases of non-cerebral ischemia. Interestingly, IGF-1 serum concentrations are decreased following ischemic stroke, even though its cellular expression is upregulated in the infarct zone (Lee, W. H. and Bondy, C., *Ann. N.Y. Acad. Sci.* 679:418-422, 1993). The decrease in serum concentration could reflect an increased demand for growth factors or an increased metabolic clearance rate. Serum levels were significantly decreased 24 hours after stroke onset, and remained decreased for over 10 days (Schwab, S. et al., *Stroke* 28:1744-1748, 1997). Serum IGF-1 may be a sensitive indicator of cerebral injury. However, the ubiquitous expression pattern of IGF-1 indicates that all tissues can potentially affect serum concentrations of IGF-1, compromising the specificity of any assay using IGF-1 as a marker for stroke. In this regard, IGF-1 may be best suited as a cerebrospinal fluid marker of cerebral ischemia, where its dominant source would be neural tissue.

Interleukin-8 (IL-8) is a 6.5 kDa chemokine produced by monocytes, endothelial cells, alveolar macrophages and fibroblasts. IL-8 induces chemotaxis and activation of neutrophils and T cells.

Adhesion molecules are involved in the inflammatory response can also be considered as acute phase reactants, as their expression levels are altered as a result of insult. Examples of such adhesion molecules include E-selectin, intercellular adhesion molecule-1, vascular cell adhesion molecule, and the like.

E-selectin, also called ELAM-1 and CD62E, is a 140 kDa cell surface C-type lectin expressed on endothelial cells in response to IL-1 and TNFα that mediates the "rolling" interaction of neutrophils with endothelial cells during neutrophil recruitment. The normal serum concentration of E-selectin is approximately 50 ng/ml (2.9 nM). Investigations into the changes on serum E-selectin concentrations following stroke have reported mixed results. Some investigations report increases in serum E-selectin concentration following ischemic stroke, while others find it unchanged (Bitsch, A. et al., *Stroke* 29:2129-2135, 1998; Kim, J. S., *J. Neurol. Sci.* 137:69-78, 1996; Shyu, K. G. et al., *J. Neurol.* 244:90-93, 1997). E-selectin concentrations are elevated in the CSF of individuals with subarachnoid hemorrhage and may predict vasospasm (Polin, R. S. et al., *J. Neurosurg.* 89:559-567, 1998). Elevations in the serum concentration of E-selectin would indicate immune system activation. Serum E-selectin concentrations are elevated in individuals with, atherosclerosis, various forms of cancer, preeclampsia, diabetes, cystic fibrosis, AMI, and other nonspecific inflammatory states (Hwang, S. J. et al., *Circulation* 96:4219-4225, 1997; Banks, R. E. et al., *Br. J. Cancer* 68:122-124, 1993; Austgulen, R. et al., *Eur. J. Obstet. Gynecol. Reprod. Biol.* 71:53-58, 1997; Steiner, M. et al., *Thromb. Haemost.* 72:979-984, 1994; De Rose, V. et al., *Am. J. Respir. Crit. Care Med.* 157:1234-1239, 1998). The serum concentration of E-selectin maybe elevated following ischemic stroke, but it is not clear if these changes are transient or regulated by an as yet unidentified mechanism. Serum E-selectin may be a specific marker of endothelial cell injury. It is not, however, a specific marker for stroke or cerebral injury, since it is elevated in the serum of individuals with various conditions causing the generation of an inflammatory state. Furthermore, elevation of serum E-selectin concentration is associated with some of the risk factors associated with stroke.

Matrix metalloproteinase-3 (MMP-3), also called stromelysin-1, is a 45 kDa zinc- and calcium-binding proteinase that is synthesized as an inactive 60 kDa precursor. Mature MMP-3 cleaves proteoglycan, fibrinectin, laminin, and type IV collagen, but not type I collagen. MMP-3 is synthesized by a variety of cells, including smooth muscle cells, mast cells, macrophage-derived foam cells, T lymphocytes, and endothelial cells (Johnson, J. L., et al., *Arterioscler. Thromb. Vasc. Biol.* 18:1707-1715, 1998). MMP-3, like other MMPs, is involved in extracellular matrix remodeling, which can occur following injury or during intervascular cell migration. MMP-3 is normally found at a concentration of <125 ng/ml in plasma (Zucker, S. et al., *J. Rheumatol*. 26:78-80, 1999). The serum MMP-3 concentration also has been shown to increase with age, and the concentration in males is approximately 2 times higher in males than in females (Manicourt, D. H. et al., *Arthritis Rheum*. 37:1774-1783, 1994). MMP-3 is found in the shoulder region of atherosclerotic plaques, which is the region most prone to rupture, and may be involved in atherosclerotic plaque destabilization (Johnson, J. L. et al., *Arterioscler. Thromb. Vasc. Biol*. 18:1707-1715, 1998). Therefore, the circulating MMP-3 concentration may be elevated as a result of atherosclerotic plaque rupture. Serum MMP-3 also may be elevated inflammatory conditions that induce mast cell degranulation. Serum MMP-3 concentrations are elevated in patients with arthritis and systemic lupus erythematosus (Zucker, S. et al., *J. Rheumatol*. 26:78-80, 1999; Keyszer, G. et al., *J. Rheumatol*. 57:392-398, 1998; Keyszer, G. et al., *J. Rheumatol*. 26:251-258, 1999). Serum MMP-3 also is elevated in patients with prostate and urothelial cancer, and also glomerulonephritis (Lein, M. et al., *Urologe A* 37:377-381, 1998; Gohji, K. et al., *Cancer* 78:2379-2387, 1996; Akiyama, K. et al., *Res. Commun. Mol. Pathol. Pharmacol*. 95:115-128, 1997). The serum concentration of MMP-3 may also be elevated in patients with other types of cancer. Serum MMP-3 is decreased in patients with hemochromatosis (George, D. K. et al., *Gut* 42:715-720, 1998). MMP-3 is released during mast cell degranulation, and is presumably released during atherosclerotic plaque rupture. In this regard, MMP-3 may be useful as a marker of stroke associated with plaque rupture.

Matrix metalloproteinase 9 (MMP-9) is a secreted 92 kDa serine proteinase produced by neutrophils and various tissues, whose substrates include components of the extracellular matrix. MMPs are synthesized as inactive zymogens that are proteolytically cleaved to produce active MMPs. They have the ability to bind divalent cations, most commonly $Zn^{2+}$, and this binding is essential for proteinase activity. Cancer cells sometimes produce MMPs to facilitate extracellular matrix degradation during invasion and metastasis. MMP is normally found in brain, and its expression is induced by various cytokines (Mun-Bryce, S. and Rosenberg, G A., *J. Cereb. Blood Flow Metab*. 18:1163-1172, 1998). The normal serum concentration of MMP-9 is <35 ng/ml (380 pM). Serum MMP-9 concentration is marginally elevated following cerebral ischemia in a rat model, but no human studies have been reported (Romanic, A. M. et al., *Stroke* 29:1020-1030, 1998). MMP-9 gene expression is maximally elevated 16-24 hours following cerebral hemorrhage or intracerebral injection of proinflammatory cytokines in rats (Rosenberg, G. A., *J. Neurotrauma* 12:833-842, 1995). Furthermore, MMP-9 may be partially responsible for the development of delayed neurological deficits, particularly hemorrhagic transformation of ischemic stroke and vasospasm following hemorrhagic stroke. In this regard, elevation of the serum MMP-9 concentration may indicate the potential for occurrence of delayed neurological deficit. Elevations in the serum concentration of MMP-9 may be associated with various carcinomas and giant cell arteritis (Blankaert, D. et al., *J. Acquir. Immune Defic. Syndr. Hum. Retrovirol*. 18:203-209, 1998; Endo, K. et al., *Anticancer Res*. 17:2253-2258, 1997; Hayasaka, A. et al., *Hepatology* 24:1058-1062, 1996; Moore, D. H. et al., *Gynecol. Oncol*. 65:78-82, 1997; Sorbi; D. et al., *Arthritis Rheum*. 39:1747-1753, 1996). MMP-9 is produced and released into the circulation following various stroke types, but these studies have not been performed using human samples. Serum concentrations of MMP-9 have been demonstrated to exceed 600 ng/ml (6.5 nM) in humans. MMP-9 is a specific marker of extracellular matrix degradation, but it is not specific for stroke or cerebral injury and can be elevated in other disease states such as cancer. However, the measurement of increased serum MMP-9 concentration may indicate that the individual is at high risk for the development of hemorrhagic transformation following ischemic stroke or vasospasm following hemorrhagic stroke. This determination is based on the hypothesis that MMP-9 is a pathogenic mediator of these delayed neurological deficits.

Head activator (HA) is an 11 amino acid, 1.1 kDa neuropeptide that is found in the hypothalamus and intestine. It was originally found in the freshwater coelenterate hydra, where it acts as a head-specific growth and differentiation factor. In humans, it is thought to be a growth regulating agent during brain development. The normal serum HA concentration is <0.1 ng/ml (100 pM) Serum HA concentration is persistently elevated in individuals with tumors of neural or neuroendocrine origin (Schaller, H. C. et al., *J Neurooncol*. 6:251-258, 1988; Winnikes, M. et al., *Eur. J. Cancer* 28:421-424, 1992). No studies have been reported regarding HA serum elevations associated with stroke. HA is presumed to be continually secreted by tumors of neural or neuroendocrine origin, and serum concentration returns to normal following tumor removal. Serum HA concentration can exceed 6.8 ng/ml (6.8 nM) in individuals with neuroendocrine-derived tumors. The usefulness of HA as part of a stroke panel would be to identify individuals with tumors of neural or neuroendocrine origin. These individuals may have serum elevations of markers associated with cerebral injury as a result of cancer, not cerebral injury related to stroke. Although these individuals may be a small subset of the group of individuals that would benefit from a rapid diagnostic of cerebral injury, the use of HA as a marker would aid in their identification. Finally, angiotensin converting enzyme, a serum enzyme, has the ability to degrade HA, and blood samples would have to be drawn using EDTA as an anticoagulant to inhibit this activity.

C-type natriuretic peptide (CNP) a 22-amino acid peptide that is the primary active natriuretic peptide in the human brain; CNP is also considered to be an endothelium-derived relaxant factor, which acts in the same way as nitric oxide (NO) (Davidson et al., *Circulation* 93:1155-9, 1996). CNP is structurally related to Atrial natriuretic peptide (ANP) and B-type natriuretic peptide (BNP); however, while ANP and BNP are synthesized predominantly in the myocardium, CNP is synthesized in the vascular endothelium as a precursor (pro-CNP) (Prickett et al., *Biochem. Biophys. Res. Commun*. 286:513-7, 2001). CNP is thought to possess vasodilator effects on both arteries and veins and has been reported to act mainly on the vein by increasing the intracellular cGMP concentration in vascular smooth muscle cells .

Adrenomedullin (AM) is a 52-amino acid peptide which is produced in many tissues, including adrenal medulla, lung, kidney and heart (Yoshitomi et al., *Clin. Sci*. (*Colch*) 94:135-9, 1998). Intravenous administration of AM causes a long-lasting hypotensive effect, accompanied with an increase in the cardiac output in experimental animals. AM has been reported to enhance the stretch-induced release of ANP from the right atrium, but not to affect ventricular BNP expression. AM is synthesized as a precursor molecule (pro-AM). The N-terminal peptide processed from the AM precursor has also been reported to act as a hypotensive peptide (Kuwasako et al., *Ann. Clin. Biochem*. 36:622-8, 1999).

The endothelins are three related peptides (endothelin-1, endothelin-2, and endothelin-3) encoded by separate genes that are produced by vascular endothelium, each of which exhibit potent vasoconstricting activity. Endothelin-1 (ET-1) is a 21 amino acid residue peptide, synthesized as a 212 residue precursor (preproET-1), which contains a 17 residue signal sequence that is removed to provide a peptide known as big ET-1. This molecule is further processed by hydrolysis between trp21 and val22 by endothelin converting enzyme. Both big ET-1 and ET-1 exhibit biological activity; however the mature ET-1 form exhibits greater vasoconstricting activity (Brooks and Ergul, *J. Mol. Endocrinol.* 21:307-15, 1998). Similarly, endothelin-2 and endothelin-3 are also 21 amino acid residues in length, and are produced by hydrolysis of big endothelin-2 and big endothelin-3, respectively (Yap et al, *Br. J. Pharmacol.* 129:170-6, 2000; Lee et al., *Blood* 94:1440-50, 1999).

Urotensin 2 is a peptide having the sequence Ala-Gly-Thr-Ala-Asp-Cys-Phe-Trp-Lys-Tyr-Cys-Val, with a disulfide bridge between Cys6 and Cys 11. Human urotensin 2 (UTN) is synthesized in a prepro form. Processed urotensin 2 has potent vasoactive and cardiostimulatory effects, acting on the G protein-linked receptor GPR14.

Vasopressin (arginine vasopressin, AVP; antidiuretic hormone, ADH) is a peptide hormone released from the posterior pituitary. Its primary function in the body is to regulate extracellular fluid volume by affecting renal handling of water. There are several mechanisms regulating release of AVP. Hypovolemia, as occurs during hemorrhage, results in a decrease in atrial pressure. Specialized stretch receptors within the atrial walls and large veins (cardiopulmonary baroreceptors) entering the atria decrease their firing rate when there is a fall in atrial pressure. Afferent from these receptors synapse within the hypothalamus; atrial receptor firing normally inhibits the release of AVP by the posterior pituitary. With hypovolemia or decreased central venous pressure, the decreased firing of atrial stretch receptors leads to an increase in AVP release. Hypothalamic osmoreceptors sense extracellular osmolarity and stimulate AVP release when osmolarity rises, as occurs with dehydration. Finally, angiotensin II receptors located in a region of the hypothalamus regulate AVP release—an increase in angiotensin II simulates AVP release.

Heart Failure is also associated with what might be viewed as a paradoxical increase in AVP. Increased blood volume and atrial pressure associated with heart failure suggest that AVP secretion might be inhibited, but is not. It may be that sympathetic and renin-angiotensin system activation in heart failure override the volume and low pressure cardiovascular receptors (as well as the osmoregulation of AVP) and cause an increase in AVP secretion. Nevertheless, this increase in AVP during heart failure may contribute to the increase in systemic vascular resistance as well as enhance renal retention of fluid.

AVP has two principle sites of action: kidney and blood vessels. The most important physiological action of AVP is that it increases water reabsorption by the kidneys by increasing water permeability in the collecting duct, thereby permitting the formation of a more concentrated urine. This is the antidiuretic effect of AVP. This hormone also constricts arterial blood vessels; however, the normal physiological concentrations of AVP are below its vasoactive range.

Calcitonin gene related peptide (CGRP) is a polypeptide of 37 amino acids that is a product of the calcitonin gene derived by alternative splicing of the precursor mRNA. The calcitonin gene (CALC-I) primary RNA transcript is processed into different mRNA segments by inclusion or exclusion of different exons as part of the primary transcript. Calcitonin-encoding mRNA is the main product of CALC-I transcription in C-cells of the thyroid, whereas CGRP-I mRNA (CGRP=calcitonin-gene-related peptide) is produced in nervous tissue of the central and peripheral nervous systems (FIG. 2.2.1) (9). In the third mRNA sequence, the calcitonin sequence is lost and alternatively the sequence of CGRP is encoded in the mRNA. CGRP is a markedly vasoactive peptide with vasodilatative properties. CGRP has no effect on calcium and phosphate metabolism and is synthesised predominantly in nerve cells related to smooth muscle cells of the blood vessels (149). ProCGRP, the precursor of CGRP, and PCT have partly identical N-terminal amino acid sequences.

Angiotensin II is an octapeptide hormone formed by renin action upon a circulating substrate, angiotensinogen, that undergoes proteolytic cleavage to from the decapeptide angiotensin I. Vascular endothelium, particularly in the lungs, has an enzyme, angiotensin converting enzyme (ACE), that cleaves off two amino acids to form the octapeptide, angiotensin II (AII).

AII has several very important functions: Constricts resistance vessels (via AII receptors) thereby increasing systemic vascular resistance and arterial pressure; Acts upon the adrenal cortex to release aldosterone, which in turn acts upon the kidneys to increase sodium and fluid retention; Stimulates the release of vasopressin (antidiuretic hormone, ADH) from the posterior pituitary which acts upon the kidneys to increase fluid retention; Stimulates thirst centers within the brain; Facilitates norepinephrine release from sympathetic nerve endings and inhibits norepinephrine re-uptake by nerve endings, thereby enhancing sympathetic adrenergic function; and Stimulates cardiac hypertrophy and vascular hypertrophy.

Glycated hemoglobin HbAlc measurement provides an assessment of the degree to which blood glucose has been elevated over an extended time period, and so has been related to the extent diabetes is controlled in a patient. Glucose binds slowly to hemoglobin A, forming the Alc subtype. The reverse reaction, or decomposition, proceeds relatively slowly, so any buildup persists for roughly 4 weeks. With normal blood glucose levels, glycated hemoglobin is expected to be 4.5% to 6.7%. As blood glucose concentration rise, however, more binding occurs. Poor blood sugar control over time is suggested when the glycated hemoglobin measure exceeds 8.0%.

Other Preferred Markers

The following table provides a list of additional preferred markers, associated with a disease or condition for which each marker can provide useful information for differential diagnosis. Various markers may be listed for more than one condition. As understood by the skilled artisan and described herein, markers may indicate different conditions when considered with additional markers in a panel; alternatively, markers may indicate different conditions when considered in the entire clinical context of the patient.

| Condition | Marker |
| --- | --- |
| Acute Coronary Syndrome | Haptoglobin |
| Acute Coronary Syndrome | S100a |
| Acute Coronary Syndrome | s-CD40 ligand |
| Acute Coronary Syndrome | S-FAS ligand |
| Aortic dissection | alpha 2 actin |
| Aortic dissection | basic calponin 1 |
| Aortic dissection | beta like 1 integrin |
| Aortic dissection | CSRP2 |
| Aortic dissection | elastin |
| Aortic dissection | LTBP4 |
| Aortic dissection | smooth muscle myosin |
| Aortic dissection | transgelin |
| Aortic dissection | MMP1 |
| Aortic dissection | MMP2 |

-continued

| Condition | Marker |
|---|---|
| Aortic dissection | MMP3 |
| Diastolic dysfunction | aldosterone |
| Diastolic dysfunction | angiotensin 1 |
| Diastolic dysfunction | angiotensin 2 |
| Diastolic dysfunction | angiotensin 3 |
| Diastolic dysfunction | Bradykinin |
| Diastolic dysfunction | calcitonin |
| Diastolic dysfunction | calcitonin gene related peptide |
| Diastolic dysfunction | Endothelin-2 |
| Diastolic dysfunction | Endothelin-3 |
| Diastolic dysfunction | Renin |
| diastolic dysfunction/sepsis | Vasopressin |
| pancreatitis | APO B48 |
| pancreatitis | pancreatic elastase 1 |
| pancreatitis | pancreatic Lipase |
| pancreatitis | sPLA2 |
| pancreatitis | Trypsinogen activation peptide |
| pulmonary embolism | alpha enolase |
| pulmonary embolism | LAMP3 |
| pulmonary embolism | phospholipase D |
| pulmonary embolism | PLA2G5 |
| pulmonary embolism | Protein D |
| pulmonary embolism | SFTPC |
| pulmonary embolism | Defensin HBD 1 |
| pulmonary embolism | Defensin HBD 2 |
| pulmonary embolism | CXC-type chemokines (CXCL-1, CXCL-2, CXCL-3) |
| pulmonary embolism | CC-type chemokines (CCL2, CCL3, CCL4, CCL8) |
| pulmonary embolism | Endothelin 1 |
| sepsis | Defensin HBD 1 |
| sepsis | Defensin HBD 2 |
| sepsis | D-dimer |
| sepsis | iL-1 |
| sepsis | iL-10* |
| sepsis | iL-11* |
| sepsis | iL-13* |
| sepsis | iL-18* |
| sepsis | iL-4* |
| sepsis | Procalcitonin |
| sepsis | PROTEIN C |
| sepsis | Serum Amyloid A |
| sepsis | s-Glutathione |
| sepsis | s-iL 18 receptor |
| sepsis | S-iL-1 receptor |
| sepsis | s-TNF P55 |
| sepsis | s-TNF P75 |
| sepsis | TAFI |
| sepsis | TGF-beta |
| sepsis | MMP-11 |
| stroke | Brain Fatty acid binding protein |
| stroke | CA11 |
| stroke | CABP1 |
| stroke | CACNA1A |
| stroke | CBLN1 |
| stroke | CHN1 |
| stroke | CHN2 |
| stroke | cleaved Tau |
| stroke | CRHR1 |
| stroke | DRPLA |
| stroke | EGF |
| stroke | Endothelin-1 |
| stroke | GFAP |
| stroke | GPM6B |
| stroke | GPR7 |
| stroke | GPR8 |
| stroke | GRIN2C |
| stroke | GRM7 |
| stroke | HAPIP |
| stroke | HIF 1 ALPHA |
| stroke | HIP2 |
| stroke | KCNK4 |
| stroke | KCNK9 |
| stroke | KCNQ5 |
| stroke | MAPK10 |
| stroke | n-acetyl aspartate |
| stroke | NEUROD2 |

-continued

| Condition | Marker |
|---|---|
| stroke | NRG2 |
| stroke | PACE4 |
| stroke | phosphoglycerate mutase |
| stroke | PKC gamma |
| stroke | Prostaglandin E2 |
| stroke | PTEN |
| stroke | PTPRZ1 |
| stroke | RGS9 |
| stroke | SCA7 |
| stroke | secretagogin |
| stroke | SLC1A3 |
| stroke | SORL1 |
| stroke | SREB3 |
| stroke | STAC |
| stroke | STX1A |
| stroke | STXBP1 |
| stroke/migraine | BDNF* |
| stroke/migraine | CGRP |
| stroke/migraine | cystatin C |
| stroke/migraine | neurokinin A |
| stroke/migraine | substance P |

Exemplary Marker Panels for Distinguishing Systolic and Diastolic Heart Failure

Exemplary marker panels related to differentiating systolic and diastolic function comprise one or more markers selected from the group consisting of BNP, BNP related peptides, aldosterone, ANP and ANP related peptides, angiotensin 1, angiotensin 2, angiotensin 3, bradykinin, calcitonin, calcitonin gene related peptide, endothelin-2, endothelin-3, renin, urotensin 2 and vasopressin. Markers related to both systolic and diastolic dysfunction include BNP, ANP and ANP related markers. A preferred list of markers for differentiating systolic and diastolic heart failure include one or more markers selected from the group consisting of BNP, BNP related peptides, calcitonin gene related peptide, urotensin 2, endothelin 2, calcitonin and angiotensin 2. A particularly preferred list of markers for differentiating systolic and diastolic dysfunction include one or more markers selected from the group consisting of BNP, angiotensin 2, urotensin 2, and calcitonin gene related peptide.

Congestive heart failure is a heterogenous condition arising from two primary pathologies: left ventricular diastolic dysfunction and systolic dysfunction, which occur either alone or in combination. Gaasch, *JAMA* 271: 1276-80 (1994). As many as 40 percent of patients with clinical heart failure have diastolic dysfunction with normal systolic function. Soufer et al., *Am. J. Cardiol.* 55: 1032-6 (1984). Patient care decisions and prognosis hinge upon determination of the presence of one or both of these pathologies. Shamsharn and Mitchell, *Am. Fam. Physician* 2000; 61:1319-28 (2000).

Recently, BNP has been reported as a useful marker in the diagnosis of congestive heart failure. Dao et al., *J. Am. Coll. Cardiol.* 37: 379-85 (2001). However, BNP levels alone are not able to distinguish diastolic dysfunction from systolic dysfunction. Krishnaswamy et al., *Am. J. Med.* 111: 274-79 (2001).

Exemplary Marker Panels for Distinguishing Aortic Dissection, Myocardial Ischemia, and Myocardial Infarction Exemplary marker panels related to differentiating aortic dissection, myocardial ischemia, and myocardial infarction comprise one or more markers selected from the group consisting of smooth muscle myosin and/or smooth muscle myosin heavy chain (both aortic dissection markers), BNP and/or BNP related peptides, one or more troponin forms (myocardial ischemia and infarction), and myoglobin (myocardial infarction or necrosis).

Exemplary Marker Panels for Distinguishing Atrial Fibrillation, Myocardial Infarction, and/or Congestive Heart Failure Exemplary marker panels related to differentiating atrial fibrillation, myocardial infarction, and/or congestive heart failure comprise markers selected from the group consisting of ANP, ANP related peptides (atrial fibrillation), one or more troponin forms, myoglobin, BNP, and BNP related peptides.

Assay Measurement Strategies

Numerous methods and devices are well known to the skilled artisan for the detection and analysis of the markers of the instant invention. With regard to polypeptide s or proteins in patient test samples, immunoassay devices and methods are often used. See, e.g., U.S. Pat. Nos. 6,143,576; 6,113,855; 6,019,944; 5,985,579; 5,947,124; 5,939,272; 5,922,615; 5,885,527; 5,851,776; 5,824,799; 5,679,526; 5,525,524; and 5,480,792, each of which is hereby incorporated by reference in its entirety, including all tables, figures and claims. These devices and methods can utilize labeled molecules in various sandwich, competitive, or non-competitive assay formats, to generate a signal that is related to the presence or amount of an analyte of interest. Additionally, certain methods and devices, such as biosensors and optical immunoassays, may be employed to determine the presence or amount of analytes without the need for a labeled molecule. See, e.g., U.S. Pat. Nos. 5,631,171; and 5,955,377, each of which is hereby incorporated by reference in its entirety, including all tables, figures and claims. One skilled in the art also recognizes that robotic instrumentation including but not limited to Beckman Access, Abbott AxSym, Roche ElecSys, Dade Behring Stratus systems are among the immunoassay analyzers that are capable of performing the immunoassays taught herein.

Preferably the markers are analyzed using an immunoassay, although other methods are well known to those skilled in the art (for example, the measurement of marker RNA levels). The presence or amount of a marker is generally determined using antibodies specific for each marker and detecting specific binding. Any suitable immunoassay may be utilized, for example, enzyme-linked immunoassays (ELISA), radioimmunoassays (RIAs), competitive binding assays, and the like. Specific immunological binding of the antibody to the marker can be detected directly or indirectly. Direct labels include fluorescent or luminescent tags, metals, dyes, radionuclides, and the like, attached to the antibody. Indirect labels include various enzymes well known in the art, such as alkaline phosphatase, horseradish peroxidase and the like.

The use of immobilized antibodies specific for the markers is also contemplated by the present invention. The antibodies could be immobilized onto a variety of solid supports, such as magnetic or chromatographic matrix particles, the surface of an assay place (such as microtiter wells), pieces of a solid substrate material or membrane (such as plastic, nylon, paper), and the like. An assay strip could be prepared by coating the antibody or a plurality of antibodies in an array on solid support. This strip could then be dipped into the test sample and then processed quickly through washes and detection steps to generate a measurable signal, such as a colored spot.

The analysis of a plurality of markers may be carried out separately or simultaneously with one test sample. For separate or sequential assay of markers, suitable apparatuses include clinical laboratory analyzers such as the ElecSys (Roche), the AxSym (Abbott), the Access (Beckman), the ADVIA® CENTAUR® (Bayer) immunoassay systems, the NICHOLS ADVANTAGE® (Nichols Institute) immunoassay system, etc. Preferred apparatuses or protein chips perform simultaneous assays of a plurality of markers on a single surface. Particularly useful physical formats comprise surfaces having a plurality of discrete, adressable locations for the detection of a plurality of different analytes. Such formats include protein microarrays, or "protein chips" (see, e.g., Ng and Ilag, *J. Cell Mol. Med*. 6: 329-340 (2002)) and certain capillary devices (see, e.g., U.S. Pat. No. 6,019,944). In these embodiments, each discrete surface location may comprise antibodies to immobilize one or more analyte(s) (e.g., a marker) for detection at each location. Surfaces may alternatively comprise one or more discrete particles (e.g., microparticles or nanoparticles) immobilized at discrete locations of a surface, where the microparticles comprise antibodies to immobilize one analyte (e.g., a marker) for detection.

Several markers may be combined into one test for efficient processing of a multiple of samples. In addition, one skilled in the art would recognize the value of testing multiple samples (for example, at successive time points) from the same individual. Such testing of serial samples will allow the identification of changes in marker levels over time. Increases or decreases in marker levels, as well as the absence of change in marker levels, would provide useful information about the disease status that includes, but is not limited to identifying the approximate time from onset of the event, the presence and amount of salvagable tissue, the appropriateness of drug therapies, the effectiveness of various therapies as indicated by reperfusion or resolution of symptoms, differentiation of the various types of ACS, identification of the severity of the event, identification of the disease severity, and identification of the patient's outcome, including risk of future events.

A panel consisting of the markers referenced above may be constructed to provide relevant information related to differential diagnosis. Such a panel may be constucted using 1, 2, 3, 4, 5, 6, 7, 8, 9, 10, 15, 20, or more or individual markers. The analysis of a single marker or subsets of markers comprising a larger panel of markers could be carried out by one skilled in the art to optimize clinical sensitivity or specificity in various clinical settings. These include, but are not limited to ambulatory, urgent care, critical care, intensive care, monitoring unit, inpatient, outpatient, physician office, medical clinic, and health screening settings. Furthermore, one skilled in the art can use a single marker or a subset of markers comprising a larger panel of markers in combination with an adjustment of the diagnostic threshold in each of the aforementioned settings to optimize clinical sensitivity and specificity. The clinical sensitivity of an assay is defined as the percentage of those with the disease that the assay correctly predicts, and the specificity of an assay is defined as the percentage of those without the disease that the assay correctly predicts (Tietz Textbook of Clinical Chemistry, $2^{nd}$ edition, Carl Burtis and Edward Ashwood eds., W. B. Saunders and Company, p. 496).

The analysis of markers could be carried out in a variety of physical formats as well. For example, the use of microtiter plates or automation could be used to facilitate the processing of large numbers of test samples. Alternatively, single sample formats could be developed to facilitate immediate treatment and diagnosis in a timely fashion, for example, in ambulatory transport or emergency room settings.

In another embodiment, the present invention provides a kit for the analysis of markers. Such a kit preferably comprises devises and reagents for the analysis of at least one test sample and instructions for performing the assay. Optionally the kits may contain one or more means for using information obtained from immunoassays performed for a marker panel to rule in or out certain diagnoses.

Selecting a Treatment Regimen

Just as the potential causes of any particular nonspecific symptom may be a large and diverse set of conditions, the appropriate treatments for these potential causes may be equally large and diverse. However, once a diagnosis is obtained, the clinician can readily select a treatment regimen that is compatible with the diagnosis. Taking just some of the causes of dyspnea for example, initial treatment for pulmonary embolism is supportive, involving analgesics, oxygen, and potentially β-adrenergic stimulation. Thrombolytic therapy or embolectomy may be indicated. In contrast, treatment for systolic dysfunction in congestive heart failure can include therapeutic amounts of ACE inhibitors, digoxin, β-blockers, and diuretics. In particularly serious chronic heart failure, heart transplant may be indicated. The skilled artisan is aware of appropriate treatments for numerous diseases discussed in relation to the methods of diagnosis described herein. See, e.g., *Merck Manual of Diagnosis and Therapy*, 17th Ed. Merck Research Laboratories, Whitehouse Station, N.J., 1999.

EXAMPLES

The following examples serve to illustrate the present invention. These examples are in no way intended to limit the scope of the invention.

Example 1

Blood Sampling

Blood specimens were collected by trained study personnel using EDTA as the anticoagulant and centrifuged for greater than or equal to 10 minutes. The plasma component was transferred into a sterile cryovial and frozen at −20° C. or colder. Specimens from the following population of patients and normal healthy donors were collected (Table 1). Clinical histories were available for each of the patients to aid in the statistical analysis of the assay data.

Example 2

Biochemical Analyses

Markers were measured using standard immunoassay techniques. These techniques involved the use of antibodies to specifically bind the protein targets. A monoclonal antibody directed against a selected marker was biotinylated using N-hydroxysuccinimide biotin (NHS-biotin) at a ratio of about 5 NHS-biotin moieties per antibody. The antibody-biotin conjugate was then added to wells of a standard avidin 384 well microtiter plate, and antibody conjugate not bound to the plate was removed. This formed the "anti-marker" in the microtiter plate. Another monoclonal antibody directed against the same marker was conjugated to alkaline phosphatase using succinimidyl 4-[N-maleimidomethyl]-cyclohexane-1-carboxylate (SMCC) and N-succinimidyl 3-[2-pyridyldithio]propionate (SPDP) (Pierce, Rockford, Ill.).

Immunoassays were performed on a TECAN Genesis RSP 200/8 Workstation. Biotinylated antibodies were pipetted into microtiter plate wells previously coated with avidin and incubated for 60 min. The solution containing unbound antibody was removed, and the wells were washed with a wash buffer, consisting of 20 mM borate (pH 7.42) containing 150 mM NaCl, 0.1% sodium azide, and 0.02% Tween-20. The plasma samples (10 μL) were pipeted into the microtiter plate wells, and incubated for 60 min. The sample was then removed and the wells were washed with a wash buffer. The antibody alkaline phosphatase conjugate was then added to the wells and incubated for an additional 60 min, after which time, the antibody conjugate was removed and the wells were washed with a wash buffer. A substrate, (AttoPhos®, Promega, Madison, Wis.) was added to the wells, and the rate of formation of the fluorescent product was related to the concentration of the marker in the patient samples.

Example 3

Dyspnea Analysis

The following table compares levels of pulmonary surfactant protein D, D-dimer, BNP, total cardiac troponin I, and the ratio of BNP: D-dimer in individual patients presenting with clinical dyspnea and in normal subjects. Dyspnea patients were subdivided into patients receiving a clinical diagnosis of congestive heart failure, and those receiving a clinical diagnosis of pulmonary embolism. All units are ng/ml except BNP (pg/ml) and ratios.

TABLE 1

Multi-Center CHF Patients

| Patient ID | PSD | D-Dimer | BNP | TnI | Ratio |
|---|---|---|---|---|---|
| 16 | 35.4 | 88 | 889 | 2.1 | 10.1 |
| 012 | 8.7 | 113 | 1228 | 2.2 | 10.9 |
| Moore 003 | 6.9 | 62 | 552 | 0.0 | 8.9 |
| 11 | 11.7 | 160 | 987 | 0.5 | 6.2 |
| 010 | 13.3 | 145 | 466 | 0.0 | 3.2 |
| 18 | 7.9 | 39 | 330 | 0.0 | 8.6 |
| 131-2 | 7.2 | 125 | 1031 | 0.0 | 8.3 |
| 125-1 | 3.7 | 49 | 314 | 0.0 | 6.4 |
| 115 | 8.1 | 203 | 185 | 0.0 | 0.9 |
| 128-1 | 7.5 | 141 | 228 | 0.0 | 1.6 |
| 143-1 | 5.1 | 169 | 402 | 0.0 | 2.4 |
| 134-1 | 1.9 | 142 | 251 | 0.0 | 1.8 |
| 138-1 | 2.4 | 40 | 521 | 0.0 | 13.0 |
| 157-1 | 4.1 | 107 | 231 | 0.0 | 2.2 |
| 176-1 | 2.6 | 70 | 234 | 0.0 | 3.4 |
| 175-1 | 4.6 | 154 | 498 | 0.0 | 3.2 |
| 22 | 6.7 | 36 | 650 | 0.0 | 18.3 |
| 21 | 3.9 | 149 | 453 | 0.0 | 3.0 |
| 23 | 11.5 | 147 | 1024 | 0.0 | 7.0 |
| 103-2 | 3.3 | 70 | 640 | 0.0 | 9.2 |
| 20 | 2.9 | 78 | 858 | 0.0 | 11.0 |
| 148-2 | 6.2 | 79 | 1614 | 0.0 | 20.4 |
| 173-2 | 2.7 | 68 | 236 | 0.0 | 3.5 |
| 166-1 | 5.5 | 53 | 681 | 0.0 | 12.9 |
| 178-1 | 4.3 | 89 | 250 | 0.0 | 2.8 |
| 183-2 | 9.3 | 109 | 1199 | 0.0 | 11.0 |
| 189-2 | 2.2 | 270 | 335 | 0.0 | 1.2 |
| 42 | 3.5 | 143 | 846 | 0.0 | 5.9 |
| 43 | 4.2 | 63 | 287 | 0.0 | 4.5 |
| 54 | 3.5 | 51 | 302 | 0.0 | 5.9 |
| 25 | 4.6 | 61 | 768 | 0.0 | 12.5 |
| 53 | 4.5 | 77 | 1813 | 0.0 | 23.5 |
| 59 | 20.8 | 77 | 288 | 0.0 | 3.7 |
| 55 | 2.4 | 53 | 237 | 0.0 | 4.5 |
| 158-1 | 2.3 | 53 | 1030 | 0.0 | 19.6 |
| Mean | 6.7 | 100.9 | 624.5 | 0.1 | 7.8 |
| Median | 4.6 | 79.3 | 498.0 | 0.0 | 6.2 |
| St. Dev. | 6.3 | 53.1 | 415.8 | 0.5 | 5.9 |

TABLE 2

Multi-Center Patients with PE

| Patient ID | PSD | D-Dimer | BNP | TnI | Ratio |
|---|---|---|---|---|---|
| 81 | 4.9 | 145 | 314.7 | 0.0 | 2.2 |
| 110 | 4.3 | 87 | 24.3 | 0.0 | 0.3 |
| 112 | 6.9 | 105 | 15.9 | 0.0 | 0.2 |

TABLE 2-continued

Multi-Center Patients with PE

| Patient ID | PSD | D-Dimer | BNP | TnI | Ratio |
|---|---|---|---|---|---|
| 119 | 10.1 | 104 | 175.7 | 0.0 | 1.7 |
| 142 | 7.0 | 106 | 6.2 | 0.0 | 0.1 |
| 196 | 8.2 | 127 | 5.0 | 0.1 | 0.0 |
| 801-2 | 5.2 | 113 | 19.7 | 0.0 | 0.2 |
| 377-2 | 1.4 | 97 | 57.2 | 0.0 | 0.6 |
| 008264 | 1.3 | 258 | 121.3 | 0.0 | 0.5 |
| 008557 | 17.5 | 126 | 51.3 | 0.0 | 0.4 |
| 010647 | 3.8 | 106 | 355.3 | 0.0 | 3.4 |
| 10640 | 0.7 | 43 | 9.2 | 0.0 | 0.2 |
| 7329 | 3.4 | 191 | 287.3 | 0.0 | 1.5 |
| 008605 | 6.0 | 82 | 733.5 | 0.0 | 9.0 |
| Mean | 5.8 | 120.7 | 155.5 | 0.0 | 1.4 |
| Median | 5.0 | 105.7 | 54.3 | 0.0 | 0.4 |
| St. Dev. | 4.3 | 51.7 | 207.6 | 0.0 | 2.4 |

TABLE 3

Normal Subjects

| Patient ID | PSD | D-Dimer | BNP | TnI | Ratio |
|---|---|---|---|---|---|
| 001511 | 5.1 | 90 | 20.4 | 0.0 | 0.2 |
| 001515 | 1.9 | 36 | 8.9 | 0.0 | 0.2 |
| 001520 | 1.0 | 61 | 6.5 | 0.0 | 0.1 |
| 001521 | 4.6 | 72 | 3.8 | 0.0 | 0.1 |
| 001524 | 2.3 | 69 | 11.1 | 0.0 | 0.2 |
| 001607 | 3.6 | 72 | 23.4 | 0.0 | 0.3 |
| 001610 | 1.1 | 52 | 18.3 | 0.0 | 0.4 |
| 001613 | 0.2 | 40 | 0.0 | 0.0 | 0.0 |
| 001616 | 2.6 | 28 | 0.0 | 0.0 | 0.0 |
| 001619 | 0.3 | 44 | 0.0 | 0.0 | 0.0 |
| 001622 | 1.4 | 25 | 0.0 | 0.0 | 0.0 |
| 001625 | 4.6 | 142 | 0.0 | 0.0 | 0.0 |
| 001628 | 1.6 | 40 | 0.0 | 0.0 | 0.0 |
| 001631 | 4.6 | 57 | 0.0 | 0.0 | 0.0 |
| 001634 | 7.2 | 60 | 6.6 | 0.0 | 0.1 |
| 001637 | 5.5 | 55 | 0.0 | 0.0 | 0.0 |
| 001640 | 0.0 | 260 | 19.1 | 0.0 | 0.1 |
| 001643 | 2.5 | 50 | 7.7 | 0.0 | 0.2 |
| 001646 | 0.0 | 56 | 4.7 | 0.0 | 0.1 |
| 002202 | 1.0 | 59 | 27.4 | 0.0 | 0.5 |
| 002205 | 1.7 | 39 | 23.4 | 0.0 | 0.6 |
| 002208 | 1.1 | 25 | 25.9 | 0.0 | 1.0 |
| 002211 | 0.9 | 55 | 45.9 | 0.0 | 0.8 |
| 002214 | 0.0 | 97 | 23.4 | 0.0 | 0.2 |
| 002217 | 2.8 | 117 | 15.3 | 0.0 | 0.1 |
| 002220 | 0.3 | 55 | 11.3 | 0.0 | 0.2 |
| 002223 | 2.5 | 47 | 8.1 | 0.0 | 0.2 |
| 002228 | 2.2 | 44 | 24.3 | 0.0 | 0.5 |
| 002229 | 2.6 | 61 | 11.2 | 0.0 | 0.2 |
| 002232 | 0.7 | 69 | 10.5 | 0.0 | 0.2 |
| 002235 | 0.0 | 54 | 4.0 | 0.0 | 0.1 |
| 002238 | 1.5 | 53 | 9.6 | 0.0 | 0.2 |
| 002241 | 7.5 | 16 | 10.8 | 0.0 | 0.7 |
| 002244 | 8.6 | 44 | 10.7 | 0.0 | 0.2 |
| 002247 | 3.7 | 68 | 33.1 | 0.0 | 0.5 |
| Mean | 2.5 | 63.3 | 12.2 | 0.0 | 0.2 |
| Median | 1.9 | 55.0 | 10.5 | 0.0 | 0.2 |
| St. Dev. | 2.3 | 42.3 | 11.1 | 0.0 | 0.3 |

These data indicate that the median D-dimer levels in the patients diagnosed with pulmonary embolism is higher than for the CHF patients, which is itself higher than normal subjects. Pulmonary surfactant protein D levels appears to be elevated over normals to nearly the same extent in both disease groups compared to normals. Using <82 μg/ml d-dimer as the rule-out cutoff for a diagnosis of pulmonary embolism would result in one false negative diagnosis, and would correctly rule out 18 of the 35 CHF patients and 30 of the 35 normals. For this patient population, using a BNP/d-dimer ratio of >3.4 as the rule-out cutoff would again result in one false negative diagnosis, but would correctly rule out 25 of the 35 CHF patients. The low cardiac troponin I level in all disease and normal subjects correctly rules out the occurrence of myocardial infarction in the entire test population. This example demonstrates that the differential diagnosis of causes of dyspnea can be accomplished through the measurement of d-dimer, BNP and cardiac troponin. Additionally, pulmonary embolism can be ruled in when BNP, d-dimer and pulmonary surfactant protein D levels are elevated above normal levels and troponin levels are normal. Pulmonary embolism can be ruled out when d dimer levels are in the normal range. When BNP levels are above normal, one can rule in congestive heart failure. When cardiac troponin levels are above normal, cardiac ischemia and necrosis can be ruled in.

Example 4

Identification of diastolic dysfunction

The following table compares levels of BNP, vasopressin, endothelin-2, calcitonin gene related peptide, urotensin 2, ANP, angiotensis 2, the ratios of BNP:CGRP, BNP:ANP, BNP:urotensin 2, and calcitonin in heart disease patients and normal subjects. The heart disease patients are subdivided according to the New York Heart Association classification of functional capacity and objective assessment. See, *Nomenclature and Criteria for Diagnosis of Diseases of the Heart and Great Vessels*. 9th ed. Boston, Mass.: Little, Brown & Co; 1994, pp. 253-256. The classification is made as follows:

| Class | Functional Capacity | Objective Assessment |
|---|---|---|
| NYHA1 | Patients with cardiac disease but without resulting limitation of physical activity. Ordinary physical activity does not cause undue fatigue, palpitation, dyspnea, or anginal pain. | No objective evidence of cardiovascular disease. |
| NYHA2 | Patients with cardiac disease resulting in slight limitation of physical activity. They are comfortable at rest. Ordinary physical activity results in fatigue, palpitation, dyspnea, or anginal pain. | Objective evidence of minimal cardiovascular disease. |
| NYHA3 | Patients with cardiac disease resulting in marked limitation of physical activity. They are comfortable at rest. Less than ordinary activity causes fatigue, palpitation, dyspnea, or anginal pain. | Objective evidence of moderately severe cardiovascular disease. |
| NYHA4 | Patients with cardiac disease resulting in inability to carry on any physical activity without discomfort. Symptoms of heart failure or the anginal syndrome may be present even at rest. If any physical activity is undertaken, discomfort is increased. | Objective evidence of severe cardiovascular disease. |

DD indicates patients having a clinical diagnosis of diastolic dysfunction, and exhibit an ejection fraction of >50%. Low ejection fraction (EF) patients are those exhibiting an ejection fraction of <50%, and are NYHA4 class patients considered to exhibit systolic, rather than diastolic, dysfunction. All units are ng/ml except BNP (pg/ml) and ratios, and N is the number of subjects in each group.

TABLE 4

|  | BNP | Vaso-pressin | Endothelin 2 | CGRP | BNP/CGRP | Calcitonin |
|---|---|---|---|---|---|---|
| Normal | 0 | 0.98 | 3.60 | 0.94 | 0 | 0.14 |
| DD NYHA1 | 142 | 1.13 | 4.63 | 1.06 | 247 | 0.20 |
| DD NYHA2 | 152 | 0.89 | 3.70 | 0.77 | 289 | 0.19 |
| DD NYHA3 | 325 | 0.84 | 3.72 | 1.02 | 309 | 0.16 |
| DD NYHA4 | 600 | 0.99 | 4.38 | 0.66 | 853 | 0.17 |
| DD All | 262 | 0.89 | 3.91 | 0.77 | 366 | 0.19 |
| Low EF | 839 | 1.10 | 4.38 | 0.97 | 957 | 0.19 |

|  | Urotensin 2 | BNP/U2 | ANP | BNP/ANP | Angiotensin 2 | N |
|---|---|---|---|---|---|---|
| Normal | 14.6 | 0 | 1.84 | 0 | 0.09 | 20 |
| DD NYHA1 | 18.9 | 11 | 2.11 | 162 | 0.09 | 2 |
| DD NYHA2 | 18.4 | 9 | 1.48 | 113 | 0.08 | 6 |
| DD NYHA3 | 18.8 | 16 | 1.95 | 149 | 0.09 | 6 |
| DD NYHA4 | 19.8 | 30 | 1.07 | 297 | 0.06 | 6 |
| DD All | 19.0 | 14 | 1.50 | 177 | 0.08 |  |
| Low EF | 28.0 | 41 | 2.17 | 413 | 0.07 | 20 |

These data indicate that Urotensin-2 and ANP can distinguish diastolic dysfunction from systolic dysfunction. In both cases, the levels are higher in systolic dysfunction than in diastolic dysfunction. Moreover, with the addition of BNP, the the ability to discriminate diastolic dysfunction from systolic dysfunction is enhanced, as elevation of both BNP and ANP appears to be indicative of systolic dysfunction while elevation of BNP with ANP at or below normal levels appears to be indicative of diastolic dysfunction. Urotensin 2 shows a similar pattern. CGRP contributes to the ability to distinguish diastolic from systolic dysfunction when expressed as a ratio with BNP where the ratio is greater in cases of systolic dysfunction relative to diastolic dysfunction.

Hammer-Lercher discusses the significance, or lack thereof, of NT-proBNP levels in controls and in patients with diastolic dysfunction (Hammer-Lercher et al., Clin. Chim. Acta 310(2):193-7 (2001). In a preferred embodiment, a panel consisting of BNP and NTproBNP can distinguish heart failure patients with diastolic dysfunction. When both NTproBNP and BNP are elevated above the cutoff, the patient has systolic dysfunction. When NTproBNP is not elevated, but BNP is elevated above the cutoff, this would signify that the patient suffers from diastolic dysfunction.

While the invention has been described and exemplified in sufficient detail for those skilled in this art to make and use it, various alternatives, modifications, and improvements should be apparent without departing from the spirit and scope of the invention.

One skilled in the art readily appreciates that the present invention is well adapted to carry out the objects and obtain the ends and advantages mentioned, as well as those inherent therein. The examples provided herein are representative of preferred embodiments, are exemplary, and are not intended as limitations on the scope of the invention. Modifications therein and other uses will occur to those skilled in the art. These modifications are encompassed within the spirit of the invention and are defined by the scope of the claims.

It will be readily apparent to a person skilled in the art that varying substitutions and modifications may be made to the invention disclosed herein without departing from the scope and spirit of the invention.

All patents and publications mentioned in the specification are indicative of the levels of those of ordinary skill in the art to which the invention pertains. All patents and publications are herein incorporated by reference to the same extent as if each individual publication was specifically and individually indicated to be incorporated by reference.

The invention illustratively described herein suitably may be practiced in the absence of any element or elements, limitation or limitations which is not specifically disclosed herein. Thus, for example, in each instance herein any of the terms "comprising", "consisting essentially of" and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

Other embodiments are set forth within the following claims.

We claim:

1. A method, comprising:
   contacting a test sample obtained from a subject with a test surface of a diagnostic device, wherein the test surface is within a capillary space of the diagnostic device and comprises a plurality of discrete addressable locations, each of the discrete addressable locations comprising discrete immobilized particles comprising antibodies bound thereto for binding a marker, the diagnostic device comprising immobilized particles at discrete addressable locations for detecting each of B-type natriuretic peptide or a marker related to B-type natriuretic peptide, D-dimer, and at least one cardiac troponin form selected from the group consisting of free cardiac troponin I, free cardiac troponin T, cardiac troponin I in a complex comprising one or both of troponin T and troponin C, cardiac troponin T in a complex comprising one or both of troponin I and troponin C, total cardiac troponin I, and total cardiac troponin T;
   detecting the amount of each of B-type natriuretic peptide or a marker related to B-type natriuretic peptide, D-dimer, and at least one cardiac troponin form selected from the group consisting of free cardiac troponin I, free cardiac troponin T, cardiac troponin I in a complex comprising one or both of troponin T and troponin C, cardiac troponin T in a complex comprising one or both of troponin I and troponin C, total cardiac troponin I, and total cardiac troponin T; and
   determining the presence or absence of each of myocardial infarction, pulmonary embolism, and congestive heart failure in said subject based on the results obtained from said analyzing step;
   wherein detecting an amount of at least one cardiac troponin form above a threshold level rules in myocardial infarction;
   further wherein when a detected amount of at least one cardiac troponin form is below a threshold level, and the detected amount of D-dimer is above a threshold level, pulmonary embolism and congestive heart failure are distinguished by comparing the amount of D-dimer to the amount of BNP or a marker related thereto detected in said test sample.

2. The method according to claim 1, wherein said subject suffers from dyspnea.

3. The method according to claim 1, wherein said analyzing step further comprises performing one or more assays that detect one or more of pulmonary surfactant protein D and atrial natriuretic peptide or a marker related to atrial natriuretic peptide.

4. The method according to claim 1, wherein said marker related to B-type natriuretic peptide is NT-proBNP or proBNP.

5. The method according to claim 1, wherein said analyzing step further comprises performing one or more assays that detect one or more additional subject-derived markers related to myocardial injury.

6. The method according to claim 1, wherein said sample is blood, serum, or plasma.

7. The method according to claim 1, wherein said plurality of markers are detected in a sandwich immunoassay.

8. The method according to claim 1, wherein said test surface is a porous membrane.

9. The method according to claim 1, wherein said test surface is a nonporous surface.

10. The method according to claim 3, wherein said analyzing step further comprises performing an assay that detects pulmonary surfactant protein D.

11. The method according to claim 3, wherein said analyzing step further comprises performing an assay that detects atrial natriuretic peptide or a marker related to atrial natriuretic peptide.

12. The method according to claim 1, wherein said analyzing step further comprises performing one or more assays that detect one or more subject-derived markers related to coagulation and hemostasis.

13. The method of claim 1, wherein said method further comprises providing a treatment regimen to treat said subject based on determining the presence or absence of each or myocardial infarction, congestive heart failure, and pulmonary embolism.

* * * * *